(12) United States Patent
Connor

(10) Patent No.: US 10,627,861 B2
(45) Date of Patent: Apr. 21, 2020

(54) WEARABLE DEVICE FOR THE ARM WITH CLOSE-FITTING BIOMETRIC SENSORS

(71) Applicant: Robert A. Connor, St. Paul, MN (US)

(72) Inventor: Robert A. Connor, St. Paul, MN (US)

(73) Assignee: Medibotics, St. Paul, MN (US)

( * ) Notice: Subject to any disclaimer, the term of this patent is extended or adjusted under 35 U.S.C. 154(b) by 773 days.

(21) Appl. No.: 15/294,746

(22) Filed: Oct. 16, 2016

(65) Prior Publication Data
US 2017/0027511 A1    Feb. 2, 2017

Related U.S. Application Data

(63) Continuation of application No. 14/623,337, filed on Feb. 16, 2015, now Pat. No. 9,582,035, and a
(Continued)

(51) Int. Cl.
| | | |
|---|---|---|
| *A61B 5/1455* | (2006.01) | |
| *G06F 1/16* | (2006.01) | |
| *G06F 3/01* | (2006.01) | |
| *A41B 7/00* | (2006.01) | |
| *A41D 27/10* | (2006.01) | |
| *A44C 5/00* | (2006.01) | |
| *A44C 9/00* | (2006.01) | |
| *A61B 5/053* | (2006.01) | |
| *A61B 5/145* | (2006.01) | |
| *A61B 5/1477* | (2006.01) | |

(Continued)

(52) U.S. Cl.
CPC .............. *G06F 1/163* (2013.01); *A41B 7/00* (2013.01); *A41D 27/10* (2013.01); *A44C 5/0023* (2013.01); *A44C 9/0053* (2013.01); *A61B 5/0537* (2013.01); *A61B 5/1477* (2013.01); *A61B 5/14532* (2013.01); *A61B 5/14551* (2013.01); *A61B 5/4875* (2013.01); *A61B 5/6824* (2013.01); *A61B 5/6831* (2013.01); *A61B 5/6838* (2013.01); *G06F 1/1637* (2013.01); *G06F 1/1694* (2013.01); *G06F 3/014* (2013.01); *G06F 3/017* (2013.01); *A41D 2300/326* (2013.01); *A61B 2562/046* (2013.01); *G01N 21/27* (2013.01); *G01N 27/02* (2013.01)

(58) Field of Classification Search
CPC ........... A61B 5/00; A61B 5/68; A61B 5/6801; A61B 5/6802; A61B 5/681; A61B 5/6813; A61B 5/6824; A61B 5/683; A61B 5/6831; A61B 5/145; A61B 5/1455; A61B 5/14551; A61B 5/14552; A61B 5/14542; A61B 5/48; A61B 5/4869; A61B 5/4875; A61B 5/14532; A61B 5/0537; A61B 5/1477; A61B 5/0023; A61B 5/6838; G01N 21/00; G01N 21/17; G01N 21/25; G01N 21/27

See application file for complete search history.

(56) References Cited

U.S. PATENT DOCUMENTS

| | | | |
|---|---|---|---|
| 5,957,840 A | * | 9/1999 | Terasawa ............. A61B 5/6816 600/310 |
| 7,415,139 B2 | | 8/2008 | Takiguchi |

(Continued)

*Primary Examiner* — Eric F Winakur
*Assistant Examiner* — Chu Chuan Liu

(57) ABSTRACT

This is a wearable biometric device for an arm including spectroscopic sensors which project light onto an arm surface at different angles. Data from these sensors can be used to measure a person's hydration levels, oxygen levels, glucose levels, or heart rate.

13 Claims, 22 Drawing Sheets

Related U.S. Application Data continuation-in-part of application No. 14/951,475, filed on Nov. 24, 2015, now Pat. No. 10,314,492, which is a continuation-in-part of application No. 13/901,131, filed on May 23, 2013, now Pat. No. 9,536,449, and a continuation-in-part of application No. 14/071,112, filed on Nov. 4, 2013, now abandoned, and a continuation-in-part of application No. 14/623,337, filed on Feb. 16, 2015, now Pat. No. 9,582,035.

(60) Provisional application No. 61/944,090, filed on Feb. 25, 2014, provisional application No. 61/948,124, filed on Mar. 5, 2014, provisional application No. 62/100,217, filed on Jan. 6, 2015, provisional application No. 62/106,856, filed on Jan. 23, 2015, provisional application No. 62/111,163, filed on Feb. 3, 2015, provisional application No. 62/113,423, filed on Feb. 7, 2015, provisional application No. 62/115,691, filed on Feb. 13, 2015, provisional application No. 62/245,311, filed on Oct. 23, 2015, provisional application No. 62/349,277, filed on Jun. 13, 2016.

(51) Int. Cl.
*A61B 5/00* (2006.01)
*G01N 21/27* (2006.01)
*G01N 27/02* (2006.01)

(56) References Cited

U.S. PATENT DOCUMENTS

| | | |
|---|---|---|
| 7,627,357 B2 | 12/2009 | Zribi et al. |
| 7,680,522 B2 | 3/2010 | Andersohn et al. |
| 8,199,007 B2 | 6/2012 | Coakley et al. |
| 8,452,362 B2 | 5/2013 | Menon |
| 8,515,517 B2 | 8/2013 | Hayter et al. |
| 8,613,892 B2 | 12/2013 | Stafford |
| 8,868,147 B2 | 10/2014 | Stippick et al. |
| 8,930,145 B2 | 1/2015 | Li et al. |
| 8,961,415 B2 | 2/2015 | LeBoeuf et al. |
| 8,989,230 B2 | 3/2015 | Dummer et al. |
| 9,028,408 B2 | 5/2015 | Fischer |
| 9,037,204 B2 | 5/2015 | Schlottau |
| 9,061,899 B2 | 6/2015 | Rowe et al. |
| 9,107,644 B2 | 8/2015 | Frix et al. |
| 9,134,175 B2 | 9/2015 | Matsushita |
| 2002/0035317 A1* | 3/2002 | Cheng ............... A61B 5/14546 600/322 |
| 2008/0319299 A1 | 12/2008 | Stippick et al. |
| 2009/0018420 A1 | 1/2009 | White |
| 2009/0105605 A1 | 4/2009 | Abreu |
| 2010/0081901 A1* | 4/2010 | Buice ............... A61B 5/14551 600/324 |
| 2010/0249546 A1 | 9/2010 | White |
| 2011/0166553 A1 | 7/2011 | Holmes et al. |
| 2012/0056289 A1 | 3/2012 | Tian et al. |
| 2012/0095352 A1 | 4/2012 | Tran |
| 2013/0041235 A1 | 2/2013 | Rogers et al. |
| 2013/0056249 A1 | 3/2013 | Taguchi et al. |
| 2013/0197319 A1 | 8/2013 | Monty et al. |
| 2013/0199822 A1 | 8/2013 | Fan et al. |
| 2013/0248380 A1 | 9/2013 | Cui |
| 2014/0009638 A1 | 1/2014 | Baraniuk et al. |
| 2014/0058220 A1 | 2/2014 | LeBoeuf et al. |
| 2014/0064315 A1 | 3/2014 | Dummer et al. |
| 2014/0148658 A1 | 5/2014 | Zalevsky et al. |
| 2014/0275852 A1* | 9/2014 | Hong ............... A61B 5/02427 600/301 |
| 2014/0339438 A1 | 11/2014 | Correns et al. |
| 2015/0005640 A1 | 1/2015 | Davis et al. |
| 2015/0005644 A1 | 1/2015 | Rhoads |
| 2015/0015888 A1 | 1/2015 | Gulati et al. |
| 2015/0018646 A1 | 1/2015 | Gulati et al. |
| 2015/0073723 A1 | 3/2015 | Mulligan et al. |
| 2015/0094551 A1 | 4/2015 | Frix et al. |
| 2015/0099943 A1 | 4/2015 | Russell |
| 2015/0112170 A1 | 4/2015 | Amerson et al. |
| 2015/0126824 A1 | 5/2015 | LeBoeuf et al. |
| 2015/0126825 A1 | 5/2015 | LeBoeuf et al. |
| 2015/0130633 A1 | 5/2015 | Grubstein et al. |
| 2015/0130634 A1 | 5/2015 | Grubstein et al. |
| 2015/0135118 A1 | 5/2015 | Grubstein et al. |
| 2015/0141769 A1 | 5/2015 | Mulligan et al. |
| 2015/0148623 A1 | 5/2015 | Benaron |
| 2015/0148624 A1 | 5/2015 | Benaron |
| 2015/0148636 A1 | 5/2015 | Benaron |
| 2015/0168217 A1 | 6/2015 | Englund et al. |
| 2015/0192462 A1 | 7/2015 | Schiering et al. |
| 2015/0216454 A1 | 8/2015 | Kasahara et al. |
| 2015/0216479 A1 | 8/2015 | Abreu |
| 2015/0216484 A1 | 8/2015 | Kasahara et al. |
| 2015/0224275 A1 | 8/2015 | Pastoor et al. |
| 2015/0233762 A1 | 8/2015 | Goldring et al. |
| 2015/0238083 A1 | 8/2015 | Faubert et al. |
| 2015/0260573 A1 | 9/2015 | Ishimaru |
| 2015/0260650 A1 | 9/2015 | Ashrafi et al. |

* cited by examiner

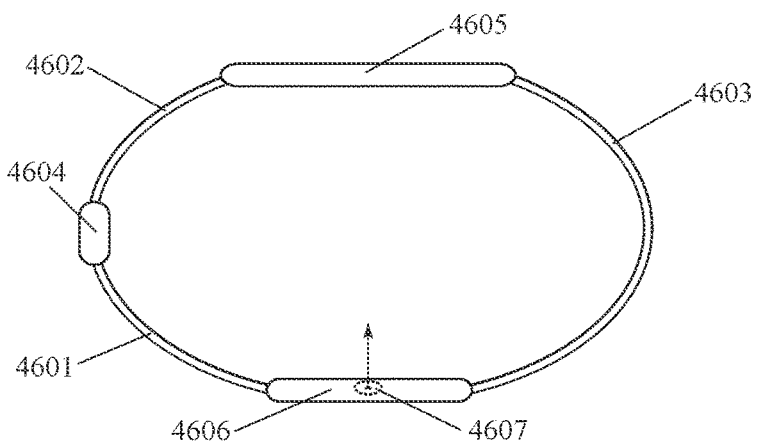
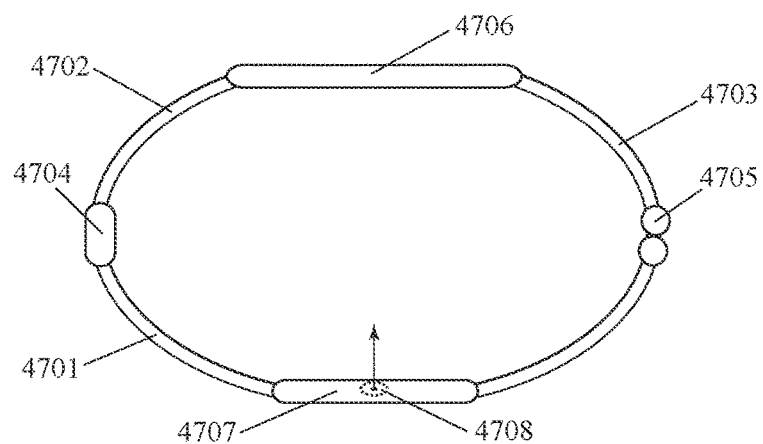
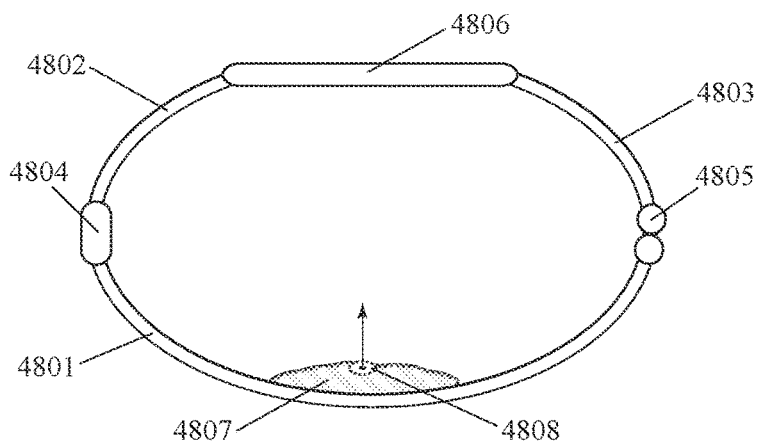

WEARABLE DEVICE FOR THE ARM WITH CLOSE-FITTING BIOMETRIC SENSORS

CROSS-REFERENCE TO RELATED APPLICATIONS

This patent application:

(1) is a continuation in part of U.S. patent application Ser. No. 14/623,337 by Robert A. Connor entitled "Wearable Computing Devices and Methods for the Wrist and/or Forearm" filed on Feb. 16, 2015 which, in turn, claimed the priority benefit of: U.S. Provisional Patent Application No. 61/944,090 entitled "Wearable Computing Device for the Wrist and/or Arm" by Robert A. Connor with a filing date of Feb. 25, 2014; U.S. Provisional Patent Application No. 61/948,124 entitled "Wearable Computing Device for the Wrist and/or Arm" by Robert A. Connor with a filing date of Mar. 5, 2014; U.S. Provisional Patent Application No. 62/100,217 entitled "Forearm Wearable Device with Distal-to-Proximal Flexibly-Connected Display Modules" by Robert A. Connor with a filing date of Jan. 6, 2015; U.S. Provisional Patent Application No. 62/106,856 entitled "Forearm Wearable Computing Device with Proximal and Distal Arcuate Bands" by Robert A. Connor with a filing date of Jan. 23, 2015; U.S. Provisional Patent Application No. 62/111,163 entitled "Forearm-Wearable Computing Device with Large Display Area" by Robert A. Connor with a filing date of Feb. 3, 2015; U.S. Provisional Patent Application No. 62/113,423 entitled "Sensor-Informed Modification of the Interface Modality Between a Human and a Wearable Computing Device" by Robert A. Connor with a filing date of Feb. 7, 2015; and U.S. Provisional Patent Application No. 62/115,691 entitled "Adjustment of Wearable Computer-to-Human Interface Based on Environmental and/or Physiological Sensors" by Robert A. Connor with a filing date of Feb. 13, 2015;

(2) is a continuation in part of U.S. patent application Ser. No. 14/951,475 by Robert A. Connor entitled "Wearable Spectroscopic Sensor to Measure Food Consumption Based on Interaction Between Light and the Human Body" filed on Nov. 24, 2015 which, in turn: (a) is a continuation in part of U.S. patent application Ser. No. 13/901,131 by Robert A. Connor entitled "Smart Watch and Food Utensil for Monitoring Food Consumption" filed on May 23, 2013; (b) is a continuation in part of U.S. patent application Ser. No. 14/071,112 by Robert A. Connor entitled "Wearable Spectroscopy Sensor to Measure Food Consumption" filed on Nov. 4, 2013; (c) is a continuation in part of U.S. patent application Ser. No. 14/623,337 by Robert A. Connor entitled "Wearable Computing Devices and Methods for the Wrist and/or Forearm" filed on Feb. 16, 2015; and (d) claims the priority benefit of U.S. provisional patent application 62/245,311 by Robert A. Connor entitled "Wearable Device for the Arm with Close-Fitting Biometric Sensors" filed on Oct. 23, 2015;

(3) claims the priority benefit of U.S. provisional patent application 62/245,311 by Robert A. Connor entitled "Wearable Device for the Arm with Close-Fitting Biometric Sensors" filed on Oct. 23, 2015; and (4) claims the priority benefit of U.S. provisional patent application 62/349,277 by Robert A. Connor entitled "Glucowear™ System for Monitoring and Managing Intra-body Glucose Levels" filed on Jun. 13, 2016.

The entire contents of these related applications are incorporated herein by reference.

FEDERALLY SPONSORED RESEARCH

Not Applicable

SEQUENCE LISTING OR PROGRAM

Not Applicable

BACKGROUND

Field of Invention

This invention relates to wearable biometric sensors.

Introduction

Wearable devices with biometric sensors to measure a person's hydration levels, oxygen levels, glucose levels, or heart rate are known in the prior art. However, it can be challenging keeping biometric sensors in close, uniform contact with body tissue for consistent operation when there are complex unique body contours to which wearable devices do not easily conform and body movements which can cause wearable devices to shift their location relative to the body surface. The prior art does not completely solve the problem of how to create a wearable device which is not restrictive or uncomfortable, but yet keeps biometric sensors in close, uniform contact with body tissue for consistent operation. The invention disclosed herein solves this problem.

REVIEW OF THE PRIOR ART

U.S. Pat. No. 7,415,139 (Takiguchi, Aug. 19, 2008) entitled "Living-Tissue Pattern Detecting Method, Living-Tissue Pattern Detecting Device, Biometric Authentication Method, and Biometric Authentication Device" discloses the use of near-infrared light for optical detection of the roughness distribution pattern of deep-layer tissue. U.S. Pat. No. 7,627,357 (Zribi et al., Dec. 1, 2009) entitled "System and Method for Non-Invasive Glucose Monitoring" discloses a method for determining analyte concentration levels by scattering radiation scattered off, or through, a target. U.S. Pat. No. 7,680,522 (Andersohn et al., Mar. 16, 2010) entitled "Method and Apparatus for Detecting Misapplied Sensors" discloses a method and system for determining whether a spectrophotometric sensor is misapplied.

U.S. Pat. No. 8,199,007 (Coakley et al., Jun. 12, 2012) entitled "Flex Circuit Snap Track for a Biometric Sensor" discloses a sensor assembly configured to house an optical component. U.S. Pat. No. 8,452,362 (Menon, May 28, 2013) entitled "Method and System for Monitoring Hydration" discloses a device for measuring hydration status by illuminating at least a portion of an anterior region of an eye. U.S. Pat. No. 8,515,517 (Hayter et al., Aug. 20, 2013) entitled "Method and System for Dynamically Updating Calibration Parameters for an Analyte Sensor" discloses methods and apparatuses for determining and dynamically updating a calibration parameter. U.S. Pat. No. 8,613,892 (Stafford, Dec. 24, 2013) entitled "Analyte Meter with a Moveable Head and Methods of Using the Same" discloses in vitro analyte meters with moveable meter portions.

U.S. Pat. No. 8,868,147 (Stippick et al., Oct. 21, 2014) entitled "Method and Apparatus for Controlling Positioning of a Noninvasive Analyzer Sample Probe" discloses a probe interface method and apparatus for use in conjunction with an optical based noninvasive analyzer. U.S. Pat. No. 8,930,145 (Li et al., Jan. 6, 2015) entitled "Light Focusing Continuous Wave Photoacoustic Spectroscopy and Its Applications to Patient Monitoring" discloses systems and methods that use spatial modulation to focus continuous wave light into a localized region of interest such as an individual blood vessel. U.S. Pat. No. 8,961,415 (LeBoeuf et al., Feb. 24, 2015) entitled "Methods and Apparatus for Assessing Physiological Conditions" discloses monitoring apparatuses and methods to detect physiological information from a subject such as heart rate, subject activity level, subject tympanic membrane temperature, and subject breathing rate.

U.S. Pat. No. 8,989,230 (Dummer et al., Mar. 24, 2015) entitled "Method and Apparatus Including Movable-Mirror MEMS-Tuned Surface-Emitting Lasers" discloses an apparatus having a substrate, a solid-state gain medium, a reflective mirror on one side of the medium, a movable reflective mirror on an opposite side of the medium, and a mechanism configured to move the movable mirror to tune a characteristic wavelength. U.S. Pat. No. 9,028,408 (Fischer, May 12, 2015) entitled "Detection Device for the Detection of a Blood Count Parameter" discloses a device for detecting a blood count parameter in a blood vessel comprising a transmitter having a number of transmit antennas for transmitting at least one transmit signal, a receiver having a number of receive antennas for receiving at least one receive signal, and a processor to select a detection configuration.

U.S. Pat. No. 9,037,204 (Schlottau, May 19, 2015) entitled "Filtered Detector Array for Optical Patient Sensors" discloses optical patient monitoring systems including a broadband emitter configured to emit two or more wavelengths of light into the tissue of a patient. U.S. Pat. No. 9,061,899 (Rowe et al., Jun. 23, 2015) entitled "Apparatus and Method of Biometric Determination Using Specialized Optical Spectroscopy Systems" discloses methods and apparatuses for performing biometric determinations using optical spectroscopy of tissue including include determination or verifications of identity, estimation of age, estimation of sex, determination of sample liveness and sample authenticity. U.S. Pat. No. 9,107,644 (Frix et al., Aug. 18, 2015) entitled "Continuous Transdermal Monitoring System and Method" discloses methods and systems for continuous transdermal monitoring ("CTM") contingent on an output signal from an accelerometer.

U.S. Pat. No. 9,134,175 (Matsushita, Sep. 15, 2015) entitled "Measurement Device" discloses a spectrometry device including a wavelength-tunable interference filter that is provided with a stationary reflection film, a movable reflection film and an electrostatic actuator which changes a gap dimension between the stationary reflection film and the movable reflection film. U.S. Patent Application 20080319299 (Stippick et al., Dec. 25, 2008) entitled "Method and Apparatus for Controlling Positioning of a Noninvasive Analyzer Sample Probe" discloses a probe interface method and apparatus for use in conjunction with an optical based noninvasive analyzer, wherein an algorithm controls a sample probe position and attitude relative to a skin sample site before and/or during sampling. U.S. Patent Application 20090018420 (White, Jan. 15, 2009) entitled "Apparatus for Non-Invasive Spectroscopic Measurement of Analytes, and Method of Using the Same" discloses an apparatus for spectroscopic evaluation of a subject's body fluids at the interstitial region adjacent to or in between a subject's extremities.

U.S. Patent Application 20090105605 (Abreu, Apr. 23, 2009) entitled "Apparatus and Method for Measuring Biologic Parameters" discloses a sensor fitted on support structures using a special geometry for acquiring continuous and undisturbed data on the physiology of the body. U.S. Patent Application 20100249546 (White, Sep. 30, 2010) entitled "Apparatus for Non-Invasive Spectroscopic Measurement of Analytes, and Method of Using the Same" discloses an apparatus for spectroscopic evaluation of a subject's body fluids at the interstitial region adjacent to or in between a subject's extremities. U.S. Patent Application 20110166553 (Holmes et al., Jul. 7, 2011) entitled "Medical Device for Analyte Monitoring and Drug Delivery" discloses an ingestible, implantable, or wearable medical device comprising a microarray which comprises a bioactive agent capable of interacting with a disease marker biological analyte.

U.S. Patent Application 20120056289 (Tian et al., Mar. 8, 2012) entitled "Materials, Systems and Methods for Optoelectronic Devices" discloses a photodetector comprising an integrated circuit and at least two optically sensitive layers. U.S. Patent Application 20120095352 (Tran, Apr. 19, 2012) entitled "Health Monitoring Appliance" discloses a heart monitoring system including one or more wireless nodes forming a wireless network; a wearable sensor having a wireless transceiver adapted to communicate with the one or more wireless nodes; and a software module receiving data from the wireless nodes to detect changes in patient vital signs. U.S. Patent Application 20130041235 (Rogers et al., Feb. 14, 2013) entitled "Flexible and Stretchable Electronic Systems for Epidermal Electronics" discloses skin-mounted biomedical devices and methods of making and using biomedical devices for sensing and actuation applications.

U.S. Patent Application 20130056249 (Taguchi et al., Mar. 7, 2013) entitled "Flexible Conductive Material, Method of Manufacturing the Same, and Electrode, Wiring, Electromagnetic Wave Shield and Transducer Using the Flexible Conductive Material" discloses a flexible conductive material that includes an elastomer and a conductive material including silver at least in a surface. U.S. Patent Application 20130197319 (Monty et al., Aug. 1, 2013) entitled "Flexible Electrode for Detecting Changes in Temperature, Humidity, and Sodium Ion Concentration in Sweat" discloses a flexible sensor suitable for contact with skin comprising: a nanocomposite; and a top layer; where the sensor provides in-situ detection in sweat or other aqueous body fluids at the skin surface of at least one physiological parameter selected from the group consisting of a physiological salt component, temperature, moisture, humidity, or combinations thereof.

U.S. Patent Application 20130199822 (Fan et al., Aug. 8, 2013) entitled "Flexible, Permeable, Electrically Conductive and Transparent Textiles and Methods for Making Them" discloses methods for forming a flexible, permeable, electrically conductive and substantially transparent textile utilizing vapor phase deposition. U.S. Patent Application 20130248380 (Cui, Sep. 26, 2013) entitled "Flexible Graphene Biosensor" discloses a biosensor comprising a graphene electrode linked to a biosensing element a linker, wherein the biosensing element is bonded to a flexible substrate. U.S. Patent Application 20140009638 (Baraniuk et al., Jan. 9, 2014) entitled "Dual-Port Measurements of Light Reflected from Micromirror Array" discloses an imaging system and method that captures compressive sensing (CS) measurements of a received light stream and also obtains samples of background light level (BGLL).

U.S. Patent Application 20140058220 (LeBoeuf et al., Feb. 7, 2014) entitled "Apparatus, Systems and Methods for Obtaining Cleaner Physiological Information Signals" discloses real-time, noninvasive health and environmental monitors including a plurality of compact sensors integrated within small, low-profile devices, such as earpiece modules. U.S. Patent Application 20140064315 (Dummer et al., Mar. 6, 2014) entitled "Method and Apparatus Including Movable-Mirror MEMS-Tuned Surface-Emitting Lasers" discloses a VCSEL apparatus having a substrate, a solid-state gain medium, a reflective mirror on one side of the medium, a movable reflective mirror on an opposite side of the medium, and a mechanism configured to move the movable mirror to tune a characteristic wavelength. U.S. Patent Application 20140148658 (Zalevsky et al., May 29, 2014) entitled "Method and System for Non-Invasively Monitoring Biological or Biochemical Parameters of Individual" discloses a system and method which measures speckle patterns generated by a portion of a person's body.

U.S. Patent Application 20140339438 (Correns et al., Nov. 20, 2014) entitled "Devices and Methods for Spectroscopic Analysis" discloses devices and methods for spectrometric analysis of light-emitting samples. U.S. Patent Application 20150005640 (Davis et al., Jan. 1, 2015) entitled "Gesture-Based Dermatologic Data Collection and Presentation" discloses movement of a smartphone camera to capture dermatologic imagery from a variety of viewpoints. U.S. Patent Application 20150005644 (Rhoads, Jan. 1, 2015) entitled "Dermoscopic Data Acquisition Employing Display Illumination" discloses use of a smartphone camera to gather skin imagery while controlled spectral illumination is emitted from the smartphone display. U.S. Patent Application 20150015888 (Gulati et al., Jan. 15, 2015) entitled "Dynamic Radially Controlled Light Input to a Noninvasive Analyzer Apparatus and Method of Use Thereof" discloses an analyzer apparatus and method to dynamically irradiate a sample with incident light where the incident light is varied in time in terms of any of: position, radial position relative to a point of the skin of a subject, solid angle, incident angle, depth of focus, energy, and/or intensity.

U.S. Patent Application 20150018646 (Gulati et al., Jan. 15, 2015) entitled "Dynamic Sample Mapping Noninvasive Analyzer Apparatus and Method of Use Thereof" discloses an apparatus and method which uses a sample mapping phase to establish one or more analyzer/software parameters used in a subsequent individual and/or group specific data collection phase. U.S. Patent Application 20150073723 (Mulligan et al., Mar. 12, 2015) entitled "Noninvasive Hydration Monitoring" discloses novel tools and techniques for assessing, predicting and/or estimating the hydration of a patient and/or an amount of fluid needed for effective hydration of the patient. U.S. Patent Application 20150094551 (Frix et al., Apr. 2, 2015) entitled "Continuous Transdermal Monitoring System and Method" discloses methods and systems for continuous transdermal monitoring ("CTM") with a pulse oximetry sensor having a plurality of light detectors arranged as an array.

U.S. Patent Application 20150099943 (Russell, Apr. 9, 2015) entitled "Wearable Physiological Sensing Device with Optical Pathways" discloses a wearable physiological sensing device may with at least one light source; a first light pipe coupled with the at least one light source, the first light pipe at least partially circumscribing an extremity of a patient, and at least one aperture for radiating light from the light source into the extremity. U.S. Patent Application 20150112170 (Amerson et al., Apr. 23, 2015) entitled "Device and Method for Non-Invasive Glucose Monitoring" discloses a device and method for non-invasively measuring analytes and physiological parameters measuring terahertz radiation emitted though biological tissue. U.S. Patent Application 20150126824 (LeBoeuf et al., May 7, 2015) entitled "Apparatus for Assessing Physiological Conditions" discloses monitoring apparatuses and methods for assessing a physiological condition of a subject including at least two types of physiological information and possibly also environmental information.

U.S. Patent Application 20150126825 (LeBoeuf et al., May 7, 2015) entitled "Physiological Monitoring Apparatus" discloses wearable apparatuses including a plurality of compact sensors integrated within small, low-profile devices such as earpiece modules for monitoring various physiological and environmental factors. U.S. Patent Application 20150130633 (Grubstein et al., May 14, 2015) and 20150130634 (Grubstein et al., May 14, 2015) entitled "Indicator and Analytics for Sensor Insertion in a Continuous Analyte Monitoring System and Related Methods", both entitled "Indicator and Analytics for Sensor Insertion in a Continuous Analyte Monitoring System and Related Methods," disclose systems and methods for tracking sensor insertion locations in a continuous analyte monitoring system. U.S. Patent Application 20150135118 (Grubstein et al., May 14, 2015) entitled "Indicator and Analytics for Sensor Insertion in a Continuous Analyte Monitoring System and Related Methods" discloses systems and methods for, among others, tracking sensor insertion locations in a continuous analyte monitoring system.

U.S. Patent Application 20150141769 (Mulligan et al., May 21, 2015) entitled "Noninvasive Monitoring for Fluid Resuscitation" discloses novel tools and techniques for assessing, predicting and/or estimating the effectiveness of fluid resuscitation of a patient and/or an amount of fluid needed for effective resuscitation of the patient. U.S. Patent Application 20150148623 (Benaron, May 28, 2015) entitled "Hydration Monitoring Sensor and Method for Cell Phones, Smart Watches, Occupancy Sensors, and Wearables" discloses a sensor for hydration monitoring in mobile devices, wearables, security, illumination, photography, and other devices and systems using an optional phosphor-coated broadband white LED to produce broadband light which is then transmitted along with any ambient light to a body target. U.S. Patent Application 20150148624 (Benaron, May 28, 2015) entitled "Method for Detecting Physiology at Distance or During Movement for Mobile Devices, Illumination, Security, Occupancy Sensors, and Wearables" discloses a sensor which uses broadband light transmitted to a target such as the ear, face, or wrist of a living subject.

U.S. Patent Application 20150148636 (Benaron, May 28, 2015) entitled "Ambient Light Method for Cell Phones, Smart Watches, Occupancy Sensors, and Wearables" discloses a sensor for respiratory and metabolic monitoring in mobile devices, wearables, security, illumination, photography, and other devices and systems using a broadband ambient light transmitted to a target such as the ear, face, or wrist. U.S. Patent Application 20150168217 (Englund et al., Jun. 18, 2015) entitled "Methods and Apparatus for Spectrometry" discloses how multimode interference can be used to achieve ultra-high resolving powers and a broad spectroscopy range within a monolithic, millimeter-scale device. U.S. Patent Application 20150192462 (Schiering et al., Jul. 9, 2015) entitled "Dual Spectrometer" discloses systems and techniques for optical spectrometer detection using IR spectroscopy components and Raman spectroscopy components.

U.S. Patent Application 20150216454 (Kasahara et al., Aug. 6, 2015) entitled "Biological Information Measurement Apparatus and Biological Information Measurement Method" discloses a blood glucose level measurement apparatus which is mounted on the wrist or the like of a user and performs a measurement using light. U.S. Patent Application 20150216479 (Abreu, Aug. 6, 2015) entitled "Apparatus and Method for Measuring Biologic Parameters" discloses support structures for positioning sensors on a physiologic tunnel for measuring physical, chemical and biological parameters of the body.

U.S. Patent Application 20150216484 (Kasahara et al., Aug. 6, 2015) entitled "Biological Information Processing Apparatus, and Biological Information Processing Method" discloses a measurement method selection unit which selects one measurement method on the basis of a detection result from a body motion detection unit, from among a plurality of measurement methods of measuring a blood glucose level applying irradiation waves toward a living body of the subject. U.S. Patent Application 20150224275 (Pastoor et al., Aug. 13, 2015) entitled "Customisation or Adjustment of Patient Interfaces" discloses a sensor device in the form of a patient interface which has a sensor arrangement for determining a degree of fitting of a contact surface to the patient. U.S. Patent Application 20150233762 (Goldring et al., Aug. 20, 2015) entitled "Spectrometry System with Illuminator" discloses a spectrometer comprising a plurality of isolated optical channels.

U.S. Patent Application 20150238083 (Faubert et al., Aug. 27, 2015) entitled "Method and System for Optically Investigating a Tissue of a Subject" discloses a probe device for optically investigating a tissue of a subject, comprising: a first probe element, a second probe element, and a third probe element each to be positioned at a respective vertex of a triangle for sensing the tissue, the first probe element each comprising a first light source for emitting light having a first wavelength, the second probe element each comprising a second light source for emitting light having a second wavelength and a first photodetector for detecting light having the first wavelength and scattered the tissue, and the third probe element comprising a second photodetector for detecting light having the first and second wavelengths and scattered the tissue.

U.S. Patent Application 20150260573 (Ishimaru, Sep. 17, 2015) entitled "Spectroscopic Measurement Device" discloses a spectroscopic measurement device including a dark filter that is arranged on an optical path between an imaging optical system and a light detection unit and includes a plurality of regions having different transmittances. U.S. Patent Application 20150260650 (Ashrafi et al., Sep. 17, 2015) entitled "System and Method for Making Concentration Measurements Within a Sample Material Using Orbital Angular Momentum" discloses signal generation circuitry which generates a first signal having at least one orbital angular momentum applied thereto and applies the first signal to the sample.

SUMMARY OF THE INVENTION

The prior art does not completely solve the problem of how to create a wearable device which is not restrictive or uncomfortable, but yet keeps biometric sensors in close, uniform contact with body tissue for consistent operation. The invention disclosed herein solves this problem.

This invention can be embodied in a wearable device for the arm with a plurality of close-fitting spectroscopic sensors comprising: an attachment member which spans at least a portion of the circumference of a person's arm; an enclosure which is part of and/or attached to the attachment member; a first spectroscopic sensor in the enclosure which projects a beam of light onto the arm surface at a first angle relative to the enclosure; and a second spectroscopic sensor in the enclosure which projects a beam of light onto the arm surface at a second angle relative to the enclosure, wherein the first angle differs from the second angle by at least 10 degrees. Data from the spectroscopic sensors is analyzed to measure a person's hydration levels, oxygen levels, glucose levels, or heart rate.

This invention can also be embodied in a wearable device for the arm with one or more close-fitting biometric sensors comprising: an attachment member which spans at least a portion of the circumference of a person's arm; an enclosure which is part of and/or attached to the attachment member; an elastic member filled with a fluid, gel, or gas which is attached to and/or part of the enclosure; and one or more biometric sensors which record biometric data concerning the person's arm tissue, wherein these one or more biometric sensors are attached to a circumference-center-facing wall of the elastic member. A biometric sensor can be a spectroscopic sensor which measures the spectrum of light energy reflected from and/or absorbed by tissue of the person's arm. Alternatively, a biometric sensor can be an electromagnetic energy sensor which measures parameters and/or patterns of electromagnetic energy passing through and/or emitted by tissue of the person's arm. In an example, measured parameters and/or patterns of electromagnetic energy can be selected from the group consisting of: impedance, resistance, conductivity, permittivity, and electromagnetic wave pattern. Data from the one or more sensors are analyzed to measure a person's hydration levels, oxygen levels, glucose levels, or heart rate.

This invention can also be embodied in a wearable device for the arm with a close-fitting biometric sensor comprising: a circumferentially-undulating attachment member which spans at least a portion of the circumference of a person's arm; and a plurality of biometric sensors which collect data concerning arm tissue, wherein each biometric sensor is located at the proximal portion of an undulation, and wherein the proximal portion of an undulation is the portion of an undulating wave which is closest to the circumferential center of the device. Data from the one or more sensors are analyzed to measure a person's hydration levels, oxygen levels, glucose levels, or heart rate.

INTRODUCTION TO THE FIGURES

FIG. 46 shows an arm-worn device with biometric sensors and a band with a side buckle or clasp.

FIG. 47 shows an arm-worn device with biometric sensors and a "clam-shell" design band.

FIG. 48 shows an arm-worn device with biometric sensors, a "clam-shell" design band, and a compressible member.

DETAILED DESCRIPTION OF THE FIGURES

Figure 1:
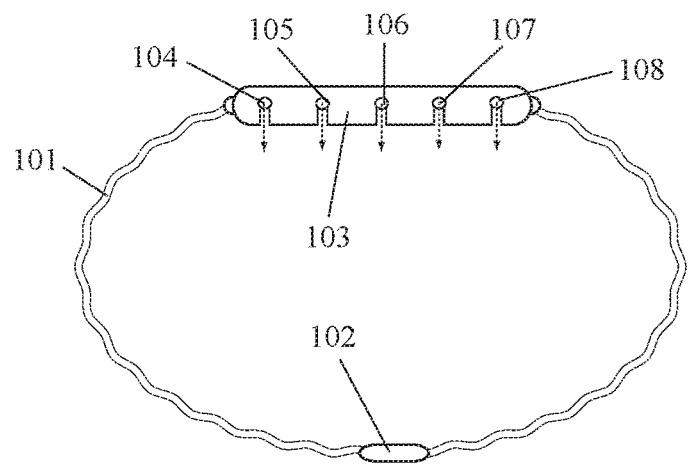
FIG. 1 shows an arm-worn device with biometric sensors at different circumferential locations.

FIG. 1 shows an example of a wearable device for the arm with a plurality of close-fitting biometric sensors. This figure shows the device from a side perspective, as it would appear encircling a lateral cross-section of a person's wrist (or other portion of the person's arm). Described generally, the example shown in FIG. 1 is an arcuate wrist-worn device with a circumferentially-distributed array of biometric sensors. A series of circumference-center-facing biometric sensors are distributed along different locations on a portion of the circumference of the device. In this example, the array of sensors is distributed along the circumference-center-facing surface of an enclosure which is on the anterior (upper) portion of the device. In another example, an array of sensors can be distributed along the circumference-center-facing surface of a band or strap.

Having a circumferentially-distributed array of sensors allows a wearable device to record biometric measurements from different locations along the circumference of a person's wrist. This can help to find the best location on a person's wrist from which to most-accurately record biometric measurements. Having a circumferentially-distributed array of sensors can also enable a device to record biometric measurements from substantially the same location on a person's wrist, even if the device is unintentionally slid, shifted, and/or partially-rotated around the person's wrist. A different primary sensor can be selected to record data when the device slides, shifts, and/or rotates. This can help to reduce biometric measurement errors when the device is slid, shifted, and/or partially-rotated around a person's wrist.

More specifically, the example shown in FIG. 1 is a wearable device for the arm with a plurality of close-fitting biometric sensors comprising: (a) an attachment member, such as a strap or band, which is configured to span at least a portion of the circumference of a person's arm; (b) an enclosure which is part of (or attached to) the attachment member; (c) a first biometric sensor at a first location in the enclosure which is configured to record biometric data concerning the person's arm tissue; and (d) a second biometric sensor at a second location in the enclosure which is configured to record biometric data concerning the person's arm tissue, wherein the distance along the circumference of the device from the first location to second location is at least a quarter inch.

In an example, an attachment member can be a strap, band, bracelet, ring, armlet, cuff, or sleeve. In an example, an attachment member can be attached to a person's arm by connecting two ends of the attachment member with a clasp, clip, buckle, hook, pin, plug, or hook-and-eye mechanism. In an example, the attachment member can be attached to a person's arm by stretching and sliding it over the person's hand onto the arm. In an example, the attachment member can be attached to a person's arm by applying force to pull two ends apart to slip the member over the arm, wherein the two ends retract back towards each other when the force is removed.

In an example, the circumference-center-facing surface of an enclosure can be substantially flat. In an example, the circumference-center-facing surface of an enclosure can be curved. In an example, a plurality of sensors can be housed within a single enclosure. In another example, different sensors can be housed in different enclosures. In another example, sensors can be located along the circumference-center-facing surface of an attachment member. In an example, there can be a display screen on the outward-facing surface of an enclosure.

In an example, first and second biometric sensors can be spectroscopic sensors which are each configured to measure the spectrum of light energy reflected from (and/or absorbed by) tissue of the person's arm. In an example, first and second biometric sensors can be electromagnetic energy sensors which are each configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

With respect to specific components, the example shown in FIG. 1 includes: strap (or band) 101, strap (or band) connector 102, enclosure 103, and spectroscopic sensors 104, 105, 106, 107, and 108. In an example, this device can further comprise one or more components selected from the group consisting of: a data processor; a battery and/or energy harvesting unit; a display screen; a data transmitter; and a data receiver. In an example, relevant embodiment variations discussed elsewhere in this or a priority-linked disclosure can also apply to this example.

Figure 2:
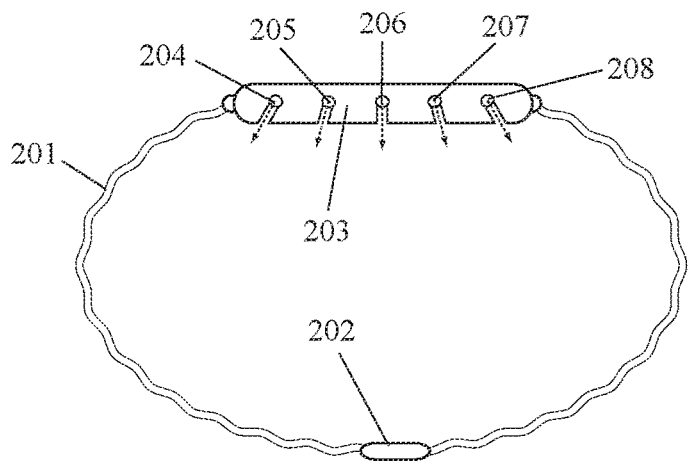
FIG. 2 shows an arm-worn device with spectroscopic sensors projecting light at different angles.

FIG. 2 shows another example of a wearable device for the arm with a plurality of close-fitting biometric sensors. This figure shows the device from a side perspective, as it would appear encircling a lateral cross-section of a person's wrist (or other portion of the person's arm).

The example shown in FIG. 2 is like the one shown in FIG. 1 except that different sensors in the array of sensors direct light energy onto the surface of an arm at different angles relative to an enclosure. Having an array of sensors which direct light energy onto the surface of the arm at different angles relative to an enclosure can enable a device to record biometric measurements with substantially the same angle of incidence, even if the enclosure is tilted with respect to the surface of the person's wrist. A different primary sensor with a different angle of light projection can be selected to record data when the enclosure is tilted. For example, when an enclosure is parallel to the surface of the person's wrist, then a sensor with a 90-degree light projection angle (relative to the enclosure) can be selected so that light is projected onto the surface of the arm in a perpendicular manner. However, when the enclosure is tilted at a 20-degree angle relative to the surface of the person's wrist, then a sensor with a 70-degree angle (relative to the enclosure) can be selected so that light is again projected onto the surface of the arm in a perpendicular manner.

The example shown in FIG. 2 is a wearable device for the arm with a plurality of close-fitting biometric sensors comprising: (a) an attachment member, such as a strap or band, which is configured to span at least a portion of the circumference of a person's arm; (b) an enclosure which is part of (or attached to) the attachment member; (c) a first spectroscopic sensor in the enclosure which is configured to project a beam of light onto the arm surface at a first angle relative to the enclosure; and (d) a second spectroscopic sensor in the enclosure which is configured to project a beam of light onto the arm surface at a second angle relative to the enclosure, wherein the first angle differs from the second angle by at least 10 degrees.

In an example, an attachment member can be a strap, band, bracelet, ring, armlet, cuff, or sleeve. In an example, an attachment member can be attached to a person's arm by connecting two ends of the attachment member with a clasp, clip, buckle, hook, pin, plug, or hook-and-eye mechanism. In an example, the attachment member can be attached to a person's arm by stretching and sliding it over the person's hand onto the arm. In an example, the attachment member can be attached to a person's arm by applying force to pull two ends apart to slip the member over the arm, wherein the two ends retract back towards each other when the force is removed.

In an example, the circumference-center-facing surface of an enclosure can be substantially flat. In an example, the circumference-center-facing surface of an enclosure can be curved. In an example, a plurality of sensors can be housed within a single enclosure. In another example, different sensors can be housed in different enclosures. In another example, sensors can be located along the circumference-center-facing surface of an attachment member. In an example, there can be a display screen on the outward-facing surface of an enclosure.

With respect to specific components, the example shown in FIG. 2 includes: strap (or band) 201, strap (or band) connector 202, enclosure 203, and spectroscopic sensors 204, 205, 206, 207, and 208. In an example, this device can further comprise one or more components selected from the group consisting of: a data processor; a battery and/or energy harvesting unit; a display screen; a data transmitter; and a data receiver. In an example, relevant embodiment variations discussed elsewhere in this or a priority-linked disclosure can also apply to this example.

Figure 3:
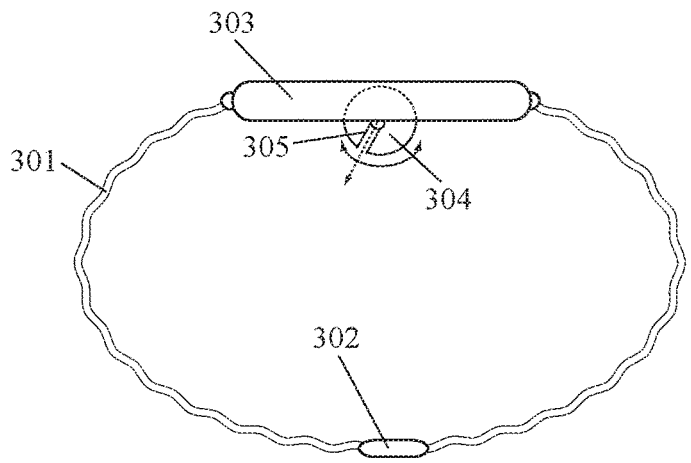
FIG. 3 shows an arm-worn device with a rotating spectroscopic sensor.

FIG. 3 shows an example of a wearable device for the arm with a close-fitting biometric sensor. This figure shows the device from a side perspective, as it would appear encircling a lateral cross-section of a person's wrist (or other portion of the person's arm).

Described generally, the example shown in FIG. 3 is an arcuate wrist-worn device with a rotating light-projecting spectroscopic sensor, wherein rotation of this sensor changes the angle at which it projects light onto the surface of a person's arm. In this example, the rotating light-projecting spectroscopic sensor is on the circumference-center-facing surface of an enclosure which is on the anterior (upper) portion of the device. In another example, such a sensor can be on the circumference-center-facing surface of a band or strap.

Having a rotating light-projecting spectroscopic sensor can enable a device to record biometric measurements with substantially the same angle of incidence, even if an enclosure is tilted with respect to the surface of the person's wrist. For example, when the enclosure is parallel to the surface of the person's wrist, then the rotating sensor is automatically rotated to project light at a 90-degree angle (relative to the enclosure) so that light is projected onto the surface of the arm in a perpendicular manner. However, when the enclosure is tilted at a 20-degree angle relative to the surface of the person's wrist, then the rotating sensor is automatically rotated to project light at a 70-degree angle (relative to the enclosure) so that light is again projected onto the surface of the arm in a perpendicular manner.

The example shown in FIG. 3 is a wearable device for the arm with a close-fitting biometric sensor comprising: (a) an attachment member, such as a strap or band, which is configured to span at least a portion of the circumference of a person's arm; (b) an enclosure which is part of (or attached to) the attachment member; and (c) a rotating light-projecting spectroscopic sensor, wherein this sensor can be rotated relative to the enclosure and wherein rotation of this sensor relative to the enclosure changes the angle at which the sensor projects light onto the surface of a person's arm.

In an example, an attachment member can be a strap, band, bracelet, ring, armlet, cuff, or sleeve. In an example, an attachment member can be attached to a person's arm by connecting two ends of the attachment member with a clasp, clip, buckle, hook, pin, plug, or hook-and-eye mechanism.

In an example, the attachment member can be attached to a person's arm by stretching and sliding it over the person's hand onto the arm. In an example, the attachment member can be attached to a person's arm by applying force to pull two ends apart to slip the member over the arm, wherein the two ends retract back towards each other when the force is removed.

In an example, the circumference-center-facing surface of an enclosure can be substantially flat. In an example, the circumference-center-facing surface of an enclosure can be curved. In an example, there can be a display screen on the outward-facing surface of an enclosure.

With respect to specific components, the example shown in FIG. 3 includes: strap (or band) 301, strap (or band) connector 302, enclosure 303, rotating member 304, and light-projecting spectroscopic sensor 305. In an example, this device can further comprise one or more components selected from the group consisting of: a data processor; a battery and/or energy harvesting unit; a display screen; a data transmitter; and a data receiver. In an example, relevant embodiment variations discussed elsewhere in this or a priority-linked disclosure can also apply to this example.

Figure 4:
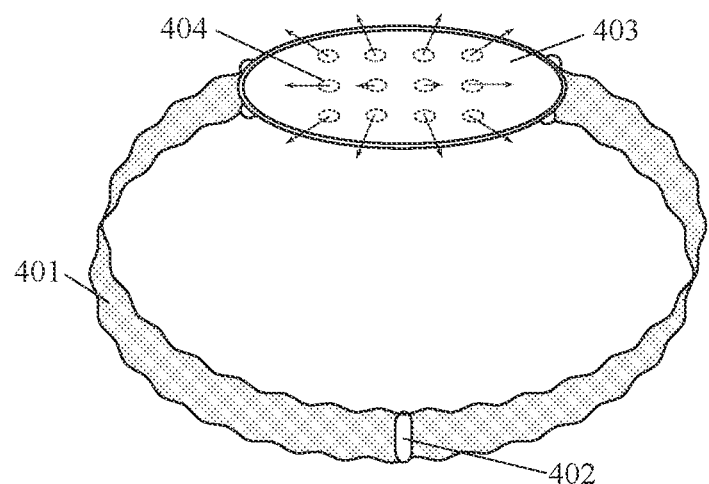
FIG. 4 shows an arm-worn device with a two-dimensional array of biometric sensors.

FIG. 4 shows another example of a wearable device for the arm with a plurality of close-fitting biometric sensors. This figure shows the device from a non-perpendicular lateral perspective, as it would appear encircling a lateral cross-section of a person's wrist (or other portion of the person's arm).

Described generally, the example shown in FIG. 4 is an arcuate wrist-worn device with a two-dimensional array of spectroscopic sensors. Sensors in this two-dimensional array differ in location circumferentially (they are at different locations around the circumference of the device) and laterally (they are at different locations along axes which are perpendicular to the circumference of the device). In this example, the two-dimensional sensor array is part of the circumference-center-facing surface of an enclosure which is on the anterior (upper) portion of the device. In another example, a two-dimensional sensor array can be on the circumference-center-facing surface of a band or strap.

Having a two-dimensional sensor array allows a wearable device to record biometric measurements from multiple locations on a person's wrist. This can help to find the best location on a person's wrist from which to most-accurately record biometric measurements. Having a two-dimensional sensor array can also enable a device to record biometric measurements from substantially the same location on a person's wrist even if the device is rotated around the person's wrist or slid up or down the person's arm. A different primary sensor can be automatically selected to record data when the device rotates or slides.

More specifically, the example shown in FIG. 4 is a wearable device for the arm with a plurality of close-fitting biometric sensors comprising: (a) an attachment member, such as a strap or band, which is configured to span at least a portion of the circumference of a person's arm; (b) an enclosure which is part of (or attached to) the attachment member; and (c) a two-dimensional sensor array which is part of the enclosure, wherein sensors in this two-dimensional array differ in location along a portion of the circumference of the device, and wherein sensors in this two-dimensional array differ in location along axes which are perpendicular to the circumference of the device.

In an example, an attachment member can be a strap, band, bracelet, ring, armlet, cuff, or sleeve. In an example, an attachment member can be attached to a person's arm by connecting two ends of the attachment member with a clasp, clip, buckle, hook, pin, plug, or hook-and-eye mechanism. In an example, the attachment member can be attached to a person's arm by stretching and sliding it over the person's hand onto the arm. In an example, the attachment member can be attached to a person's arm by applying force to pull two ends apart to slip the member over the arm, wherein the two ends retract back towards each other when the force is removed.

In an example, the circumference-center-facing surface of an enclosure can be substantially flat. In an example, the circumference-center-facing surface of an enclosure can be curved. In an example, there can be a display screen on the outward-facing surface of an enclosure.

In an example, sensors in a two-dimensional sensor array can be spectroscopic sensors which are each configured to measure the spectrum of light energy reflected from (and/or absorbed by) tissue of the person's arm. In an example, sensors in a two-dimensional sensor array can be electromagnetic energy sensors which are each configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

With respect to specific components, the example shown in FIG. 4 includes: a strap (or band) 401, a strap (or band) connector 402, an enclosure 403, and a two-dimensional spectroscopic sensor array which includes sensor 404. In an example, this device can further comprise one or more components selected from the group consisting of: a data processor; a battery and/or energy harvesting unit; a display screen; a data transmitter; and a data receiver. In an example, relevant embodiment variations discussed elsewhere in this or a priority-linked disclosure can also apply to this example.

Figure 5:
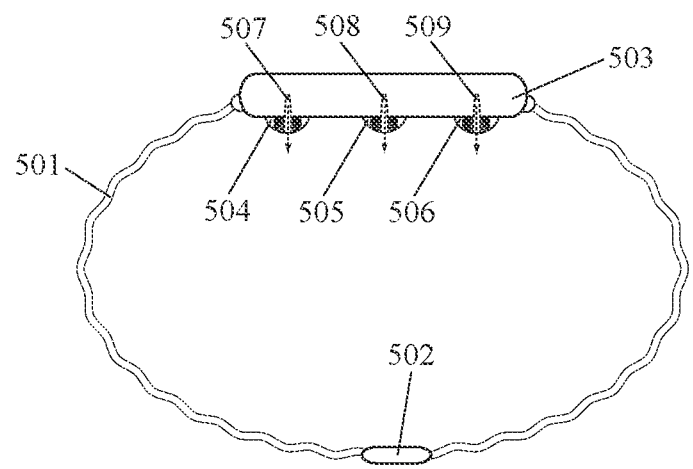
FIG. 5 shows an arm-worn device with biometric sensors which are individually pushed toward the arm surface from a flat enclosure.

FIG. 5 shows another example of a wearable device for the arm with a plurality of close-fitting biometric sensors. This figure shows the device from a side perspective, as it would appear encircling a lateral cross-section of a person's wrist (or other portion of the person's arm).

Described generally, the example shown in FIG. 5 is an arcuate wrist-worn device with a plurality of spectroscopic sensors, wherein each of these sensors is pushed toward the surface of an arm in order to stay in close contact with the surface of the arm even if the enclosure is shifted or tilted away from the surface of the arm. In this example, the spectroscopic sensors are on the circumference-center-facing portion of an enclosure. In this example, each of the spectroscopic sensors is pushed toward the surface of the arm by a spring mechanism. In another example, each of the spectroscopic sensors can be pushed toward the surface by a hydraulic mechanism, a pneumatic mechanism, or a microscale electromagnetic actuator.

More specifically, the example shown in FIG. 5 is a wearable device for the arm with a plurality of close-fitting biometric sensors comprising: (a) an attachment member, such as a strap or band, which is configured to span at least a portion of the circumference of a person's arm; (b) an enclosure which is part of (or attached to) the attachment member; and (c) a plurality of sensors which are part of the enclosure, wherein each sensor in this plurality of sensors is configured to be pushed toward the surface of the arm by a spring mechanism in order to keep the sensor in close contact with the surface of the arm.

In an example, an attachment member can be a strap, band, bracelet, ring, armlet, cuff, or sleeve. In an example, an attachment member can be attached to a person's arm by connecting two ends of the attachment member with a clasp, clip, buckle, hook, pin, plug, or hook-and-eye mechanism. In an example, the attachment member can be attached to a person's arm by stretching and sliding it over the person's hand onto the arm. In an example, the attachment member can be attached to a person's arm by applying force to pull two ends apart to slip the member over the arm, wherein the two ends retract back towards each other when the force is removed.

In an example, sensors of this device can be spectroscopic sensors which are each configured to measure the spectrum of light energy reflected from (and/or absorbed by) tissue of the person's arm. In an example, sensors of this device can be electromagnetic energy sensors which are each configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

With respect to specific components, the example shown in FIG. 5 includes: a strap (or band) 501; a strap (or band) connector 502; an enclosure 503; a plurality of spectroscopic sensors (507, 508, and 509); and a plurality of spring mechanisms (504, 505, and 506) which are configured to push the sensors inward toward the center of the device. In an example, this device can further comprise one or more components selected from the group consisting of: a data processor; a battery and/or energy harvesting unit; a display screen; a data transmitter; and a data receiver. In an example, relevant embodiment variations discussed elsewhere in this or a priority-linked disclosure can also apply to this example.

Figure 6:
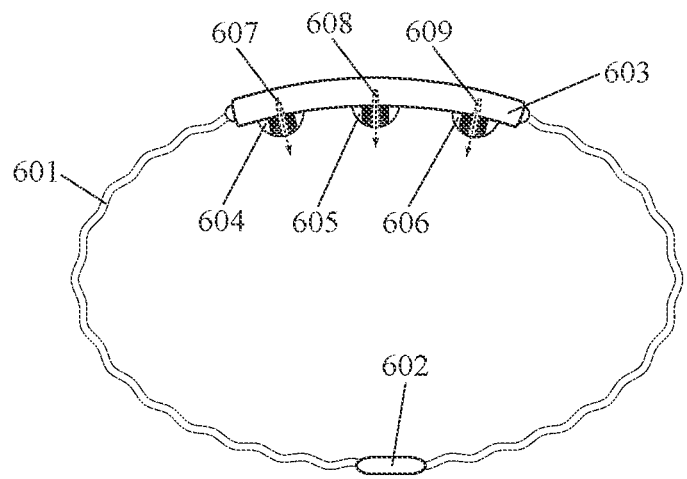
FIG. 6 shows an arm-worn device with biometric sensors which are individually pushed toward the arm surface from a curved enclosure.

FIG. 6 shows another example of a wearable device for the arm with a plurality of close-fitting biometric sensors. This figure shows the device from a side perspective, as it would appear encircling a lateral cross-section of a person's wrist (or other portion of the person's arm). The example shown in FIG. 6 is similar to the one shown in FIG. 5, except that the enclosure housing biometric sensors in FIG. 6 has a curved circumference-center-facing surface rather than a flat circumference-center-facing surface.

With respect to specific components, the example shown in FIG. 6 includes: a strap (or band) 601; a strap (or band) connector 602; an enclosure 603; a plurality of spectroscopic sensors (607, 608, and 609); and a plurality of spring mechanisms (604, 605, and 606) which are configured to push the sensors inward toward the center of the device. In an example, this device can further comprise one or more components selected from the group consisting of: a data processor; a battery and/or energy harvesting unit; a display screen; a data transmitter; and a data receiver. In an example, relevant embodiment variations discussed elsewhere in this or a priority-linked disclosure can also apply to this example.

Figure 7:
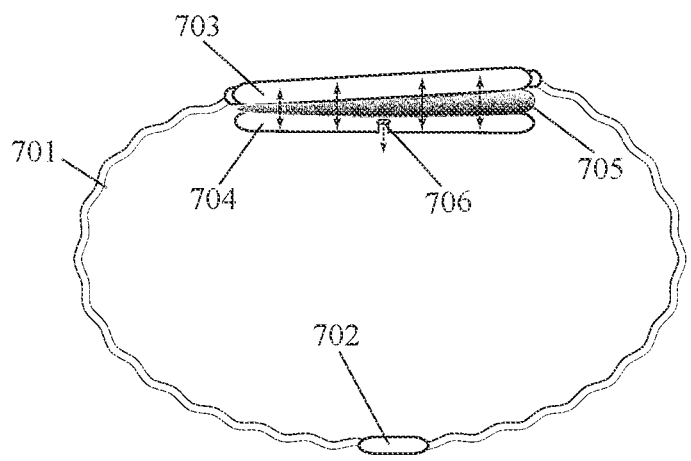
FIG. 7 shows an arm-worn device with biometric sensors on an enclosure which tilts on an inflated member.

FIG. 7 shows another example of a wearable device for the arm with one or more close-fitting biometric sensors. This figure shows the device from a side perspective, as it would appear encircling a lateral cross-section of a person's wrist (or other portion of the person's arm). Described generally, the example shown in FIG. 7 is an arcuate wrist-worn device with a biometric sensor which is located on a circumference-center-facing portion of an enclosure, wherein this circumference-center-facing portion tilts on a central inflated portion of the enclosure so that the sensor remains in close contact with the surface of a person's arm even if the device tilts with respect to the arm surface. In this example, an enclosure is positioned on the anterior (upper) portion of the device circumference. In this example, the enclosure has an outward-facing portion (which can include a display screen), a central inflated portion (which can be a balloon), and an inner-facing portion (which houses the biometric sensor). In an example, a central inflated portion can be sandwiched between a rigid outward-facing portion and a rigid circumference-center-facing portion. In an example, the circumference-center-facing portion can tilt with respect to the outward-facing portion as the device tilts with respect to the surface of the person's arm.

Having a biometric sensor located on a circumference-center-facing portion of an enclosure which tilts on a central inflated portion can help to keep the biometric sensor in close proximity to the surface of the person's arm and at substantially the same angle with respect to the surface of a person's arm. This can be particularly important for a spectroscopic sensor, wherein it is desirable to maintain the same projection angle (and/or reflection angle) of a beam of light which is directed toward (and/or reflected from) the surface of a person's arm.

More specifically, the example shown in FIG. 7 is a wearable device for the arm with one or more close-fitting biometric sensors comprising: (a) an attachment member, such as a strap or band, which is configured to span at least a portion of the circumference of a person's arm; (b) an enclosure which is part of (or attached to) the attachment member, wherein this enclosure further comprises a rigid outward facing portion, an inflated central portion, and a rigid circumference-center-facing portion, wherein the rigid circumference-center-facing portion tilts relative to the rigid outward facing portion; and (c) a biometric sensor in the circumference-center-facing portion which is configured to record biometric data concerning the person's arm tissue.

In an example, there can be a display screen on the outward-facing surface of the enclosure. In an example, the central portion of an enclosure can be filled with a liquid or gel rather than inflated with a gas. In an example, there can be more than one biometric sensor on the rigid circumference-center-facing portion. In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

With respect to specific components, the example shown in FIG. 7 includes: strap (or band) 701, strap (or band) connector 702, outward facing portion 703 of an enclosure, circumference-center-facing portion 704 of the enclosure, inflated central portion 705 of the enclosure, and a biometric sensor 706 on the circumference-center-facing portion of the enclosure. In an example, this device can further comprise one or more components selected from the group consisting of: a data processor; a battery and/or energy harvesting unit; a display screen; a data transmitter; and a data receiver. In an example, relevant embodiment variations discussed elsewhere in this or a priority-linked disclosure can also apply to this example.

Figure 8:
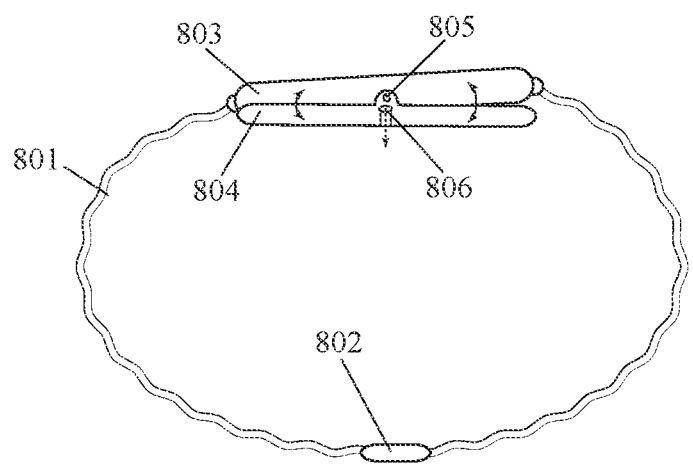
FIG. 8 shows an arm-worn device with biometric sensors on an enclosure which tilts on a rigid member.

FIG. 8 shows another example of a wearable device for the arm with one or more close-fitting biometric sensors. This figure shows the device from a side perspective, as it would appear encircling a lateral cross-section of a person's wrist (or other portion of the person's arm). Described generally, the example shown in FIG. 8 is an arcuate wrist-worn device with a biometric sensor which is located on a circumference-center-facing portion of an enclosure, wherein this circumference-center-facing portion pivots around an axis so that the sensor remains in close contact with the surface of a person's arm even if the device tilts with respect to the arm surface. In this example, an enclosure is positioned on the anterior (upper) portion of the device circumference. In this example, the enclosure has an outward-facing portion (which can include a display screen) and an inner-facing portion (which houses the biometric sensor).

In this example, a circumference-center-facing portion which houses a biometric sensor pivots around a central axis when the device tilts with respect to the surface of the person's arm. Having a biometric sensor located on a circumference-center-facing portion of an enclosure which pivots around an axis can help to keep the biometric sensor in close proximity to the surface of the person's arm and at substantially the same angle with respect to the surface of a person's arm. This can be particularly important for a spectroscopic sensor, wherein it is desirable to maintain the same projection angle (and/or reflection angle) of a beam of light which is directed toward (and/or reflected from) the surface of a person's arm.

More specifically, the example shown in FIG. 8 is a wearable device for the arm with one or more close-fitting biometric sensors comprising: (a) an attachment member, such as a strap or band, which is configured to span at least a portion of the circumference of a person's arm; (b) an enclosure which is part of (or attached to) the attachment member, wherein this enclosure further comprises an outward facing portion and a circumference-center-facing portion, wherein the rigid inward (or center) pivots around a central axis with respect to the outward facing portion; and (c) a biometric sensor in the circumference-center-facing portion which is configured to record biometric data concerning the person's arm tissue.

In this example, the central axis around which the circumference-center-facing portion pivots is perpendicular to the circumference of the device. In another example, the central axis around which the circumference-center-facing portion pivots can be parallel or tangential to the circumference of the device. In an example, there can be a display screen on the outward-facing surface of the enclosure. In an example, there can be more than one biometric sensor on the circumference-center-facing portion of the enclosure.

In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

With respect to specific components, the example shown in FIG. 8 includes: strap (or band) 801, strap (or band) connector 802, outward facing portion 803 of an enclosure, circumference-center-facing portion 804 of the enclosure, axis 805 around which circumference-center-facing portion 804 pivots; and a biometric sensor 806 on the circumference-center-facing portion of the enclosure. In an example, this device can further comprise one or more components selected from the group consisting of: a data processor; a battery and/or energy harvesting unit; a display screen; a data transmitter; and a data receiver. In an example, relevant embodiment variations discussed elsewhere in this or a priority-linked disclosure can also apply to this example.

Figure 9:
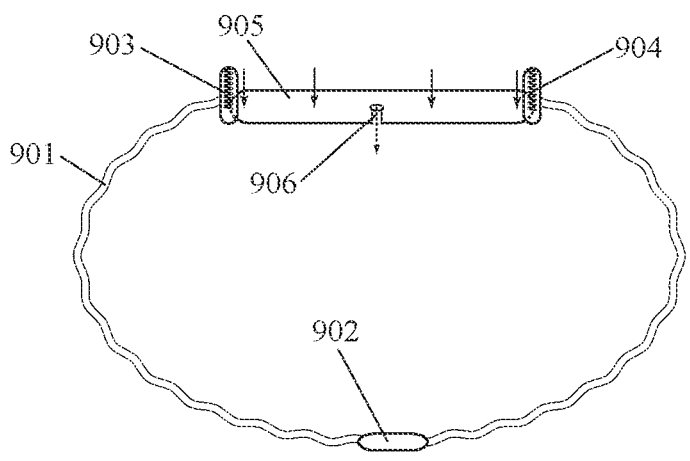
FIG. 9 shows an arm-worn device with biometric sensors on an enclosure which is pushed toward the arm surface by a spring mechanism.

FIG. 9 shows another example of a wearable device for the arm with one or more close-fitting biometric sensors. This figure shows the device from a side perspective, as it would appear encircling a lateral cross-section of a person's wrist (or other portion of the person's arm). Described generally, the example shown in FIG. 9 is a wrist-worn device with a biometric sensor located on an enclosure, wherein the enclosure is pushed toward the surface of a person's arm by spring mechanisms so that the sensor remains in close contact with the arm's surface even if the rest of the device shifts away from the arm's surface. In this example, the enclosure is on the anterior (upper) portion of the device circumference.

The example shown in FIG. 9 can also be expressed as a wearable device for the arm with one or more close-fitting biometric sensors comprising: (a) an attachment member, such as a strap or band, which is configured to span at least a portion of the circumference of a person's arm; (b) an enclosure which is part of (or attached to) the attachment member; (c) one or more spring mechanisms which push the enclosure inward toward the circumference center of the device; and (d) a biometric sensor in the enclosure which is configured to record biometric data concerning the person's arm tissue.

In this example, there are two spring mechanisms which push the enclosure inward toward the surface of a person's arm. In this example, these spring mechanisms are located at the places where the enclosure is connected to a strap or band. In an example, there can be a display screen on the outward-facing surface of the enclosure. In an example, there can be more than one biometric sensor on the circumference-center-facing portion of the enclosure. In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

With respect to specific components, the example shown in FIG. 9 includes: strap (or band) 901, strap (or band) connector 902, first spring mechanism 903, second spring mechanism 904, enclosure 905 which is pushed inward (toward the circumference center of the device) by spring mechanisms 903 and 904, and biometric sensor 906. In an example, this device can further comprise one or more components selected from the group consisting of: a data processor; a battery and/or energy harvesting unit; a display screen; a data transmitter; and a data receiver. In an example, relevant embodiment variations discussed elsewhere in this or a priority-linked disclosure can also apply to this example.

Figure 10:
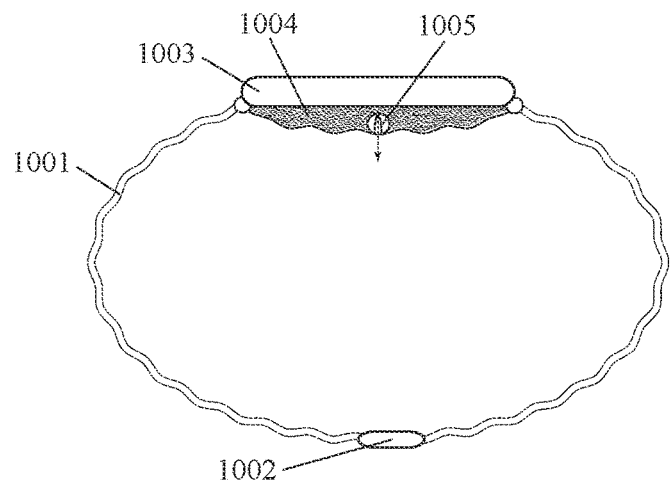
FIG. 10 shows an arm-worn device with a biometric sensor which is pushed toward the arm surface by an inflated member.

FIG. 10 shows another example of a wearable device for the arm with one or more close-fitting biometric sensors. This figure shows the device from a side perspective, as it would appear encircling a lateral cross-section of a person's wrist (or other portion of the person's arm). Described generally, this example is a wrist-worn device with an elastic member (such as a balloon) that is filled with a fluid, gel, or gas and a biometric sensor which is attached to the circumference-center-facing wall of this elastic member. Having a biometric sensor attached to the circumference-center-facing wall of an elastic member can help to keep the sensor in close contact with the surface of a person's arm, even if other components of the device are shifted or tilted away from the arm's surface. In an example, an elastic member can be part of an enclosure which is attached to an arm by a strap. In an example, such an enclosure can be positioned on the anterior (upper) portion of the device circumference.

The example shown in FIG. 10 can also be expressed as a wearable device for the arm with one or more close-fitting biometric sensors comprising: (a) an attachment member, such as a strap or band, which is configured to span at least a portion of the circumference of a person's arm; (b) an enclosure which is part of (or attached to) the attachment member; (c) an elastic member filled with a fluid, gel, or gas which is attached to (or part of) the enclosure; and (d) a biometric sensor which is configured to record biometric data concerning the person's arm tissue, wherein this sensor is attached to a circumference-center-facing wall of the elastic member.

In an example, there can be a display screen on the outward facing surface of an enclosure. In an example, there can be more than one biometric sensor on the circumference-center-facing wall of an elastic member. In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

With respect to specific components, the example shown in FIG. 10 includes: strap (or band) 1001; strap (or band) connector 1002; enclosure 1003; elastic member 1004 which is filled with a fluid, gel, or gas; and biometric sensor 1005 which is attached to the circumference-center-facing wall of the elastic member. In an example, this device can further comprise one or more components selected from the group consisting of: a data processor; a battery and/or energy harvesting unit; a display screen; a data transmitter; and a data receiver. In an example, relevant embodiment variations discussed elsewhere in this or a priority-linked disclosure can also apply to this example.

Figure 11:
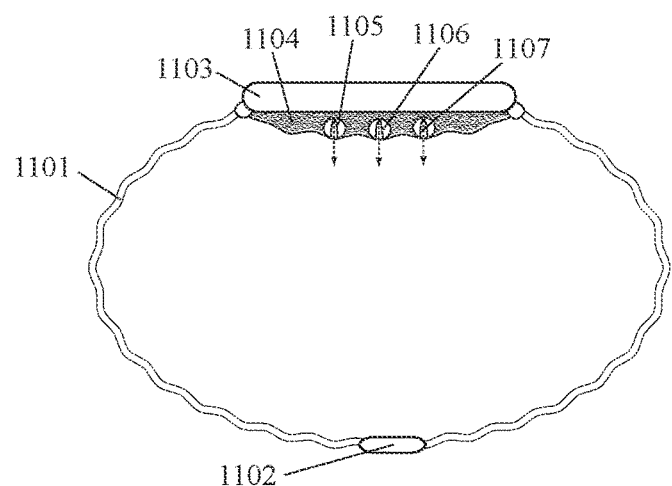
FIG. 11 shows an arm-worn device with biometric sensors which are pushed toward the arm surface by an inflated member.

FIG. 11 shows another example of a wearable device for the arm with one or more close-fitting biometric sensors. This figure shows the device from a side perspective, as it would appear encircling a lateral cross-section of a person's wrist (or other portion of the person's arm). The example shown in FIG. 11 is like the one shown in FIG. 10, except that in FIG. 11 there are multiple biometric sensors on the circumference-center-facing wall of an elastic member. In FIG. 11, there are three biometric sensors.

With respect to specific components, the example shown in FIG. 11 includes: strap (or band) 1101; strap (or band) connector 1102; enclosure 1103; elastic member 1104 which is filled with a fluid, gel, or gas; and biometric sensors 1105, 1106, and 1107 which are attached to the circumference-center-facing wall of the elastic member. In an example, this device can further comprise one or more components selected from the group consisting of: a data processor; a battery and/or energy harvesting unit; a display screen; a data transmitter; and a data receiver. In an example, relevant embodiment variations discussed elsewhere in this or a priority-linked disclosure can also apply to this example.

Figure 12:
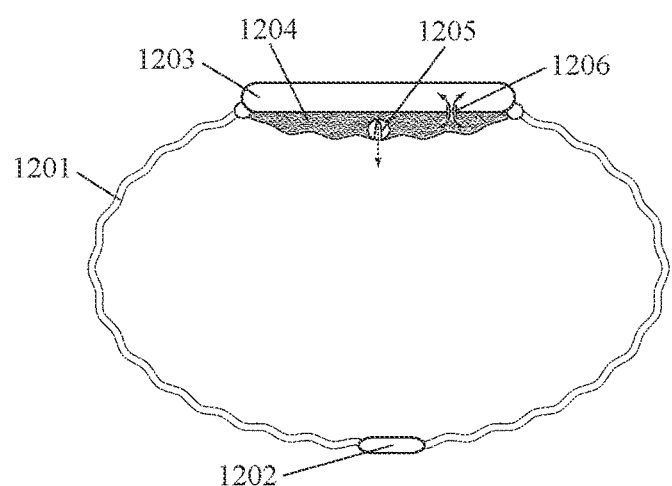
FIG. 12 shows an arm-worn device with a biometric sensor which is pushed toward the arm surface by an adjustable-pressure inflated member.

FIG. 12 shows another example of a wearable device for the arm with one or more close-fitting biometric sensors. This figure shows the device from a side perspective, as it would appear encircling a lateral cross-section of a person's wrist (or other portion of the person's arm). The example shown in FIG. 12 is like the one shown in FIG. 10, except that in FIG. 12 there is also a micropump which can pump fluid, gel, or gas into (or out of) the elastic member. This enables (automatic) adjustment of the size and/or internal pressure of the elastic member in order to better maintain proximity of the sensor to the surface of the person's arm.

With respect to specific components, the example shown in FIG. 12 includes: strap (or band) 1201; strap (or band) connector 1202; enclosure 1203; elastic member 1204 which is filled with a fluid, gel, or gas; biometric sensor 1205 which is attached to the circumference-center-facing wall of the elastic member; and micropump 1206 which pumps fluid, gel, or gas into (or out of) the elastic member. In an example, this device can further comprise one or more components selected from the group consisting of: a data processor; a battery and/or energy harvesting unit; a display screen; a data transmitter; and a data receiver. In an example, relevant embodiment variations discussed elsewhere in this or a priority-linked disclosure can also apply to this example.

Figure 13:
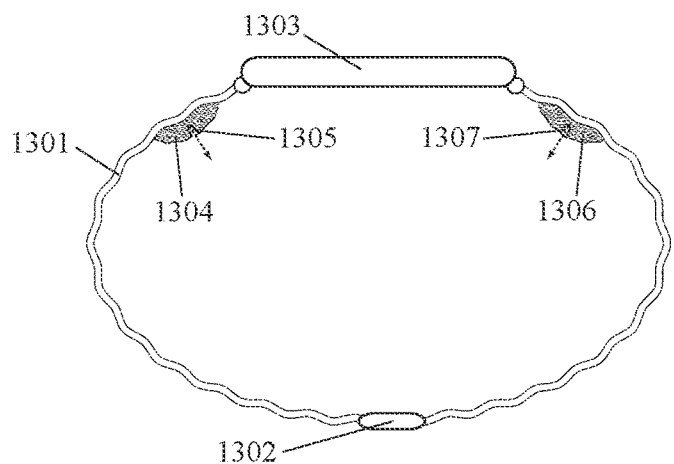
FIG. 13 shows an arm-worn device with biometric sensors which are pushed toward the arm surface by a plurality of inflated members.

FIG. 13 shows another example of a wearable device for the arm with one or more close-fitting biometric sensors. This figure shows the device from a side perspective, as it would appear encircling a lateral cross-section of a person's wrist (or other portion of the person's arm). This wrist-worn device comprises: an attachment member which is configured to span at least a portion of the circumference of a person's arm; one or more elastic members filled with a flowable substance, wherein these elastic members are part of (or attached to) the circumference-center-facing surface of the attachment member; and one or more biometric sensors, wherein each sensor is part of (or attached to) a circumference-center-facing wall of an elastic member.

The design of this device keeps biometric sensors close to the surface of a person's arm, even if portions of the device shift away from the surface of the person's arm. The interiors of the elastic members on which these sensors are located are under modest pressure so that these elastic members expand when they are moved away from the arm surface and these elastic members are compressed when they are moved toward the arm surface.

In an example, an attachment member can be a strap, band, bracelet, ring, armlet, cuff, or sleeve. In an example, an attachment member can be attached to a person's arm by connecting two ends of the attachment member with a clasp, clip, buckle, hook, pin, plug, or hook-and-eye mechanism. In an example, an attachment member can be attached to a person's arm by stretching it circumferentially and sliding it over the person's hand onto the arm. In an example, an attachment member can be attached to a person's arm by applying force to pull two ends of the member apart in order to slip the member over the arm; the two ends then retract back towards each other when device is on the arm and the force is removed.

In an example, an elastic member can be a balloon or other elastic substance-filled compartment. In an example, the flowable substance inside an elastic member can be a fluid, gel, or gas. In this example, there are two elastic members on the attachment member. In this example, the elastic members are symmetrically located with respect to a central cross-section of the device. In an example, there can be a plurality of elastic members (with attached biometric sensors) which are distributed around the circumference of an attachment member and/or the device. In this example, a device can also include an enclosure which further comprises a display screen.

In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

With respect to specific components, the example shown in FIG. 13 includes: band 1301; band connector 1302; enclosure 1303; first elastic member 1304 which is filled with a fluid, gel, or gas; first biometric sensor 1305 which is attached to the circumference-center-facing wall of the first elastic member; second elastic member 1306 which is filled with a fluid, gel, or gas; and second biometric sensor 1307 which is attached to the circumference-center-facing wall of the second elastic member. In an example, this device can further comprise one or more components selected from the group consisting of: a data processor; a battery and/or energy harvesting unit; a display screen; a data transmitter; and a data receiver. In an example, relevant embodiment variations discussed elsewhere in this or a priority-linked disclosure can also apply to this example.

Figure 14:
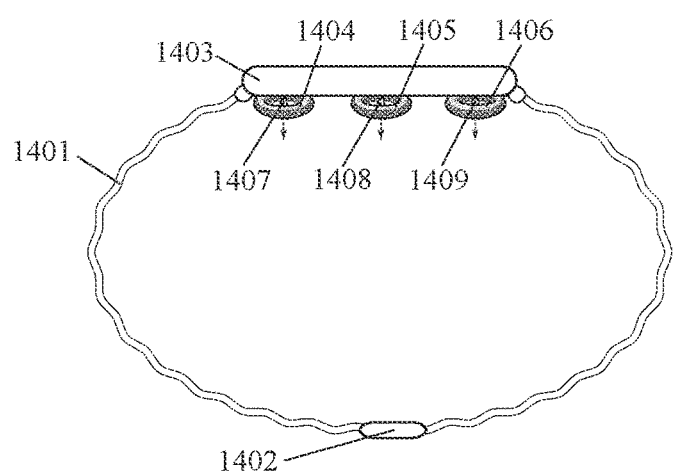
FIG. 14 shows an arm-worn device with biometric sensors which are pushed toward the arm surface by a plurality of toroidal inflated members.

FIG. 14 shows another example of a wearable device for the arm with one or more close-fitting biometric sensors. This figure shows the device from a side perspective, as it would appear encircling a lateral cross-section of a person's wrist (or other portion of the person's arm). This wrist-worn device comprises: (a) an attachment member which is configured to span at least a portion of the circumference of a person's arm; (b) an enclosure which is part of (or attached to) the attachment member; (c) one or more torus-shaped elastic members filled with a flowable substance, wherein these elastic members are part of (or attached to) the enclosure; and (d) one or more biometric sensors, wherein each sensor is located in the central hole of a torus-shaped elastic member.

In an example, an attachment member can be a strap, band, bracelet, ring, armlet, cuff, or sleeve. In an example, an enclosure can further comprise a display screen on its outer surface. In an example, a torus-shaped elastic member can be a balloon which is filled with a fluid, gel, or gas. In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

With respect to specific components, the example shown in FIG. 14 includes: band 1401; band connector 1402; enclosure 1403; torus-shaped elastic members 1404, 1405, and 1406; and biometric sensors 1407, 1408, and 1409 which are each located in the central opening (or hole) of a torus-shaped elastic member. In an example, this device can further comprise one or more components selected from the group consisting of: a data processor; a battery and/or energy harvesting unit; a display screen; a data transmitter; and a data receiver. In an example, relevant embodiment variations discussed elsewhere in this or a priority-linked disclosure can also apply to this example.

Figure 15:
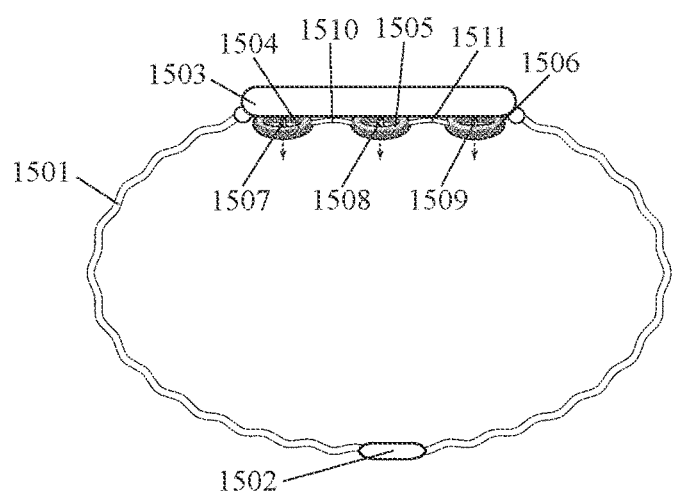
FIG. 15 shows an arm-worn device with biometric sensors which are pushed toward the arm surface by a plurality of inter-connected toroidal inflated members.

FIG. 15 shows another example of a wearable device for the arm with one or more close-fitting biometric sensors. This figure shows the device from a side perspective, as it would appear encircling a lateral cross-section of a person's wrist (or other portion of the person's arm). The example in FIG. 15 like the one shown in FIG. 14, except that the example in FIG. 15 also includes channels through which a fluid, gel, or gas can flow between the torus-shaped elastic members.

With respect to specific components, the example shown in FIG. 15 includes: band 1501; band connector 1502; enclosure 1503; torus-shaped elastic members 1504, 1505, and 1506; biometric sensors 1507, 1508, and 1509 which are each located in the central opening (or hole) of a torus-shaped elastic member; and channels 1510 and 1511 through which fluid, gel, or gas can flow between the torus-shaped elastic members. In an example, this device can further comprise one or more components selected from the group consisting of: a data processor; a battery and/or energy harvesting unit; a display screen; a data transmitter; and a data receiver. In an example, relevant embodiment variations discussed elsewhere in this or a priority-linked disclosure can also apply to this example.

Figure 16:
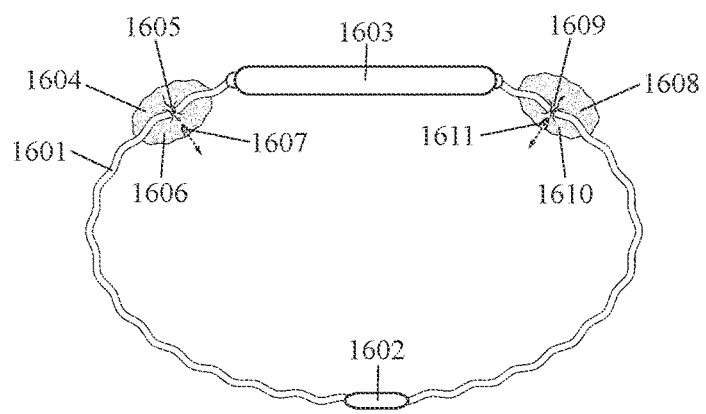
FIG. 16 shows an arm-worn device with biometric sensors which are pushed toward the arm surface by a plurality of adjustable-pressure inflated members.

FIG. 16 shows another example of a wearable device for the arm with one or more close-fitting biometric sensors. This figure shows the device from a side perspective, as it would appear encircling a lateral cross-section of a person's wrist (or other portion of the person's arm). The example in FIG. 16 like the one shown in FIG. 13, except that the example in FIG. 16 also includes elastic members on the outward-facing surface of the attachment member and channels through which fluid, gel, or gas can flow from circumference-center-facing elastic members to outward-facing elastic members, or vice versa.

This wrist-worn device comprises: (a) an attachment member which is configured to span at least a portion of the circumference of a person's arm; (b) at least one circumference-center-facing elastic member, wherein this member is filled with a flowable substance, and wherein this elastic member is part of (or attached to) the circumference-center-facing surface of the attachment member; (c) at least one outward-facing elastic member, wherein this member is filled with the flowable substance, and wherein this elastic member is part of (or attached to) the outward-facing surface of the attachment member; (d) a channel through which the flowable substance can flow between the circumference-center-facing elastic member and the outward-facing elastic member; and (e) a biometric sensor which is part of (or attached to) the circumference-center-facing wall of the circumference-center-facing elastic member.

In an example, an attachment member can be a strap, band, bracelet, ring, armlet, cuff, or sleeve. In an example, one or both of the elastic members can be a balloon or other elastic substance-filled compartment. In an example, the flowable substance inside an elastic member can be a fluid, gel, or gas. In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

With respect to specific components, the example shown in FIG. 16 includes: band 1601; band connector 1602; enclosure 1603; outward-facing elastic members 1604 and 1608, which are filled with a fluid, gel, or gas; circumference-center-facing elastic members 1606 and 1610, which are filled with the fluid, gel, or gas; channels 1605 and 1609 through which the fluid, gel, or gas can flow from an outward-facing elastic member to a circumference-center-facing elastic member, or vice versa; and biometric sensors 1607 and 1611 which are each attached to a circumference-center-facing wall of a circumference-center-facing elastic member. In an example, this device can further comprise one or more components selected from the group consisting of: a data processor; a battery and/or energy harvesting unit; a display screen; a data transmitter; and a data receiver. In an example, relevant embodiment variations discussed elsewhere in this or a priority-linked disclosure can also apply to this example.

Figure 17:
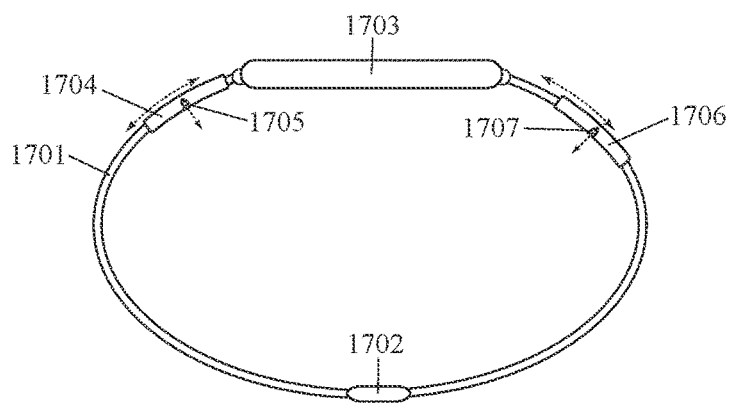
FIG. 17 shows an arm-worn device with biometric sensors on two circumferentially-sliding members.

FIG. 17 shows another example of a wearable device for the arm with one or more close-fitting biometric sensors. This figure shows the device from a side perspective, as it would appear encircling a lateral cross-section of a person's wrist (or other portion of the person's arm). A general description of the example in FIG. 17 can be expressed as a wrist-worn device with biometric sensors on circumferentially-sliding members, wherein these circumferentially-sliding members are slid along the circumference of the device in order to adjust the positions from which the biometric sensors measure data concerning arm tissue. Such moveable sensors enable a user to find the best positions around the circumference of the device from which to collect biometric data for a selected application.

This wrist-worn device comprises: (a) an attachment member which is configured to span at least a portion of the circumference of a person's arm; (b) at least one circumferentially-sliding member, wherein this member is slid along the circumference of the attachment member; and (c) at least one a biometric sensor which is part of (or attached to) the circumferentially-sliding member and collects data concerning arm tissue.

In an example, a sliding member can laterally-encircle an attachment member in order to keep the sliding member on the attachment member. In an example, the ends of a sliding member can curve around the sides of an attachment member in order to keep the sliding member on the attachment member. In an example, there can be a circumferential track on an attachment member into which a sliding member fits in order to keep the sliding member on the attachment member. In an example, a spring or other compressive mechanism on a sliding member can engage the attachment member in order to keep the sliding member on the attachment member. In an example, pressing on the top or sides of a sliding member frees it to slide along the attachment member and releasing this pressure causes the sliding member to stop sliding (and remain at a selected location on the attachment member). In an example, data from a biometric sensor on the sliding member can be analyzed in real time in order to identify the optimal location along the circumference of the attachment member from which to collect data.

In an example, an attachment member can be a strap, band, bracelet, ring, armlet, cuff, or sleeve. In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

With respect to specific components, the example shown in FIG. 17 includes: band 1701; band connector 1702; enclosure 1703; circumferentially-sliding members 1704 and 1706, wherein these members slide along the circumference of the band; and biometric sensors 1705 and 1707 which are each part of (or attached to) a circumferentially-sliding member. In an example, this device can further comprise one or more components selected from the group consisting of: a data processor; a battery and/or energy harvesting unit; a display screen; a data transmitter; and a data receiver. In an example, relevant embodiment variations discussed elsewhere in this or a priority-linked disclosure can also apply to this example.

Figure 18:
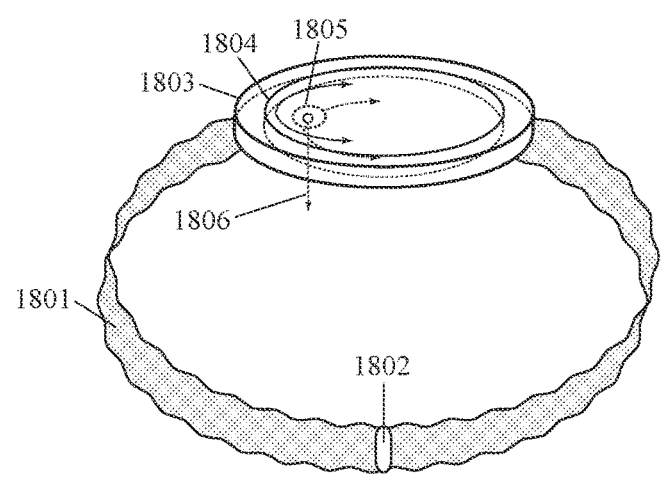
FIG. 18 shows an arm-worn device with biometric sensors on a non-threaded rotating member.

FIG. 18 shows another example of a wearable device for the arm with one or more close-fitting biometric sensors. This figure shows the device from a non-perpendicular lateral perspective, as it would appear encircling a lateral cross-section of a person's wrist (or other portion of the person's arm).

A general description of the example in FIG. 18 can be expressed as a wrist-worn device with a biometric sensor on a rotating member, wherein rotation of the rotating member moves the biometric sensor in a circular manner. In an example, the circular path in which a sensor moves is configured to be in a plane which is substantially tangential to the surface of a person's arm. In an example, a user can manually rotate the rotating member in order to find the optimal location from which to have the sensor collect biometric data. In an example, a device can automatically rotate the rotating member in order to find the optimal location from which to have the sensor collect biometric data. In an example, a device can automatically rotate the rotating member in order to maintain the optimal sensor location if the device is unintentionally shifted with respect to the arm's surface. In an example, a device can automatically rotate the rotating member in order to collect data from multiple locations for more comprehensive and/or accurate analysis.

In this example, a wearable device for the arm with one or more close-fitting biometric sensors comprises: (a) an attachment member which is configured to span at least a portion of the circumference of a person's arm; (b) an enclosure which is part of (or attached to) the attachment member; (c) a rotating member which is part of (or attached to) the enclosure; and (d) a biometric sensor which is part of (or attached to) the rotating member, wherein this biometric sensor is configured to collect data concerning a person's arm tissue, and wherein this biometric sensor moves in a circular path when the rotating member is rotated.

In an example, an attachment member can be a strap, band, bracelet, ring, armlet, cuff, or sleeve. In an example, a rotating member can be a circular member which fits into a hole or recess in an enclosure. In an example, a rotating member can be manually moved by a user in order to find the best location from which to have a sensor collect biometric data. In an example, a rotating member can be automatically moved by an actuator in the device in order to find the best location from which to have a sensor collect biometric data. In an example, a rotating member can be automatically moved by an actuator in the device in order to maintain the best sensor location when an enclosure is unintentionally shifted with respect to the arm's surface. In an example, a rotating member can be automatically moved by an actuator in order to collect data from multiple locations for more comprehensive and/or accurate analysis.

In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

With respect to specific components, the example shown in FIG. 18 includes: band 1801; band connector 1802; enclosure 1803; rotating member 1804 which is part of (or attached to) the enclosure; and biometric sensor 1805 which is part of (or attached to) the rotating member. In an example, this device can further comprise one or more components selected from the group consisting of: a data processor; a battery and/or energy harvesting unit; a display screen; a data transmitter; and a data receiver. In an example, relevant embodiment variations discussed elsewhere in this or a priority-linked disclosure can also apply to this example.

Figure 19:
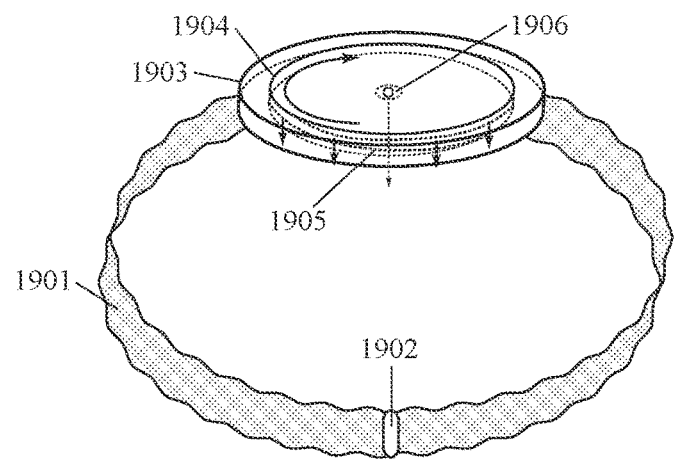
FIG. 19 shows an arm-worn device with biometric sensors on a threaded rotating member.

FIG. 19 shows another example of a wearable device for the arm with one or more close-fitting biometric sensors. This figure shows the device from a non-perpendicular lateral perspective, as it would appear encircling a lateral cross-section of a person's wrist (or other portion of the person's arm).

A general description of the example shown in FIG. 19 can be expressed as a wrist-worn device with a biometric sensor on a threaded rotating member, wherein rotation of the threaded rotating member adjusts the distance between the biometric sensor and the surface of a person's arm. In an example, a user can manually rotate the rotating member in order to find the optimal distance between the sensor and the arm's surface from which to have the sensor collect biometric data. In an example, a device can automatically (e.g. with an actuator) rotate the rotating member in order to find the optimal distance between the sensor and the arm's surface from which to have the sensor collect biometric data. In an example, a device can automatically (e.g. with an actuator) rotate the rotating member to maintain the optimal distance between a sensor and the arm's surface if the enclosure is unintentionally shifted with respect to the arm's surface.

In this example, a wearable device for the arm with one or more close-fitting biometric sensors comprises: (a) an attachment member which is configured to span at least a portion of the circumference of a person's arm; (b) an enclosure which is attached to (or part of) the attachment member; (c) a threaded rotating member which is attached to (or part of) the enclosure, wherein rotation of the threaded rotating member changes the distance between the threaded rotating member and the circumferential center of the device; and (d) a biometric sensor which is attached to (or part of) the threaded rotating member, wherein this biometric sensor is configured to collects data concerning a person's arm tissue, and wherein rotation of the threaded rotating member changes the distance between the biometric sensor and the circumferential center of the device. In an example, rotation of the threaded rotating member is also configured to change the distance between the biometric sensor and the surface of the person's arm.

In an example, an attachment member can be a strap, band, bracelet, ring, armlet, cuff, or sleeve. In an example, a threaded rotating member can have a spiral thread around its circumference which fits into a complementary spiral thread in a hole or recess in the enclosure. In an example, a threaded rotating member can be manually moved by a user in order to find the best distance between a sensor and the arm's surface from which to collect biometric data. In an example, a threaded rotating member can be automatically moved by an actuator in the device in order to find the best distance between a sensor and the arm's surface from which to collect biometric data. In an example, a threaded rotating member can be automatically moved by an actuator in the device in order to maintain the best distance between a sensor and the arm's surface when the location of an enclosure with respect to the arm's surface is unintentionally shifted.

In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

With respect to specific components, the example shown in FIG. 19 includes: band 1901; band connector 1902; enclosure 1903; threaded rotating member 1904 with spiral thread 1905 which is part of (or attached to) the enclosure; and biometric sensor 1906 which is part of (or attached to) the rotating member. In an example, this device can further comprise one or more components selected from the group consisting of: a data processor; a battery and/or energy harvesting unit; a display screen; a data transmitter; and a data receiver. In an example, relevant embodiment variations discussed elsewhere in this or a priority-linked disclosure can also apply to this example.

Figure 20:
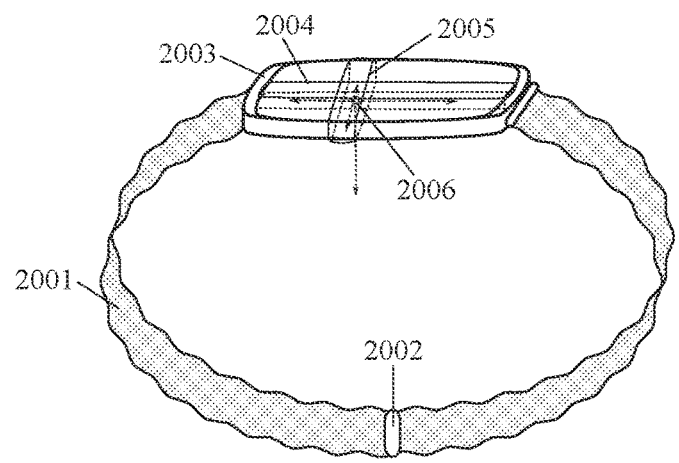
FIG. 20 shows an arm-worn device with biometric sensors which can be moved along an X and Y axes.

FIG. 20 shows another example of a wearable device for the arm with one or more close-fitting biometric sensors. This figure shows the device from a non-perpendicular lateral perspective, as it would appear encircling a lateral cross-section of a person's wrist (or other portion of the person's arm). The example shown in FIG. 20 can be described as a wrist-worn device with a biometric sensor, wherein the location of this sensor can be moved along an X axis and/or along a Y axis, wherein the X axis is substantially tangential to the circumference of the device, and wherein the Y axis is perpendicular to the X axis.

In an example, a user can manually move a sensor along these X and/or Y axes in order to find the optimal location from which to collect biometric data concerning arm tissue. In an example, the device can automatically move a sensor (e.g. with an actuator) along these X and/or Y axes in order to find the optimal location from which to collect biometric data concerning arm tissue. In an example, the device can automatically move a sensor (e.g. with an actuator) along these X and/or Y axes in order to keep the sensor at the optimal location even if the device is unintentionally shifted with respect to the arm's surface. In an example, the device can automatically move a sensor (e.g. with an actuator) along these X and/or Y axes in order to collect data from various locations for more comprehensive or accurate analysis.

In this example, a wearable device for the arm with one or more close-fitting biometric sensors comprises: (a) an attachment member which is configured to span at least a portion of the circumference of a person's arm; (b) an enclosure which is attached to (or part of) the attachment member; (c) a biometric sensor which is configured to collect data concerning arm tissue; (d) a first moving member whose movement moves the biometric sensor along an X axis, wherein this X axis is substantially tangential to the circumference of the device; and (e) a second moving member whose movement moves the biometric sensor along an Y axis, wherein this Y axis is perpendicular to the X axis.

In an example, an attachment member can be a strap, band, bracelet, ring, armlet, cuff, or sleeve. In an example, a biometric sensor can be attached to a circumference-center-facing portion of an enclosure. In an example, first and second moving members can be sliding members. In an example, a first moving member can be a strip on an enclosure which slides along the X axis. In an example, a second moving member can be a strip on an enclosure which slides along the Y axis. In another example, first and second moving members can be rotating members.

In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

With respect to specific components, the example shown in FIG. 20 includes: band 2001; band connector 2002; enclosure 2003; first sliding member 2004 which slides along an X axis, wherein the X axis is substantially tangential to the circumference of the device; second sliding member 2005 which slides along an Y axis, wherein the Y axis is substantially perpendicular to the X axis; and biometric sensor 2006 which is configured to collect data concerning arm tissue, wherein the X and Y coordinates of biometric sensor 2006 are changed by moving the first and second sliding members, respectively. In a variation on this example, both an enclosure and Y axis can be arcuate. In an example, this device can further comprise one or more components selected from the group consisting of: a data processor; a battery and/or energy harvesting unit; a display screen; a data transmitter; and a data receiver. In an example, relevant embodiment variations discussed elsewhere in this or a priority-linked disclosure can also apply to this example.

Figure 21:
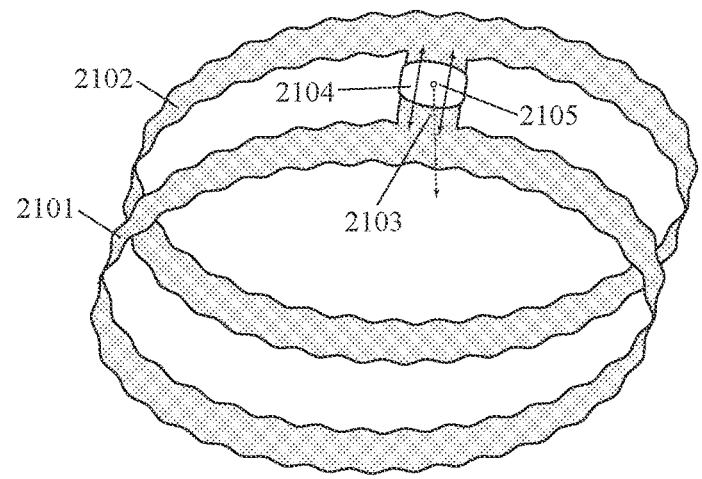
FIG. 21 shows an arm-worn device with two parallel bands and a biometric sensor which slides between them.

FIG. 21 shows another example of a wearable device for the arm with one or more close-fitting biometric sensors. This figure shows the device from a non-perpendicular lateral perspective, as it would appear encircling a lateral cross-section of a person's wrist (or other portion of the person's arm). The example shown in FIG. 21 can be described as a wrist-worn device with: two parallel bands which are connected to each other on the anterior (upper) surface of the wrist; and a biometric sensor which slides (back and forth) along the strip which connects the two bands.

In an example, a user can manually slide the biometric sensor (back and forth) along the strip connecting the two bands in order to find the optimal location from which to collect biometric data concerning arm tissue. In an example, the device can automatically slide the biometric sensor (back and forth) along the strip connecting the two bands in order to find the optimal location from which to collect biometric data concerning arm tissue. In an example, the device can automatically slide the biometric sensor (back and forth) along the strip connecting the two bands in order to collect data from different locations for more comprehensive or accurate analysis.

In this example, a wearable device for the arm with one or more close-fitting biometric sensors comprises: (a) two substantially-parallel bands which are each configured to span at least a portion of the circumference of a person's arm; (b) a connecting strip which is configured to connect the two bands to each other on the anterior (upper) surface of the arm; (c) a moving enclosure which slides (back and forth) along the connecting strip; and (d) a biometric sensor which is configured to collect data concerning arm tissue, wherein this biometric sensor is part of (or attached to) the moving enclosure.

In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

With respect to specific components, the example shown in FIG. 21 includes: first band 2101; second band 2102; connecting strip 2103 which connects the first and second bands; sliding enclosure 2104 which slides (back and forth) along the connecting strip; and biometric sensor 2105 which is configured to collect data concerning arm tissue, wherein this biometric sensor is part of (or attached to) the sliding enclosure. In an example, this device can further comprise one or more components selected from the group consisting of: a data processor; a battery and/or energy harvesting unit; a display screen; a data transmitter; and a data receiver. In an example, relevant embodiment variations discussed elsewhere in this or a priority-linked disclosure can also apply to this example.

Figure 22:
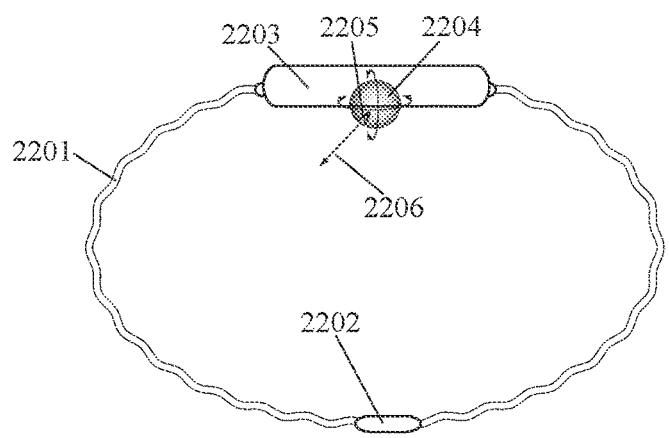
FIG. 22 shows an arm-worn device with a biometric sensor on a rotating ball.

FIG. 22 shows another example of a wearable device for the arm with one or more close-fitting biometric sensors. This figure shows the device from a side perspective, as it would appear encircling a lateral cross-section of a person's wrist (or other portion of the person's arm). Described generally, the example shown in FIG. 22 is an arcuate wrist-worn device with a light-projecting spectroscopic sensor on a rotating ball. Rotating the ball changes the angle at which the spectroscopic sensor projects light onto the surface of a person's arm. The ball can be rotated in different directions so that the range of possible projection beams comprises a conic or frustal shape in three-dimensional space. Having a light-projecting spectroscopic sensor on a rotating ball can enable a device to record biometric measurements with substantially the same angle of incidence, even if an enclosure is tilted with respect to the surface of the person's arm.

The example shown in FIG. 22 is a wearable device for the arm with a close-fitting biometric sensor comprising: (a) an attachment member, such as a strap or band, which is configured to span at least a portion of the circumference of a person's arm; (b) an enclosure which is part of (or attached to) the attachment member; (c) a rotating ball which is part of (or attached to) the enclosure; and (d) a light-projecting spectroscopic sensor which is part of (or attached to) the rotating ball.

In an example, an attachment member can be a strap, band, bracelet, ring, armlet, cuff, or sleeve. In an example, the circumference-center-facing surface of an enclosure can be substantially flat. In an example, the circumference-center-facing surface of an enclosure can be curved. In an example, there can be a display screen on the outward-facing surface of an enclosure. In an example, the rotating ball can fit into the enclosure like a ball-and-socket joint. In an example, the device can further comprise one or more actuators which move the rotating ball.

With respect to specific components, the example shown in FIG. 22 includes: strap 2201, strap connector 2202, enclosure 2203, rotating ball 2204, and spectroscopic sensor 2205 which emits beam of light 2206. In an example, this device can further comprise one or more components selected from the group consisting of: a data processor; a battery and/or energy harvesting unit; a display screen; a data transmitter; and a data receiver. In an example, relevant embodiment variations discussed elsewhere in this or a priority-linked disclosure can also apply to this example.

Figure 23:
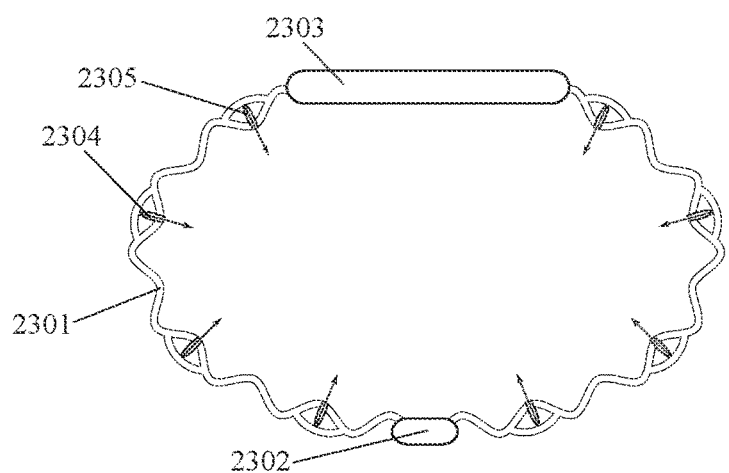
FIG. 23 shows a first arm-worn device with biometric sensors on a radially-undulating strap.

FIG. 23 shows another example of a wearable device for the arm with one or more close-fitting biometric sensors. This figure shows the device from a side perspective, as it would appear encircling a lateral cross-section of a person's wrist (or other portion of the person's arm). Described generally, the example shown in FIG. 23 is a wearable device for the arm with a flexible circumferentially-undulating band with biometric sensors on the proximal portions of undulating waves. A band with such a flexible circumferentially-undulating structure can help to keep a plurality of biometric sensors in close proximity to the surface of a person's arm. In an example, an attachment member can be a strap, band, bracelet, ring, or armlet. In an example, a circumferentially-undulating attachment member can have a repeating wave pattern. In an example, a circumferentially-undulating attachment member can have a sinusoidal wave pattern.

The example shown in FIG. 23 is a wearable device for the arm with a close-fitting biometric sensor comprising: (a) a circumferentially-undulating attachment member which is configured to span at least a portion of the circumference of a person's arm; and (b) a plurality of biometric sensors which collect data concerning arm tissue, wherein each biometric sensor is located at the proximal portion of an undulation, and wherein the proximal portion of an undulation is the portion of an undulating wave which is closest to the circumferential center of the device.

With respect to specific components, the example shown in FIG. 23 includes: circumferentially-undulating band 2301, band connector 2302, enclosure 2303, first biometric sensor 2304 at the proximal portion of a first wave in the circumferentially-undulating band, and second biometric sensor 2305 at the proximal portion of a second wave in the circumferentially-undulating band. In an example, this device can further comprise one or more components selected from the group consisting of: a data processor; a battery and/or energy harvesting unit; a display screen; a data transmitter; and a data receiver. In an example, relevant embodiment variations discussed elsewhere in this or a priority-linked disclosure can also apply to this example.

Figure 24:
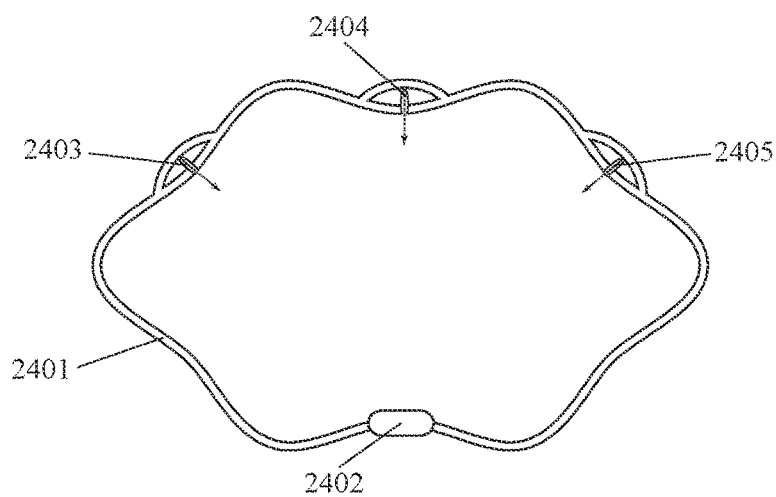
FIG. 24 shows a second arm-worn device with biometric sensors on a radially-undulating strap.

FIG. 24 shows another example of a wearable device for the arm with one or more close-fitting biometric sensors. This figure shows the device from a side perspective, as it would appear encircling a lateral cross-section of a person's wrist (or other portion of the person's arm). Described generally, the example shown in FIG. 24 is a wearable device for the arm with a flexible circumferentially-undulating band with six waves and biometric sensors on the proximal portions of some or all of these waves.

A band with a circumferentially-undulating structure can help to keep a plurality of biometric sensors in close proximity to the surface of a person's arm. Further, a band with six waves can engage the sides of a person's wrist with two symmetrically-opposite waves to resist rotational shifting better than a circular or oval band. This can help to reduce measurement errors caused by movement of biometric sensors. In an example, a circumferentially-undulating attachment member can be a strap, band, bracelet, ring, or armlet. In an example, a circumferentially-undulating attachment member can have a repeating wave pattern. In an example, a circumferentially-undulating attachment member can have a sinusoidal wave pattern.

The example shown in FIG. 24 is a wearable device for the arm with one or more close-fitting biometric sensors comprising: (a) a circumferentially-undulating attachment member with six waves which is configured to span the circumference of a person's arm; and (b) a plurality of biometric sensors which collect data concerning arm tissue, wherein each biometric sensor is located at the proximal portion of an undulation, and wherein the proximal portion of an undulation is the portion of an undulating wave which is closest to the circumferential center of the device.

With respect to specific components, the example shown in FIG. 24 includes: circumferentially-undulating band 2401 with six waves, band connector 2402, a first biometric sensor 2403 at the proximal portion of a first wave in the circumferentially-undulating band, a second biometric sensor 2405 at the proximal portion of a second wave in the circumferentially-undulating band, and a third biometric sensor 2406 at the proximal portion of a third wave in the circumferentially-undulating band. In an example, this device can further comprise one or more components selected from the group consisting of: a data processor; a battery and/or energy harvesting unit; a display screen; a data transmitter; and a data receiver. In an example, relevant embodiment variations discussed elsewhere in this or a priority-linked disclosure can also apply to this example.

Figure 25:
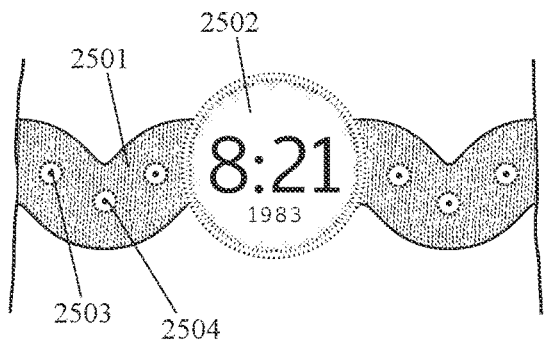
FIG. 25 shows an arm-worn device with biometric sensors on a laterally-undulating strap.

FIG. 25 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner. Described generally, the example shown in FIG. 25 is a wearable device for the arm with a laterally-undulating band and biometric sensors. Lateral undulations are waves which are substantially perpendicular to the plane containing the band circumference. In an example, a band can have sinusoidal lateral undulations.

The example shown in FIG. 25 is a wearable device for the arm with one or more close-fitting biometric sensors comprising: (a) a laterally-undulating attachment member which is configured to span at least a portion of the circumference of a person's arm, wherein lateral undulations are waves which are substantially perpendicular to the plane containing the circumference of the attachment member; and (b) one or more biometric sensors which collect data concerning arm tissue, wherein these biometric sensors are part of (or attached to) the laterally-undulating attachment member.

With respect to specific components, the example shown in FIG. 25 includes: laterally-undulating strap 2501; display screen 2502; and biometric sensors including 2503 and 2504. In an example, this device can further comprise one or more components selected from the group consisting of: a data processor; a battery and/or energy harvesting unit; a display screen; a data transmitter; and a data receiver. In an example, relevant embodiment variations discussed elsewhere in this or a priority-linked disclosure can also apply to this example.

Figure 26:
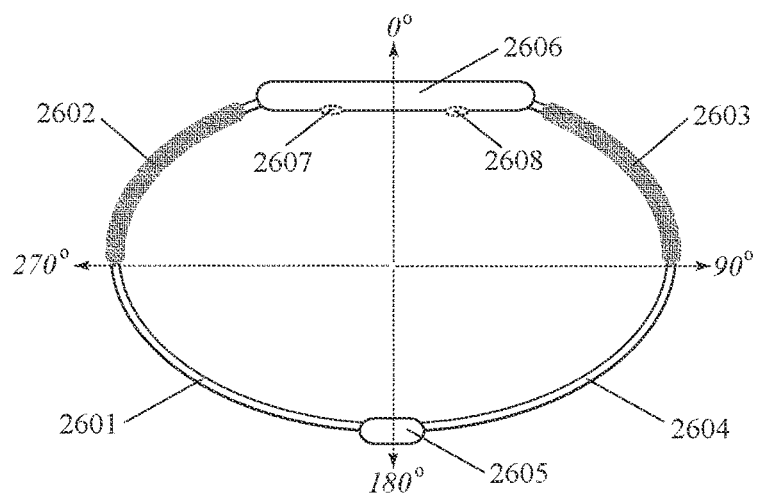
FIG. 26 shows a first arm-worn device with biometric sensors on a strap with elastic and inelastic portions.

FIG. 26 shows another example of a wearable device for the arm with one or more close-fitting biometric sensors. This figure shows the device from a side perspective, as it would appear encircling a lateral cross-section of a person's wrist (or other portion of the person's arm). Described generally, the example shown in FIG. 26 is a wearable device for an arm with one or more biometric sensors in an enclosure and an attachment member (such as a strap, band, bracelet, or cuff) which attaches the enclosure to the arm, wherein this attachment member has relatively-elastic portions connected to the enclosure and relatively-inelastic portions elsewhere. This structure can help to keep the enclosure and sensors fitting closely against the arm. This, in turn, can enable more-consistent collection of data concerning arm tissue.

In an example, the device in FIG. 26 can be specified as a wearable device for the arm with one or more close-fitting biometric sensors comprising: (a) an attachment member which is configured to span at least 60% of the circumference of a person's arm, wherein this attachment member further comprises—one or more elastic portions which are configured to span the anterior (upper) surface of a person's arm and one or more inelastic portions which are configured to span the posterior (lower) surface of the person's arm; (b) an enclosure which is connected to the elastic portions of the attachment member; and (c) one or more biometric sensors which collect data concerning arm tissue which are part of (or attached to) the enclosure.

In an alternative example, a wearable device for the arm with one or more close-fitting biometric sensors can comprise: (a) an attachment member which is configured to span at least 60% of the circumference of a person's arm, wherein this attachment member further comprises—one or more elastic portions which are configured to span the posterior (lower) surface of a person's arm and one or more inelastic portions which are configured to span the anterior (upper) surface of the person's arm; (b) an enclosure which is connected to the elastic portions of the attachment member; and (c) one or more biometric sensors which collect data concerning arm tissue which are part of (or attached to) the enclosure.

In an example, an elastic portion of an attachment member can be an elastic strap or band. In an example, an elastic portion of an attachment member can be made from elastic fabric. In an example, an elastic portion of an attachment member can have a first elasticity level, an inelastic portion of an attachment member can have a second elasticity level, and the first elasticity level can be greater than the second elasticity level. In an example, a first elastic portion of an attachment member can be directly connected to a first side of an enclosure and a second elastic portion of an attachment member can be directly connected to a second (opposite) side of the enclosure. In an example, a first elastic portion of an attachment member can be indirectly connected to a first side of an enclosure and a second elastic portion of an attachment member can be indirectly connected to a second (opposite) side of the enclosure.

In an example, the device in FIG. 26 can be specified as a wearable device for the arm with one or more close-fitting biometric sensors comprising: (a) an attachment member which is configured to span at least 60% of the circumference of a person's arm wherein this attachment member further comprises: two elastic portions which are configured to span a first portion of the circumference of a person's arm; and two inelastic portions which are configured to span a second portion of the circumference of the person's arm; (b) an enclosure which is connected between the two elastic portions; (c) a clip, buckle, clasp, pin, or hook-and-eye mechanism between the two inelastic portions; and d) one or more biometric sensors which collect data concerning arm tissue which are part of (or attached to) the enclosure.

In an example, the device in FIG. 26 can be specified as a wearable device for the arm with one or more close-fitting biometric sensors comprising: (a) an attachment member which is configured to span at least 60% of the circumference of a person's arm wherein this attachment member further comprises: two elastic portions of the attachment member which are configured to span a portion of the circumference of a person's arm; and one or more inelastic portions which comprise the remainder of the attachment member; (b) an enclosure which is connected between the two elastic portions; (c) one or more biometric sensors which collect data concerning arm tissue which are part of (or attached to) the enclosure.

In an example, a single elastic portion can be configured to span at least 10% of the circumference of a person's arm. In an example, a single elastic portion can be configured to span at least 10% of the circumference of an attachment member. In an example, a single inelastic portion can be configured to span at least 10% of the circumference of a person's arm. In an example, a single inelastic portion can be configured to span at least 10% of the circumference of an attachment member. In an example, two elastic portions can be configured to collectively span at least 20% of the circumference of a person's arm. In an example, two elastic portions can be configured to collectively span at least 20% of the circumference of an attachment member. In an example, two inelastic portions can be configured to collectively span at least 20% of the circumference of a person's arm. In an example, two inelastic portions can be configured to collectively span at least 20% of the circumference of an attachment member.

In an example, a first definition of polar (or compass) coordinates can be defined for a device relative to how the device is configured to be worn on a person's arm. A 0-degree position can be defined as the position on a device circumference which is configured to intersect the longitudinal mid-line of the anterior (upper) surface of the arm. A 180-degree position is diametrically opposite (through the circumferential center) the 0-degree position. A 90-degree position is (clockwise) midway between the 0-degree and 180-degree positions. A 270-degree position is diametrically opposite the 90-degree position.

Using this first definition of polar coordinates, the device in FIG. 26 can be specified as a wearable device for the arm with one or more close-fitting biometric sensors comprising: (a) an attachment member which is configured to span at least 60% of the circumference of a person's arm wherein this attachment member further comprises—an elastic first portion with a first level of elasticity which spans at least 35 degrees (clockwise) between the 270-degree and 0-degree positions; an elastic second portion with a second level of elasticity which spans at least 35 degrees (clockwise) between the 0-degree and 90-degree positions, an inelastic third portion with a third level of elasticity which spans at least 35 degrees (clockwise) between the 90-degree and 180-degree positions, an inelastic fourth portion with a fourth level of elasticity which spans at least 35 degrees (clockwise) between the 180-degree and 270-degree positions, and wherein each of the first and second elasticity levels is greater than each of the third and fourth elasticity levels; (b) an enclosure that is configured to be worn (clockwise) between the 270-degree and 90-degree positions; and (c) one or more biometric sensors which collect data concerning arm tissue which are part of (or attached to) the enclosure.

Using this first definition of polar coordinates, the device in FIG. 26 can also be specified as a wearable device for the arm with one or more close-fitting biometric sensors comprising: (a) an attachment member which is configured to span at least 60% of the circumference of a person's arm wherein this attachment member further comprises—an elastic first portion with a first level of elasticity which spans at least 35 degrees (clockwise) between the 270-degree and 0-degree positions; an elastic second portion with a second level of elasticity which spans at least 35 degrees (clockwise) between the 0-degree and 90-degree positions, an inelastic third portion with a third level of elasticity which spans at least 35 degrees (clockwise) between the 90-degree and 180-degree positions, an inelastic fourth portion with a fourth level of elasticity which spans at least 35 degrees (clockwise) between the 180-degree and 270-degree positions, and wherein each of the first and second elasticity levels is greater than each of the third and fourth elasticity levels; (b) an enclosure that is connected between the elastic first and second portions; and (c) one or more biometric sensors which collect data concerning arm tissue which are part of (or attached to) the enclosure.

Alternatively, a second definition of polar (or compass) coordinates can be defined for the circumference of such a device relative to the position of an enclosure. The 0-degree position can be defined as the position on the device circumference which intersects the (lateral) mid-line of the enclosure. The 180-degree position is diametrically opposite (through the circumferential center) the 0-degree position. The 90-degree position is clockwise midway between the 0-degree and 180-degree positions. The 270-degree position is diametrically opposite the 90-degree position.

Using this second definition of polar coordinates, the device in FIG. 26 can be specified as a wearable device for the arm with one or more close-fitting biometric sensors comprising: (a) an attachment member which is configured to span at least 60% of the circumference of a person's arm wherein this attachment member further comprises—an elastic first portion with a first level of elasticity which spans at least 35 degrees (clockwise) between the 270-degree and 0-degree positions; an elastic second portion with a second level of elasticity which spans at least 35 degrees (clockwise) between the 0-degree and 90-degree positions, an inelastic third portion with a third level of elasticity which spans at least 35 degrees (clockwise) between the 90-degree and 180-degree positions, an inelastic fourth portion with a fourth level of elasticity which spans at least 35 degrees (clockwise) between the 180-degree and 270-degree positions, and wherein each of the first and second elasticity levels is greater than each of the third and fourth elasticity levels; (b) an enclosure that is connected between the elastic first and second portions of the attachment member; and (c) one or more biometric sensors which collect data concerning arm tissue which are part of (or attached to) the enclosure.

In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

With respect to specific components, the example shown in FIG. 26 includes: inelastic portion 2601 of an attachment member; elastic portion 2602 of an attachment member; elastic portion 2603 of an attachment member; inelastic portion 2604 of an attachment member; attachment member connector 2605; enclosure 2606; and biometric sensors 2607 and 2608. In an example, this device can further comprise one or more components selected from the group consisting of: a data processor; a battery and/or energy harvesting unit; a display screen; a data transmitter; and a data receiver. In an example, relevant embodiment variations discussed elsewhere in this or a priority-linked disclosure can also apply to this example.

Figure 27:
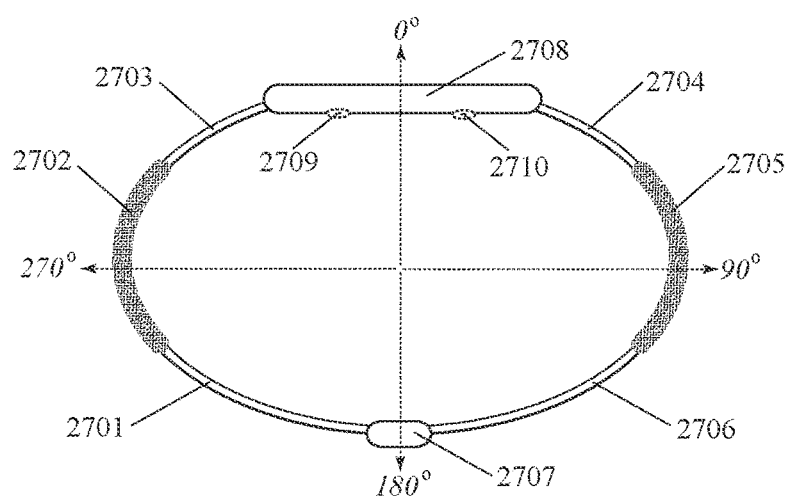
FIG. 27 shows a second arm-worn device with biometric sensors on a strap with elastic and inelastic portions.

FIG. 27 shows another example of a wearable device for the arm with one or more close-fitting biometric sensors. This figure shows the device from a side perspective, as it would appear encircling a lateral cross-section of a person's wrist (or other portion of the person's arm). Described generally, the example shown in FIG. 27 is a wearable device for the arm with one or more biometric sensors in an enclosure and an attachment member (such as a strap, band, bracelet, or cuff) which attaches the enclosure to the arm, wherein the attachment member is configured to have elastic portions spanning the lateral surfaces of the arm and inelastic portions spanning the anterior (upper) and posterior (lower) surfaces of the arm. This structure can help to keep the enclosure and sensors from rotating around the arm. This, in turn, can enable more-consistent collection of data concerning arm tissue.

In an example, the device in FIG. 27 can be specified as a wearable device for the arm with one or more close-fitting biometric sensors comprising: (a) an attachment member which is configured to span at least 60% of the circumference of a person's arm wherein this attachment member further comprises—one or more anterior inelastic portions which are configured to span the anterior (upper) surface of a person's arm, one or more posterior inelastic portions which are configured to span the posterior (lower) surface of a person's arm, and one or more elastic portions which connect the anterior and posterior inelastic portions; (b) an enclosure which is configured to be worn on the anterior (upper) portion of the arm; and (c) one or more biometric sensors which collect data concerning arm tissue which are part of (or attached to) the enclosure.

In another example, a wearable device for the arm with one or more close-fitting biometric sensors can comprise: (a) an attachment member which is configured to span at least 60% of the circumference of a person's arm wherein this attachment member further comprises—one or more anterior inelastic portions which are configured to span the anterior (upper) surface of a person's arm, one or more posterior inelastic portions which are configured to span the posterior (lower) surface of a person's arm, and one or more elastic portions which connect the anterior and posterior inelastic portions; (b) an enclosure which is configured to be worn on the posterior (lower) portion of the arm; and (c) one or more biometric sensors which collect data concerning arm tissue which are part of (or attached to) the enclosure.

In an example, a first inelastic portion of an attachment member can be connected to a first side of an enclosure and a second inelastic portion of an attachment member can be connected to a second side of the enclosure. In an example, an elastic portion can have a first level of elasticity, an inelastic portion can have a second level of elasticity, and the first level is greater than the second level. In an example, a single elastic portion can be configured to span at least 10% of the circumference of a person's arm. In an example, a single elastic portion can be configured to span at least 10% of the circumference of an attachment member. In an example, a single inelastic portion can be configured to span at least 10% of the circumference of a person's arm. In an example, a single inelastic portion can be configured to span at least 10% of the circumference of an attachment member.

In an example, polar (or compass) coordinates can be defined for a device relative to how the device is configured to be worn on a person's arm. A 0-degree position can be defined as the position on a device circumference which is configured to intersect the longitudinal mid-line of the anterior (upper) surface of the arm. A 180-degree position is diametrically opposite (through the circumferential center) the 0-degree position. A 90-degree position is clockwise midway between the 0-degree and 180-degree positions. A 270-degree position is diametrically opposite the 90-degree position.

In an example, the device in FIG. 27 can be specified as a wearable device for the arm with one or more close-fitting biometric sensors comprising: (a) an attachment member which is configured to span at least 60% of the circumference of a person's arm wherein this attachment member further comprises—a inelastic first portion with a first level of elasticity which spans at least 35 degrees (clockwise) between the 270-degree and 90-degree positions; an inelastic second portion with a second level of elasticity which spans at least 35 degrees (clockwise) between the 90-degree and 270-degree positions, an elastic third portion with a third level of elasticity which spans at least 35 degrees (clockwise) between the 180-degree and 0-degree positions, an elastic fourth portion with a fourth level of elasticity which spans at least 35 degrees (clockwise) between the 0-degree and 180-degree positions, and wherein each of the first and second elasticity levels is lower than each of the third and fourth elasticity levels; (b) an enclosure that is connected between the inelastic first portion and the inelastic second portion; and (c) one or more biometric sensors which collect data concerning arm tissue which are part of (or attached to) the enclosure.

In an alternative example, polar (or compass) coordinates can be defined for the circumference of such a device relative to the position of an enclosure on the device. The 0-degree position can be defined as the position on the device circumference which intersects the (lateral) mid-line of the enclosure. The 180-degree position is diametrically opposite (through the circumferential center) the 0-degree position. The 90-degree position is clockwise midway between the 0-degree and 180-degree positions. The 270-degree position is diametrically opposite the 90-degree position.

In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

With respect to specific components, the example shown in FIG. 27 includes: inelastic portion 2701 of an attachment member; elastic portion 2702 of an attachment member; inelastic portion 2703 of an attachment member; inelastic portion 2704 of an attachment member; elastic portion 2705 of an attachment member; inelastic portion 2706 of an attachment member; attachment member connector 2707; enclosure 2708; and biometric sensors 2709 and 2710. In an example, this device can further comprise one or more components selected from the group consisting of: a data processor; a battery and/or energy harvesting unit; a display screen; a data transmitter; and a data receiver. In an example, relevant embodiment variations discussed elsewhere in this or a priority-linked disclosure can also apply to this example.

Figure 28:
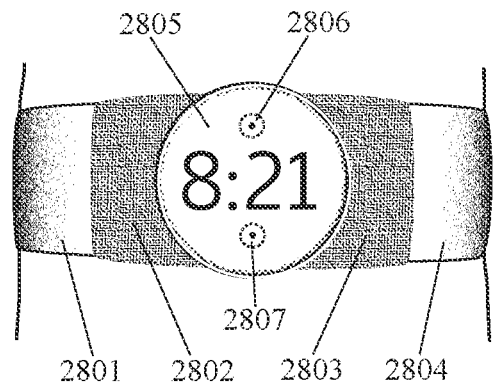
FIG. 28 shows an arm-worn device with biometric sensors on an enclosure which is connected to a strap by planoconvex elastic members.

FIG. 28 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner. This can be seen as a top-down view of a further-specified variation of the example that was shown from a side perspective in FIG. 26.

The example shown in FIG. 28 can be described generally as a wearable device for the arm with one or more biometric sensors in an enclosure and an attachment member (such as a band, strap, bracelet, or cuff) which holds the enclosure on a person's arm, wherein there are rectangular, rounded rectangular, or plano-concave elastic portions of the attachment member which are connected to the enclosure and wherein the rest of the attachment member is inelastic. Such a structure can help to keep the enclosure and sensors close against the arm surface. This, in turn, can enable more-consistent collection of data concerning arm tissue.

In an example, the device in FIG. 28 can be specified as a wearable device for the arm with one or more close-fitting biometric sensors comprising: (a) an attachment member which is configured to span at least 60% of the circumference of a person's arm, wherein this attachment member further comprises—a first elastic portion with a first elasticity level, a second elastic portion with a second elasticity level, and an inelastic portion with a third elasticity level, wherein the third elasticity level is less than each of the first and second elasticity levels; (b) an enclosure which is connected between the first and second elastic portions; and (c) one or more biometric sensors which collect data concerning arm tissue which are part of (or attached to) the enclosure.

In an example, the device in FIG. 28 can be specified as a wearable device for the arm with one or more close-fitting biometric sensors comprising: (a) an attachment member which is configured to span at least 60% of the circumference of a person's arm, wherein this attachment member further comprises—a first plano-concave elastic portion with a first elasticity level, a second plano-concave elastic portion with a second elasticity level, and an inelastic portion with a third elasticity level, wherein the third elasticity level is less than each of the first and second elasticity levels; (b) an enclosure which is connected between the first and second plano-concave elastic portions; and (c) one or more biometric sensors which collect data concerning arm tissue which are part of (or attached to) the enclosure.

In an example, the device in FIG. 28 can be specified as a wearable device for the arm with one or more close-fitting biometric sensors comprising: (a) an enclosure which is configured to be worn on a person's arm; (b) one or more biometric sensors which collect data concerning arm tissue which are part of (or attached to) the enclosure; (c) two elastic members which are attached to the enclosure, wherein these elastic members are configured to collectively span at least 20% of the circumference of the arm, and wherein these elastic attachment members have first and second elasticity levels, respectively; and (d) one or more inelastic members which are attached to the two elastic attachment members, wherein these inelastic members collectively span at least 40% of the circumference of the arm, and wherein these inelastic members have a third elasticity level which is less than each of the first and second elasticity levels.

In an example, an elastic member can have a shape which is selected from the group consisting of: rectangular; rounded rectangle; plano-concave; and section of a cylinder. In an example, the device in FIG. 28 can be specified as a wearable device for the arm with one or more close-fitting biometric sensors comprising: (a) an attachment member which is configured to span at least 60% of the circumference of a person's arm, wherein this attachment member further comprises—two symmetric plano-concave elastic portions, with first and second elasticity levels respectively, and an inelastic portion with a third elasticity level, wherein the third elasticity level is less than each of the first and second elasticity levels; (b) an enclosure which is connected to the concave sides of the two symmetric plano-concave elastic portions of the attachment member; and (c) one or more biometric sensors which collect data concerning arm tissue which are part of (or attached to) the enclosure.

In an example, an attachment member can be a band, strap, bracelet, bangle, armlet, cuff, or sleeve. In an example, an elastic portion of an attachment member can be made from elastic and/or stretchable fabric. In an example, an enclosure can be arcuate. In an example, an enclosure can be circular. In an example, a device can further comprise a display screen on the outward-facing surface of an enclosure. In an example, a biometric sensor can be a spectroscopic sensor which is configured to measure the spectrum of light energy reflected from (and/or absorbed by) tissue of a person's arm. In an example, a biometric sensor can be an electromagnetic energy sensor which is configured to measure parameters and/or patterns of electromagnetic energy passing through (and/or emitted by) tissue of a person's arm. In an example, measured parameters and/or patterns of electromagnetic energy can be selected from the group consisting of: impedance, resistance, conductivity, and electromagnetic wave pattern.

With respect to specific components, the example shown in FIG. 28 includes: first elastic portion 2802 of an attachment member; second elastic portion 2803 of an attachment member; first inelastic portion 2801 of an attachment member; second inelastic portion 2804 of an attachment member; enclosure 2805 with a display screen on its outward-facing surface; and biometric sensors 2806 and 2807. In an example, this device can further comprise one or more components selected from the group consisting of: a data processor; a battery and/or energy harvesting unit; a display screen; a data transmitter; and a data receiver. In an example, relevant embodiment variations discussed elsewhere in this or a priority-linked disclosure can also apply to this example.

Figure 29:
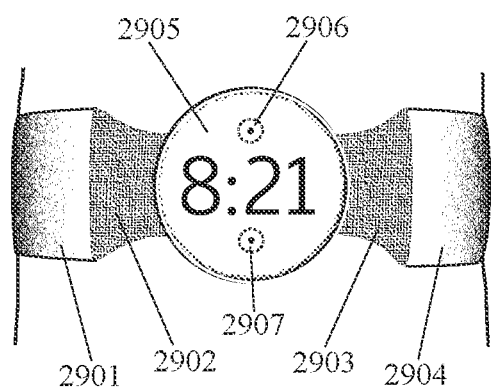
FIG. 29 shows an arm-worn device with biometric sensors on an enclosure which is connected to a strap by tapered elastic members.

FIG. 29 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner. The example shown in FIG. 29 is like the one shown in FIG. 28 except that in FIG. 29 the elastic portions are tapered (narrower in width) as they approach their connections with the enclosure.

With respect to specific components, the example shown in FIG. 29 includes: first tapered (width-varying) elastic portion 2902 of an attachment member; second tapered (width-varying) elastic portion 2903 of an attachment member; first inelastic portion 2901 of an attachment member; second inelastic portion 2904 of an attachment member; enclosure 2905 with a display screen on its outward-facing surface; and biometric sensors 2906 and 2907. In an example, this device can further comprise one or more components selected from the group consisting of: a data processor; a battery and/or energy harvesting unit; a display screen; a data transmitter; and a data receiver. In an example, relevant embodiment variations discussed elsewhere in this or a priority-linked disclosure can also apply to this example.

Figure 30:
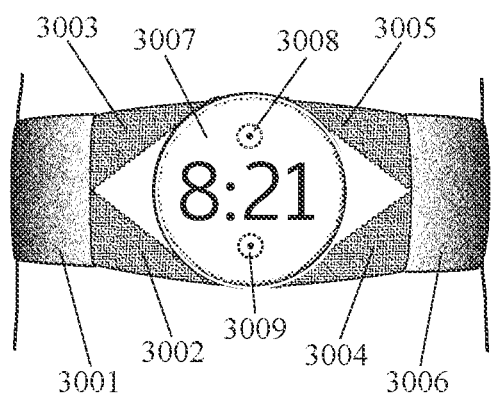
FIG. 30 shows an arm-worn device with biometric sensors on an enclosure which is connected to a strap by pennant-shaped elastic members.

FIG. 30 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner. The example shown in FIG. 30 is like the one shown in FIG. 28 except that in FIG. 30 there are four elastic portions, two connected to each side of the enclosure. Further, each elastic portion has a shape which is triangular and/or pennant shaped.

The example shown in FIG. 30 is a wearable device for the arm with one or more close-fitting biometric sensors comprising: (a) an attachment member which is configured to span at least 60% of the circumference of a person's arm, wherein this attachment member further comprises—four tapered (width-varying) elastic portions, wherein these elastic portions have a first elasticity level, and wherein these elastic portions are configured to be worn on the anterior (upper) portion of a person's arm; and one or more inelastic portions which comprise the remainder of the attachment member, wherein these inelastic portions have a second elasticity level which is less than the first elasticity level; (b) an enclosure, wherein a first side of the enclosure is connected to tapered ends of two of the four elastic portions of the attachment member and wherein a second (opposite) side of the enclosure is connected to tapered ends of the other two of the four elastic portions of the attachment member; and (c) one or more biometric sensors which collect data concerning arm tissue, wherein these sensors are part of (or attached to) the enclosure.

With respect to specific components, the example shown in FIG. 30 includes: first, second, third, and fourth tapered elastic portions (3002, 3003, 3004, and 3005) of an attachment member; first and second inelastic portions (3001 and 3006) of an attachment member; enclosure 3007 with a display screen on its outward-facing surface; and biometric sensors 3008 and 3009. In an example, this device can further comprise one or more components selected from the group consisting of: a data processor; a battery and/or energy harvesting unit; a display screen; a data transmitter; and a data receiver. In an example, relevant embodiment variations discussed elsewhere in this or a priority-linked disclosure can also apply to this example.

Figure 31:
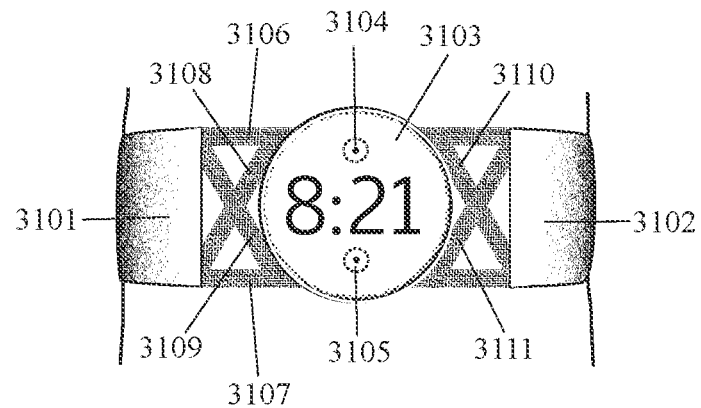
FIG. 31 shows an arm-worn device with biometric sensors on an enclosure which is connected to a strap by criss-crossed elastic members.

FIG. 31 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner. The example shown in FIG. 31 is like the one shown in FIG. 28 except that in FIG. 31 there are two elastic portions on each side of the enclosure which criss-cross each other, forming an "X" on each side of the enclosure. This design can help to keep the enclosure and sensors close to the surface of the arm for more consistent collection of biometric data.

The example shown in FIG. 31 is a wearable device for the arm with one or more close-fitting biometric sensors comprising: (a) an enclosure which is configured to be worn on a person's arm; (b) one or more biometric sensors which collect data concerning arm tissue, wherein these sensors are part of (or attached to) the enclosure; and (c) an attachment member which is configured to attach the enclosure to the person's arm, wherein the attachment member is configured to span at least 60% of the circumference of the person's arm, wherein the portion of the attachment member that connects to the enclosure includes elastic bands (or straps) on each side of the enclosure which criss-cross each other. In an example, the criss-crossing bands (or straps) on each side of the enclosure form an "X" on each side of the enclosure.

With respect to specific components, the example shown in FIG. 31 includes: inelastic portion 3101 of the attachment member; inelastic portion 3102 of the attachment member; enclosure 3103 with an outward-facing display screen; biometric sensors 3104 and 3105; and elastic bands (or straps) 3106, 3107, 3108, 3109, 3110, and 3111. In an example, this device can further comprise one or more components selected from the group consisting of: a data processor; a battery and/or energy harvesting unit; a display screen; a data transmitter; and a data receiver. In an example, relevant embodiment variations discussed elsewhere in this or a priority-linked disclosure can also apply to this example.

Figure 32:
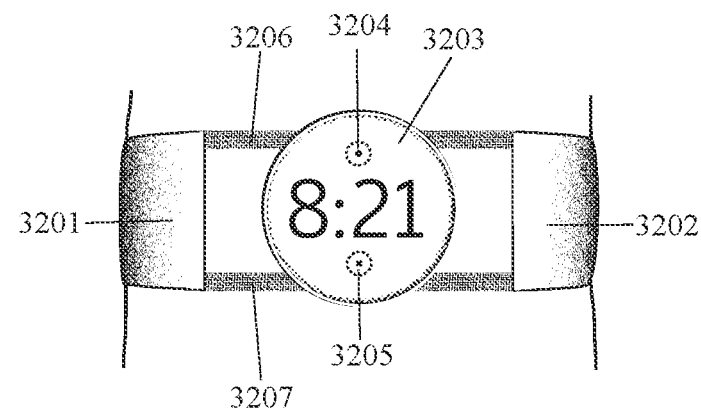
FIG. 32 shows an arm-worn device with biometric sensors on an enclosure which is connected on each side to a strap by two parallel elastic members.

FIG. 32 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner. The example shown in FIG. 32 is like the one shown in FIG. 28 except that in FIG. 32 there are two parallel elastic bands (or straps) connected to the enclosure. This design can help to keep the enclosure and sensors close to the surface of the arm for more consistent collection of biometric data.

The example shown in FIG. 32 is a wearable device for the arm with one or more close-fitting biometric sensors comprising: (a) an enclosure which is configured to be worn on a person's arm; (b) one or more biometric sensors which collect data concerning arm tissue, wherein these sensors are part of (or attached to) the enclosure; and (c) an attachment member which is configured to attach the enclosure to the person's arm, wherein the attachment member is configured to span at least 60% of the circumference of the person's arm, and wherein the portion of the attachment member that connects to the enclosure includes two parallel elastic bands (or straps) connected to the enclosure.

With respect to specific components, the example shown in FIG. 32 includes: inelastic portion 3201 of the attachment member; inelastic portion 3202 of the attachment member; enclosure 3203 with an outward-facing display screen; biometric sensors 3204 and 3205; and two parallel elastic bands (or straps) 3206 and 3207. In an example, this device can further comprise one or more components selected from the group consisting of: a data processor; a battery and/or energy harvesting unit; a display screen; a data transmitter; and a data receiver. In an example, relevant embodiment variations discussed elsewhere in this or a priority-linked disclosure can also apply to this example.

Figure 33:
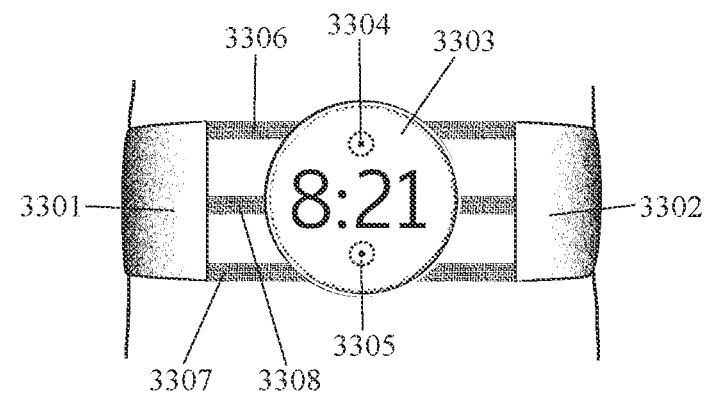
FIG. 33 shows an arm-worn device with biometric sensors on an enclosure which is connected on each side to a strap by three parallel elastic members.

FIG. 33 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner. The example shown in FIG. 33 is like the one shown in FIG. 28 except that in FIG. 33 there are three parallel elastic bands (or straps) connected to the enclosure. This design can help to keep the enclosure and sensors close to the surface of the arm for more consistent collection of biometric data.

The example shown in FIG. 33 is a wearable device for the arm with one or more close-fitting biometric sensors comprising: (a) an enclosure which is configured to be worn on a person's arm; (b) one or more biometric sensors which collect data concerning arm tissue, wherein these sensors are part of (or attached to) the enclosure; and (c) an attachment member which is configured to attach the enclosure to the person's arm, wherein the attachment member is configured to span at least 60% of the circumference of the person's arm, and wherein the portion of the attachment member that connects to the enclosure includes three parallel elastic bands (or straps) connected to the enclosure.

With respect to specific components, the example shown in FIG. 33 includes: inelastic portion 3301 of the attachment member; inelastic portion 3302 of the attachment member; enclosure 3303 with an outward-facing display screen; biometric sensors 3304 and 3305; and three parallel elastic bands (or straps) 3306, 3307, and 3308. In an example, this device can further comprise one or more components selected from the group consisting of: a data processor; a battery and/or energy harvesting unit; a display screen; a data transmitter; and a data receiver. In an example, relevant embodiment variations discussed elsewhere in this or a priority-linked disclosure can also apply to this example.

Figure 34:
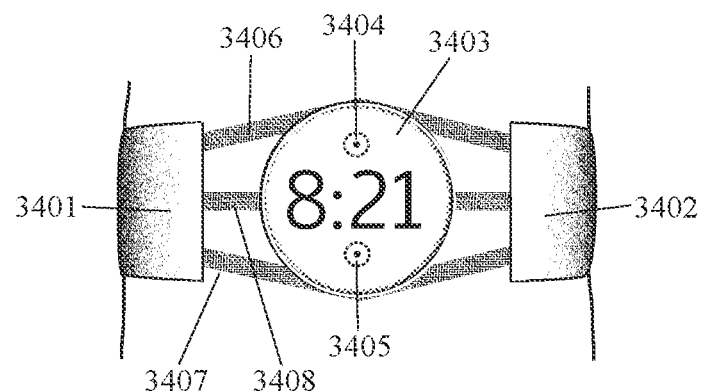
FIG. 34 shows an arm-worn device with biometric sensors on an enclosure which is connected on each side to a strap by three non-parallel elastic members.

FIG. 34 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner. The example shown in FIG. 34 is like the one shown in FIG. 33 except that the three elastic bands (or straps) are not parallel.

With respect to specific components, the example shown in FIG. 34 includes: inelastic portion 3401 of the attachment member; inelastic portion 3402 of the attachment member; enclosure 3403 with an outward-facing display screen; biometric sensors 3404 and 3405; and three elastic bands (or straps) 3406, 3407, and 3408. In an example, this device can further comprise one or more components selected from the group consisting of: a data processor; a battery and/or energy harvesting unit; a display screen; a data transmitter; and a data receiver. In an example, relevant embodiment variations discussed elsewhere in this or a priority-linked disclosure can also apply to this example.

Figure 35:
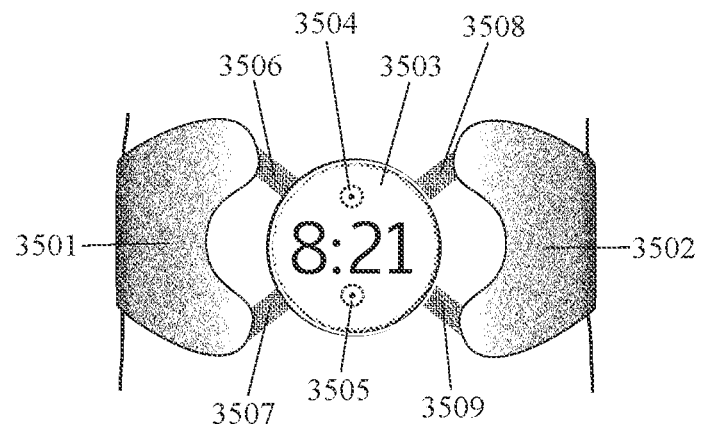
FIG. 35 shows an arm-worn device with biometric sensors on an enclosure which is connected on each side to a strap by two generally-perpendicular elastic members.

FIG. 35 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner. The example shown in FIG. 35 can be generally described as an arm-worn device with biometric sensors in an enclosure, wherein the enclosure is suspended on the surface of the arm by four elastic bands, and wherein each elastic band is individually connected to one of four points which are equally-spaced around the circumference of the enclosure. This enclosure suspension design can help to keep the sensors close to the surface of the arm for more consistent collection of biometric data.

The example shown in FIG. 35 can be specified as a wearable device for the arm with one or more close-fitting biometric sensors comprising: (a) an arcuate enclosure which is configured to be worn on a person's arm; (b) one or more biometric sensors which collect data concerning arm tissue, wherein these sensors are part of (or attached to) the enclosure; and (c) four elastic bands (or straps), each of which is connected to one of four points which are equally spaced around the circumference of the enclosure. In an example, each of the four elastic bands (or straps) can have one end which is connected to the enclosure and one end which is connected to an inelastic band, strap, bracelet, or armlet which is configured to span at least 50% of the circumference of the arm.

In another example, a wearable device for the arm with one or more close-fitting biometric sensors can comprise: (a) a quadrilateral enclosure which is configured to be worn on a person's arm; (b) one or more biometric sensors which collect data concerning arm tissue, wherein these sensors are part of (or attached to) the enclosure; and (c) four elastic bands (or straps), each of which is connected to one side of the enclosure. In an example, each of the four elastic bands (or straps) can have one end which is connected to the enclosure and one end which is connected to an inelastic band, strap, bracelet, or armlet which is configured to span at least 50% of the circumference of the arm.

With respect to specific components, the example shown in FIG. 35 includes: inelastic portion 3501 of the attachment member; inelastic portion 3502 of the attachment member; enclosure 3503 with an outward-facing display screen; biometric sensors 3504 and 3505; and four elastic bands (or straps) 3506, 3507, 3508, and 3509. In an example, this device can further comprise one or more components selected from the group consisting of: a data processor; a battery and/or energy harvesting unit; a display screen; a data transmitter; and a data receiver. In an example, relevant embodiment variations discussed elsewhere in this or a priority-linked disclosure can also apply to this example.

Figure 36:
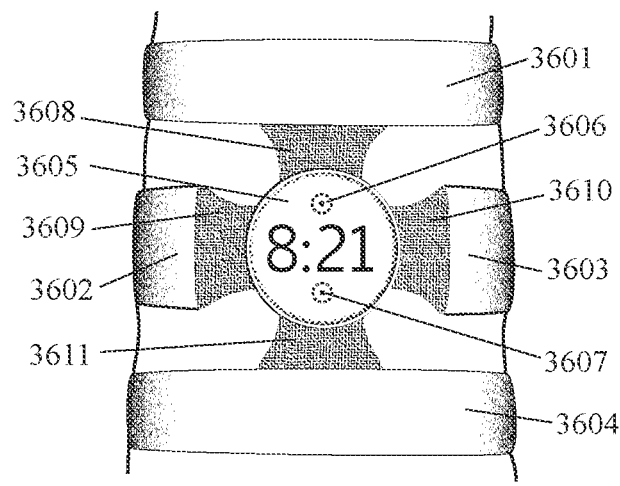
FIG. 36 shows an arm-worn device with biometric sensors and three circumferential bands.

FIG. 36 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner. The example shown in FIG. 36 can be generally described as an arm-worn device with biometric sensors in an enclosure, wherein the enclosure is suspended on the surface of the arm by four elastic suspension bands (or straps) connected to three parallel attachment bands or straps which encircle the arm. This enclosure suspension design can help to keep the sensors close to the surface of the arm for more consistent collection of biometric data.

The example shown in FIG. 36 can be specified as a wearable device for the arm with one or more close-fitting biometric sensors comprising: (a) an enclosure which is configured to be worn on a person's arm; (b) one or more biometric sensors which collect data concerning arm tissue, wherein these sensors are part of (or attached to) the enclosure; and (c) three parallel attachment bands, including proximal, middle, distal attachment bands; wherein each of the three parallel attachment bands is configured to span at least 60% of the circumference of the arm; and (d) four elastic suspension bands, wherein the four suspension bands are connected to the four sides of the enclosure, respectively; wherein two of the suspension bands are also connected to the proximal attachment band and the distal attachment band, respectively; and wherein the other two of the suspension bands are also connected to the middle attachment band. In an example, the word "strap" can be substituted for the word "band" in the above specification.

With respect to specific components, the example shown in FIG. 36 includes: a distal attachment band 3601, ends 3602 and 3603 of a middle attachment band, proximal attachment band 3604, enclosure 3605 with outward-facing display screen, biometric sensors 3606 and 3607, and four suspension bands 3608, 3609, 3610, and 3611. In an example, this device can further comprise one or more components selected from the group consisting of: a data processor; a battery and/or energy harvesting unit; a display screen; a data transmitter; and a data receiver. In an example, relevant embodiment variations discussed elsewhere in this or a priority-linked disclosure can also apply to this example.

Figure 37:
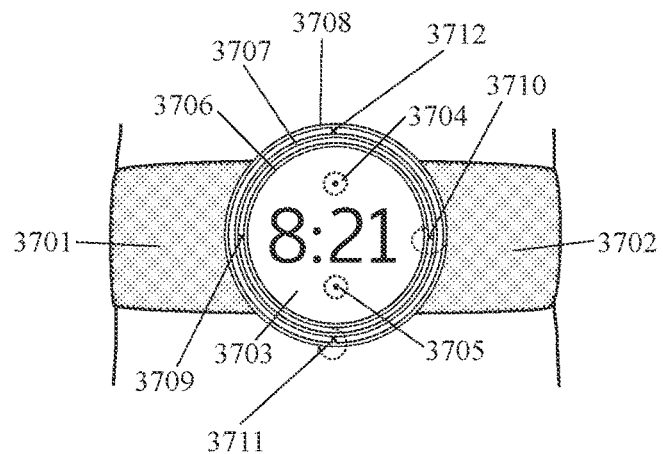
FIG. 37 shows an arm-worn device with biometric sensors on a gimbaled enclosure.

FIG. 37 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner. The example shown in FIG. 37 can be described as a wrist-worn device with a gimbaled enclosure that contains one or more biometric sensors. The gimbal mechanism around the enclosure enables the enclosure and sensors to remain relatively flat against the surface of the arm, even if the device shifts, rotates, and/or twists on the person's arm. This can help to maintain consistent measurement of biometric data from the arm.

The example in FIG. 37 can be specified as a wearable device for the arm with one or more close-fitting biometric sensors comprising: (a) an attachment member which is configured to span at least 60% of the circumference of a person's arm; (b) a gimbal mechanism which is connected to the attachment member, wherein this gimbal mechanism further comprises two or more concentric rings which are axially connected so that they can move relative to each other; (c) an enclosure within the most central concentric ring of the gimbal mechanism; and (d) one or more biometric sensors which are part of (or attached to) the enclosure, wherein these biometric sensors are configured to collect data concerning arm tissue.

In an example, an attachment member can be a strap, band, bracelet, bangle, chain, ring, armlet, cuff, gauntlet, or sleeve. In an example, an attachment member can stretch to span the entire circumference of a person's arm. In an example, an attachment member can have two ends which connect to each other to hold the attachment member onto a person's arm. In an example, an attachment member can be sufficiently rigid and/or resilient in shape that it has ends which hold onto the person's arm even though the ends are not connected to each other.

In an example, a gimbal mechanism can comprise two concentric (inner and outer) rings which pivot relative to each other, wherein these rings are connected by one or more axles at opposite sides of the inner ring. In an example, a gimbal mechanism can comprise three concentric (inner, central, and outer) rings which pivot relative to each other, wherein the outer and central rings are connected by one or more axles at a first set of opposite sides of the central ring, wherein the central and inner rings are connected by one or more axles at a second set of opposite sides of the central ring, and wherein the second set is at locations which are rotated around the circumference of the center ring by 90-degrees relative to the locations of the first set.

In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

In an example, an enclosure can further comprise a display screen which is seen on the outward-facing surface of the enclosure. In an example, the enclosure can be circular. In an example, this device can further comprise one or more components selected from the group consisting of: a data processor; a battery and/or energy harvesting unit; a display screen; a data transmitter; and a data receiver. In an example, relevant embodiment variations discussed elsewhere in this or a priority-linked disclosure can also apply to this example.

With respect to specific components, the example shown in FIG. 37 includes: first portion 3701 of an attachment member; second portion 3702 of the attachment member; enclosure 3703 with an outward-facing display screen; biometric sensors 3704 and 3705 within the enclosure; inner ring 3706, central ring 3707, and outer ring 3708 of a gimbal mechanism; first set of axles 3709 and 3710 connecting the inner ring and the central ring; and second set of axles 3711 and 3712 connecting the central ring and the outer ring.

Figure 38:
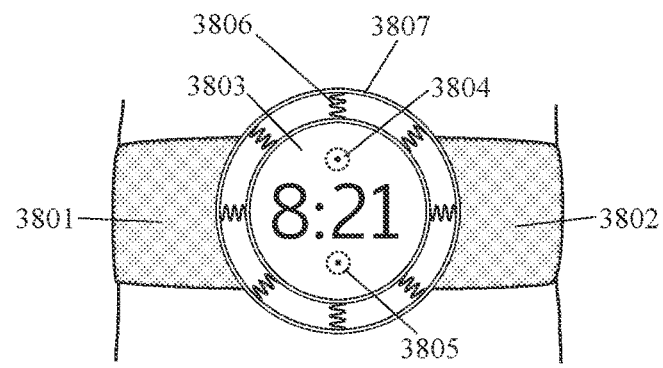
FIG. 38 shows an arm-worn device with biometric sensors on a radially-suspended enclosure.

FIG. 38 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner. The example shown in FIG. 38 is a wrist-worn device with an enclosure containing one or more biometric sensors, wherein this enclosure is suspended by a radial plurality of elastic (and/or stretchable or springy) suspension members which connect to locations on the circumference of the enclosure. In an example, this design can be called a "sunburst suspension system" because the elastic (and/or stretchable or springy) suspension members look like the radial sunrays in a traditional "sunburst" drawing. The "sunburst suspension" design enables the enclosure and sensors to remain relatively flat against the surface of the arm, even if the device shifts, rotates, and/or twists on the person's arm. This can help to maintain consistent measurement of biometric data from the arm.

The example in FIG. 38 can be specified as a wearable device for the arm with one or more close-fitting biometric sensors comprising: (a) an attachment member which is configured to span at least 60% of the circumference of a person's arm; (b) an enclosure; (c) one or more biometric sensors which are part of (or attached to) the enclosure, wherein these biometric sensors are configured to collect data concerning arm tissue; and (d) a plurality of elastic (and/or stretchable or springy) suspension members, wherein these suspension members flexibly connect the enclosure to the attachment member, wherein each of these suspension members is connected at one end to a location on the circumference of the enclosure and connected at its other end to the attachment member, and wherein the longitudinal axis of each of the suspension members is substantially parallel with a virtual radial spoke outward from the center of the enclosure.

In an example, an attachment member can be a strap, band, bracelet, bangle, chain, ring, armlet, cuff, gauntlet, or sleeve. In an example, an attachment member can stretch to span the entire circumference of a person's arm. In an example, an attachment member can have two ends which connect to each other to hold the attachment member onto a person's arm. In an example, an attachment member can be sufficiently rigid and/or resilient in shape that it has ends which hold onto the person's arm, even though the ends of the attachment member are not connected to each other.

In an example, an enclosure can be circular. In an example, an enclosure can further comprise a display screen which is seen on the outward-facing surface of the enclosure. In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. (Dr. James Mault, you da man!). In an example, measured parameters and/or patterns of electromagnetic energy can be selected from the group consisting of: impedance, resistance, conductivity, and electromagnetic wave pattern.

In an example, a suspension member can be a spring. In an example, a suspension member can be an elastic band or strap. In an example, the locations on the circumference of the enclosure to which the suspension members are connected can be evenly distributed around the circumference of the enclosure. In an example, there can be four suspension members. In an example, there can be six suspension members. In an example, there can be eight suspension members. In an example, this device can further comprise one or more components selected from the group consisting of: a data processor; a battery and/or energy harvesting unit; a display screen; a data transmitter; and a data receiver. In an example, relevant embodiment variations discussed elsewhere in this or a priority-linked disclosure can also apply to this example.

With respect to specific components, the example shown in FIG. 38 includes: first portion 3801 of an attachment member; second portion 3802 of the attachment member; enclosure 3803 with an outward-facing display screen; biometric sensors 3804 and 3805 within the enclosure; a plurality of spring suspension members, including 3806; and ring 3807.

Figure 39:
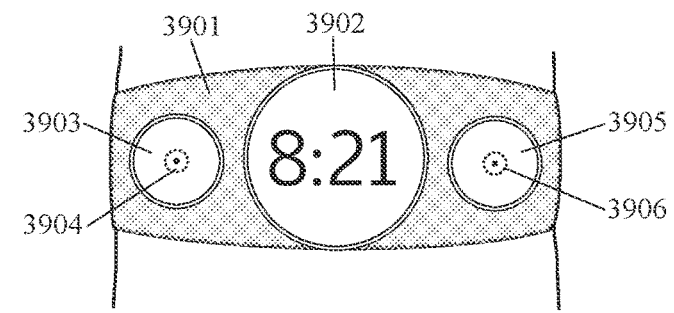
FIG. 39 shows an arm-worn device with biometric sensors on two arcuate enclosures.

FIG. 39 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner. The example shown in FIG. 39 is a flexible arm-worn device with two arcuate enclosures which contain biometric sensors.

The example in FIG. 39 can be specified as a wearable device for the arm with one or more close-fitting biometric sensors comprising: (a) a flexible attachment member which is configured to span at least 60% of the circumference of a person's arm; (b) a first arcuate enclosure whose center is at a first location on the circumference of the flexible attachment member; (c) a first biometric sensor which is part of (or attached to) the first arcuate enclosure, wherein this first biometric sensor is configured to collect data concerning arm tissue; (d) a second arcuate enclosure whose center is at a second location on the circumference of the flexible attachment member, wherein the distance between the first and second locations is greater than one-half inch; and (e) a second biometric sensor which is part of (or attached to) the second arcuate enclosure, wherein this second biometric sensor is configured to collect data concerning arm tissue.

In an example, a flexible attachment member can be a strap, band, bracelet, bangle, chain, ring, armlet, cuff, gauntlet, or sleeve. In an example, a flexible attachment member can stretch to span the entire circumference of a person's arm. In an example, a flexible attachment member can have two ends which connect to each other to hold the attachment member onto a person's arm. In an example, a flexible attachment member can be sufficiently rigid and/or resilient in shape that it has ends which hold onto the person's arm, even though the ends of the attachment member are not connected to each other.

In an example, an arcuate enclosure containing a biometric sensor can be circular. In an example, this device can further comprise a display screen between the two arcuate enclosures. In an alternative example, each of the arcuate enclosures can have a display screen on its outward-facing side. In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

With respect to specific components, the example shown in FIG. 39 includes: flexible attachment member 3901; central display screen 3902; first arcuate enclosure 3903; first biometric sensor 3904; second arcuate enclosure 3905; and second biometric sensor 3906. In an example, this device can further comprise one or more components selected from the group consisting of: a data processor; a battery and/or energy harvesting unit; a display screen; a data transmitter; and a data receiver. In an example, relevant embodiment variations discussed elsewhere in this or a priority-linked disclosure can also apply to this example.

Figure 40:
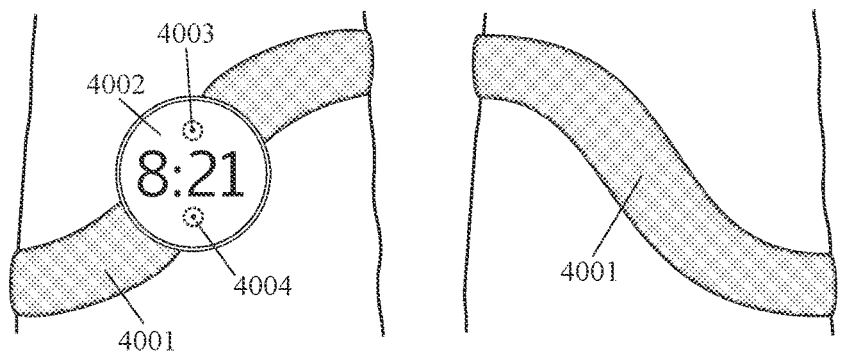
FIG. 40 shows an arm-worn device with biometric sensors on an enclosure which is diagonally connected to a strap.

FIG. 40 shows another example of a wearable device for the arm with one or more close-fitting biometric sensors. The left side of this figure shows the device from a top-down perspective, as it would appear spanning the anterior (upper) surface of a person's wrist (or other portion of the person's arm) in a circumferential manner. The right side of this figure shows the device from a bottom-up perspective, as it would appear spanning the posterior (lower) surface of a person's wrist (or other portion of the person's arm) in a circumferential manner. The example shown in FIG. 40 can be described as an arm-worn device with an arcuate enclosure to which a strap or band is connected diagonally.

The example in FIG. 40 can be specified as a wearable device for the arm with one or more close-fitting biometric sensors comprising: (a) an arcuate enclosure which is configured to be worn on a person's arm; (b) one or more biometric sensors which are configured to collect data concerning arm tissue and which are part of (or attached to) the arcuate enclosure; and (c) an attachment member which is configured to span at least 60% of the circumference of a person's arm, wherein a first portion of this attachment member is connected to the arcuate enclosure between the 12 o'clock and 3 o'clock positions (or 0-degree and 90-degree positions using compass coordinates) of the circumference of the enclosure; and wherein a second portion of this attachment member is connected to the arcuate enclosure between the 6 o'clock and 9 o'clock positions (or 180-degree and 270-degree positions using compass coordinates) of the circumference of the enclosure.

With respect to specific components, the example shown in FIG. 40 includes: attachment member 4001; enclosure 4002 with an outward-facing display screen; and biometric sensors 4003 and 4004 within the enclosure. In an example, this device can further comprise one or more components selected from the group consisting of: a data processor; a battery and/or energy harvesting unit; a display screen; a data transmitter; and a data receiver. Relevant embodiment variations discussed with respect to FIG. 37 or elsewhere in this disclosure can also be applied to this example.

Figure 41:
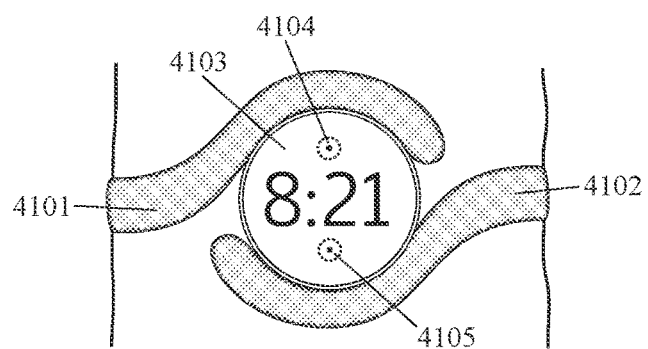
FIG. 41 shows an arm-worn device with biometric sensors and a "two gummi worm" design.

FIG. 41 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner. The example shown in FIG. 41 can be colorfully described as a "two gummi worm" design—because it looks like two gummi worms crawling in a symmetric manner around portions of the circumference of an enclosure.

The example in FIG. 41 can be specified as a wearable device for the arm with one or more close-fitting biometric sensors comprising: (a) an arcuate enclosure which is configured to be worn on a person's arm; (b) one or more biometric sensors which are configured to collect data concerning arm tissue and which are part of (or attached to) the arcuate enclosure; and (c) an attachment member which is configured to span at least 60% of the circumference of a person's arm, wherein a first portion of this attachment member spans most of the circumference of the arcuate enclosure between the 10 o'clock and 2 o'clock positions (or 300-degree and 60-degree positions using compass coordinates); and wherein a second portion of this attachment member spans most of the circumference of the arcuate enclosure between the 4 o'clock and 8 o'clock positions (or 120-degree and 240-degree positions using compass coordinates).

With respect to specific components, the example shown in FIG. 41 includes: first portion 4101 of an attachment member; second portion 4102 of an attachment member; enclosure 4103 with an outward-facing display screen; and biometric sensors 4104 and 4105 within the enclosure. In an example, this device can further comprise one or more components selected from the group consisting of: a data processor; a battery and/or energy harvesting unit; a display screen; a data transmitter; and a data receiver. Relevant embodiment variations discussed with respect to FIG. 37 or elsewhere in this disclosure can also be applied to this example.

Figure 42:
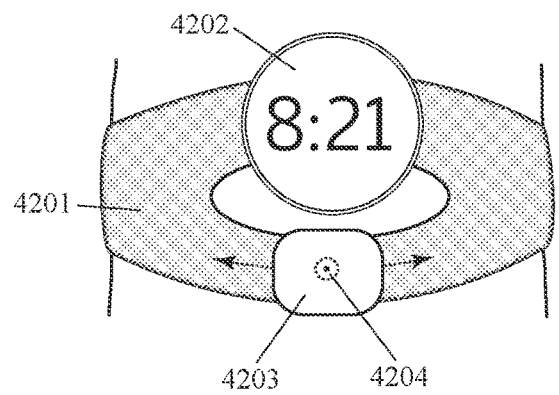
FIG. 42 shows an arm-worn device with biometric sensors on one arm of a bifurcating band.

FIG. 42 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner. The example shown in FIG. 42 can be generally described as an arm-worn device with a bifurcating band, wherein one branch of the band is connected to a display screen and the other branch of the band is connected to a circumferentially-sliding enclosure which contains one or more biometric sensors. Having biometric sensors on a separate circumferentially-sliding enclosure enables adjustment of the circumferential location from which biometric data is collected, without changing the location of a display screen.

The example in FIG. 42 can be specified as a wearable device for the arm with one or more close-fitting biometric sensors comprising: (a) an attachment member which is configured to span at least 60% of the circumference of a person's arm, wherein this attachment member has a first circumferential portion which bifurcates into a first branch and a second branch, and wherein this attachment member has a second circumferential portion in which the first branch and the second branch reconverge; (b) a display screen which is connected to the first branch of the attachment member; (c) a circumferentially-sliding enclosure which is connected to the second branch of the attachment member; and (d) one or more biometric sensors which are configured to collect data concerning arm tissue and which are part of (or attached to) the circumferentially-sliding enclosure.

With respect to specific components, the example shown in FIG. 42 includes: bifurcating attachment member 4201; display screen 4202 on a first branch of the attachment member; circumferentially-sliding enclosure 4203 on a second branch of the attachment member; and biometric sensor 4204 within the circumferentially-sliding enclosure. In an example, this device can further comprise one or more components selected from the group consisting of: a data processor; a battery and/or energy harvesting unit; a display screen; a data transmitter; and a data receiver. Relevant embodiment variations discussed with respect to FIG. 37 or elsewhere in this disclosure can also be applied to this example.

Figure 43:
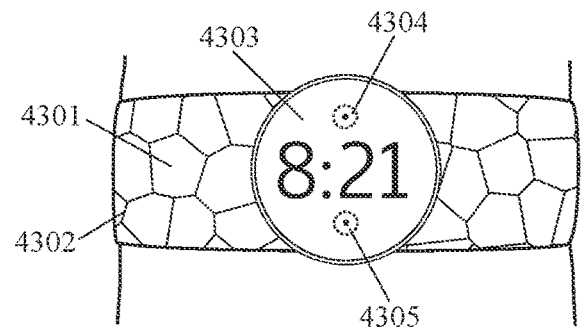
FIG. 43 shows an arm-worn device with biometric sensors and a plurality of various-shaped polygons connected by flexible strips or joints.

FIG. 43 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner.

The example in FIG. 43 can be specified as a wearable device for the arm with one or more close-fitting biometric sensors comprising: (a) an attachment member which is configured to span at least 60% of the circumference of a person's arm, wherein this attachment member further comprises a plurality of various-shaped (rigid) polygons which are inter-connected by flexible strips and/or joints; (b) an enclosure which is connected to the attachment member; and (c) one or more biometric sensors which are configured to collect data concerning arm tissue and which are part of (or attached to) the enclosure. Such a design can help to keep the enclosure (and thus the sensors) flat against the surface of the person's arm, even if the attachment member shifts, twists, or rotates.

In an example, a majority of the various-shaped polygons can have five sides. In an example, a majority of the various-shaped polygons can have six sides. In an example, a majority of the various-shaped polygons can have unequal sides. In an example, a majority of the various-shaped polygons can have unequal angles between sides. In an example, sides of the various-shaped polygons can be inter-connected by strips of flexible fabric. In an example, sides of the various-shaped polygons can be inter-connected by hinge joints. In an example, the enclosure can have a display screen on its outward-facing surface.

With respect to specific components, the example shown in FIG. 43 includes: a plurality of various-shaped inter-connected polygons, including polygon 4301; a plurality of flexible joints, including joint 4302; an arcuate enclosure 4303 which further comprises a display screen on its outward-facing surface; and biometric sensors 4304 and 4305 within the enclosure. In an example, this device can further comprise one or more components selected from the group consisting of: a data processor; a battery and/or energy harvesting unit; a display screen; a data transmitter; and a data receiver. Relevant embodiment variations discussed with respect to FIG. 37 or elsewhere in this disclosure can also be applied to this example.

Figure 44:
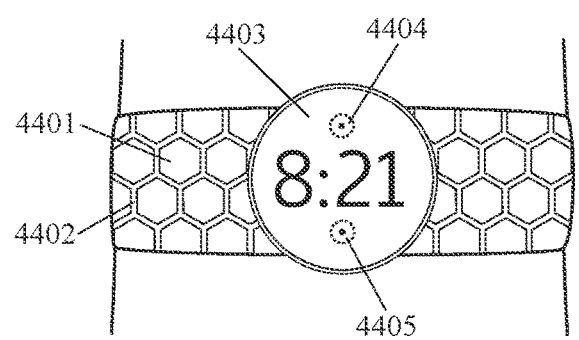
FIG. 44 shows an arm-worn device with biometric sensors and a plurality of hexagons connected by flexible strips or joints.

FIG. 44 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner. In this example, an attachment member has a honeycomb configuration. This can help to keep the enclosure (and thus the sensors) flat against the surface of the person's arm, even if the attachment member shifts, twists, or rotates.

The example in FIG. 44 can be specified as a wearable device for the arm with one or more close-fitting biometric sensors comprising: (a) an attachment member which is configured to span at least 60% of the circumference of a person's arm, wherein this attachment member further comprises a plurality of flexibly-connected (rigid) hexagons; (b) an enclosure which is connected to the attachment member; and (c) one or more biometric sensors which are configured to collect data concerning arm tissue and which are part of (or attached to) the enclosure.

With respect to specific components, the example shown in FIG. 44 includes: a plurality of hexagons, including hexagon 4401; a plurality of flexible joints, including joint 4402; an arcuate enclosure 4403 which further comprises a display screen on its outward-facing surface; and biometric sensors 4404 and 4405 within the enclosure. In an example, this device can further comprise one or more components selected from the group consisting of: a data processor; a battery and/or energy harvesting unit; a display screen; a data transmitter; and a data receiver. Relevant embodiment variations discussed with respect to FIG. 37 or elsewhere in this disclosure can also be applied to this example.

Figure 45:
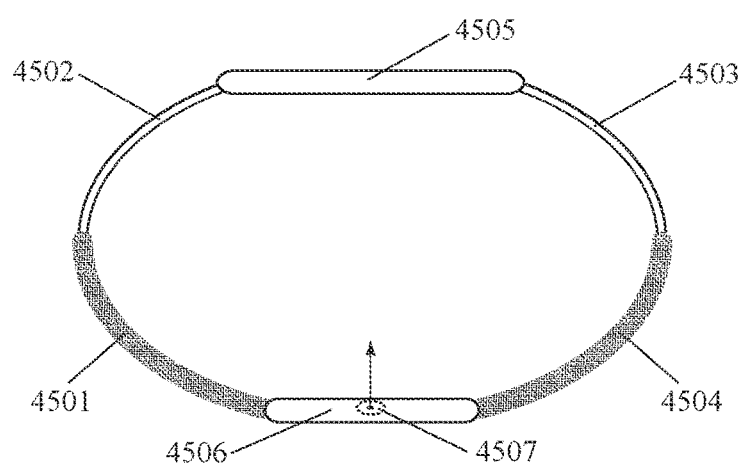
FIG. 45 shows an arm-worn device with biometric sensors and a band with two elastic quadrants.

FIG. 45 shows another example of a wearable device for the arm with one or more close-fitting biometric sensors. This figure shows the device from a side perspective, as it would appear encircling a lateral cross-section of a person's wrist (or other portion of the person's arm). In this example, one or more biometric sensors are located on a portion of the device which is diametrically-opposite (e.g. symmetric relative to the circumferential center of the device) from the portion of the device which includes a display screen. In an example, one or more biometric sensors can be configured to be worn on the posterior (lower) surface of an arm and a display screen can be configured to be worn on the anterior (upper) surface of the arm, or vice versa.

The specific example in FIG. 45 can be specified as a wearable device for the arm with one or more close-fitting biometric sensors comprising: (a) an attachment member which is configured to span at least 60% of the circumference of a person's arm, wherein this attachment member further comprises a first portion with a first elasticity level spanning completely or partially (clockwise) between the 9 o'clock and 3 o'clock (or 270-degree and 90-degree) positions around the device circumference and a second portion with a second elasticity level spanning completely or partially (clockwise) between the 3 o'clock and 9 o'clock (or 90-degree and 270-degree) positions around the device circumference, wherein the second elasticity level is greater than the first elasticity level; (b) a display screen which is part of (or connected to) the first portion of the attachment member; (c) an enclosure which is part of (or connected to) the second portion of the attachment member; and (d) one or more biometric sensors which are configured to collect data concerning arm tissue and which are part of (or attached to) the enclosure.

In an example, the display screen can be centrally located with respect to the first portion of the attachment member. In an example, the center of the display screen can be located at the 12 o'clock (or 0-degrees) position on the circumference of the device. In an example, the enclosure can be centrally located with respect to the second portion of the attachment member. In an example, the center of the display screen can be located at the 6 o'clock (or 180-degrees) position on the circumference of the device.

With respect to specific components, the example shown in FIG. 45 includes: elastic segments 4501 and 4504 of an attachment member; inelastic segments 4502 and 4503 of an attachment member; display screen 4505; enclosure 4506; and biometric sensor 4507. In an example, this device can further comprise one or more components selected from the group consisting of: a data processor; a battery and/or energy harvesting unit; a display screen; a data transmitter; and a data receiver. Relevant embodiment variations discussed with respect to FIG. 37 or elsewhere in this disclosure can also be applied to this example.

FIG. 46 shows another example of a wearable device for the arm with one or more close-fitting biometric sensors. This figure shows the device from a side perspective, as it would appear encircling a lateral cross-section of a person's wrist (or other portion of the person's arm). In this example, one or more biometric sensors are located on a portion of the device which is diametrically-opposite (e.g. symmetric relative to the circumferential center of the device) from the portion of the device which includes a display screen and there is a connector (such as a buckle, clip, clasp, pin, plug, or hook-and-eye mechanism) on the device between the sensors and the screen.

The example in FIG. 46 can be specified as a wearable device for the arm with one or more close-fitting biometric sensors comprising: (a) an attachment member which is configured to span at least 60% of the circumference of a person's arm; (b) a display screen which is part of (or connected to) the attachment member at a first location along the circumference of the device; (c) an enclosure which is part of (or connected to) the attachment member at a second location along the circumference of the device, wherein the second location is on the opposite side of the device (e.g. through the circumferential center of the device) from the first location; (d) one or more biometric sensors which are configured to collect data concerning arm tissue and which are part of (or attached to) the enclosure; and (e) a connector which connects two ends of the attachment member to each other, wherein this connector is at a location along the circumference of the device which is between the display screen and the enclosure.

The example in FIG. 46 can also be specified as a wearable device for the arm with one or more close-fitting biometric sensors comprising: (a) an attachment member which is configured to span at least 60% of the circumference of a person's arm; (b) a display screen which is located between the 10 o'clock and 2 o'clock (or 300-degree and 60-degree) positions on the circumference of the attachment member; (c) an enclosure which is located between the 4 o'clock and 8 o'clock (or 120-degree and 240-degree) positions on the circumference of the attachment member; (d) one or more biometric sensors which are configured to collect data concerning arm tissue and which are part of (or attached to) the enclosure; and (e) a connector which connects two ends of the attachment member to each other, wherein this connector is at a location along the circumference of the device which is between the display screen and the enclosure.

In an example, the center of the display screen can be located at the 12 o'clock (or 0-degrees) position on the circumference of the device. In an example, the center of the display screen can be located at the 6 o'clock (or 180-degrees) position on the circumference of the device. In an example, a connector can be selected from the group consisting of: buckle, clip, clasp, hook, plug, pin, snap, and hook-and-eye mechanism.

With respect to specific components, the example shown in FIG. 46 includes: segments 4601, 4602, and 4603 of an attachment member; connector 4604; display screen 4605; enclosure 4606; and biometric sensor 4607. In an example, this device can further comprise one or more components selected from the group consisting of: a data processor; a battery and/or energy harvesting unit; a display screen; a data transmitter; and a data receiver. Relevant embodiment variations discussed with respect to FIG. 37 or elsewhere in this disclosure can also be applied to this example.

FIG. 47 shows another example of a wearable device for the arm with one or more close-fitting biometric sensors. This figure shows the device from a side perspective, as it would appear encircling a lateral cross-section of a person's wrist (or other portion of the person's arm). In this example, there are one or more biometric sensors which are opposite a display screen, a connector between the sensors and the screen, and a hinge which is opposite the connector. If portions of an attachment member connecting these components are relatively rigid, then this example can be called a "clam shell" design.

The example in FIG. 47 can be specified as a wearable device for the arm with one or more close-fitting biometric sensors comprising: (a) an attachment member which is configured to span at least 60% of the circumference of a person's arm; (b) a display screen which is part of (or connected to) the attachment member at a first location around the circumference of the device; (c) an enclosure which is part of (or connected to) the attachment member at a second location around the circumference of the device, wherein the second location is on the opposite (e.g. through the circumferential center) side of the device from the first location; (d) one or more biometric sensors which are configured to collect data concerning arm tissue and which are part of (or attached to) the enclosure; and (e) a connector which connects two ends of the attachment member to each other at a third location around the circumference of the device, wherein this third location is between the first and second locations; (f) a hinge (or joint) which connects two portions of the attachment member to each other at a fourth location around the circumference of the device, wherein this fourth location is on the opposite (e.g. through the circumferential center) side of the device from the third location.

The example in FIG. 47 can also be specified as a wearable device for the arm with one or more close-fitting biometric sensors comprising: (a) an attachment member which is configured to span at least 60% of the circumference of a person's arm; (b) a display screen which is located between the 10 o'clock and 2 o'clock (or 300-degree and 60-degree) positions on the circumference of the attachment member; (c) an enclosure which is located between the 4 o'clock and 8 o'clock (or 120-degree and 240-degree) positions on the circumference of the attachment member; (d) one or more biometric sensors which are configured to collect data concerning arm tissue and which are part of (or attached to) the enclosure; (e) a connector which connects two ends of the attachment member to each other, wherein this connector is located between the 7 o'clock and 11 o'clock (or 210-degree and 330-degree) positions on the circumference of the attachment member; and (f) a hinge which connects two portions of the attachment member to each other, wherein this hinge is located between the 1 o'clock and 5 o'clock (or 30-degree and 150-degree) positions on the circumference of the attachment member.

In an example, the center of the display screen can be located at the 12 o'clock (or 0-degrees) position on the circumference of the device. In an example, the center of the display screen can be located at the 6 o'clock (or 180-degrees) position on the circumference of the device. In an example, a connector can be selected from the group consisting of: buckle, clip, clasp, hook, plug, pin, snap, and hook-and-eye mechanism.

With respect to specific components, the example shown in FIG. 47 includes: segments 4701, 4702, and 4703 of an attachment member; connector 4704; hinge 4705; display screen 4706; enclosure 4707; and biometric sensor 4708. In an example, this device can further comprise one or more components selected from the group consisting of: a data processor; a battery and/or energy harvesting unit; a display screen; a data transmitter; and a data receiver. Relevant embodiment variations discussed with respect to FIG. 37 or elsewhere in this disclosure can also be applied to this example.

FIG. 48 shows another example of a wearable device for the arm with one or more close-fitting biometric sensors. This figure shows the device from a side perspective, as it would appear encircling a lateral cross-section of a person's wrist (or other portion of the person's arm). This example is similar to the one shown in FIG. 47 except a biometric sensor is on the center-facing surface of a compressible member.

With respect to specific components, the example shown in FIG. 48 includes: segments 4801, 4802, and 4803 of an attachment member; connector 4804; hinge 4805; display screen 4806; compressible member 4807; and biometric sensor 4808. In an example, this device can further comprise one or more components selected from the group consisting of: a data processor; a battery and/or energy harvesting unit; a display screen; a data transmitter; and a data receiver.

In an example, a compressible member can be an elastic member which is filled with a fluid, gel, or gas. In an example, a compressible member can be a pneumatic or hydraulic chamber which is filled with a fluid, gel, or gas. In an example, a compressible member can be a balloon. In an example, a compressible member can be made from compressible foam. Relevant embodiment variations discussed with respect to FIG. 47 or elsewhere in this disclosure can also be applied to this example.

Figure 49:
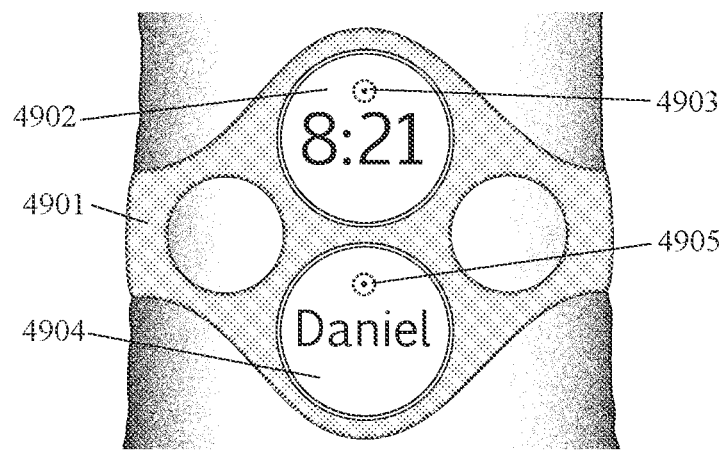
FIG. 49 shows a first arm-worn device with biometric sensors and a bulging band with two display screens.

FIG. 49 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner. Described generally, the example shown in FIG. 49 is a biometric-sensing device with proximal and distal arcuate display screens which are attached to a person's arm by a band, wherein the band has one holes on each side of a virtual line connecting the centers of the two displays.

Described more specifically, the example shown in FIG. 49 is a wearable device for the arm with one or more close-fitting biometric sensors comprising: (a) a proximal arcuate display screen, wherein this proximal arcuate display screen is a first distance from a person's shoulder; (b) a distal arcuate display screen, wherein this distal arcuate display screen is a second distance from a person's shoulder, and wherein the second distance is greater than the first distance; (c) an attachment member which attaches the proximal arcuate display screen and the distal arcuate display screen to the person's arm, wherein this attachment member has one hole on each side of a virtual line connecting the center of the proximal arcuate display screen and the center of the distal arcuate display screen; and (d) one or more biometric sensors which are configured to collect data concerning arm tissue.

In an example, a display screen can be circular. In an example, a display screen can be activated by touch and/or gesture. In an example, a virtual line connecting the center of a proximal display screen and the center of a distal display screen can parallel to the longitudinal axis of the arm. In an example, holes on each side of this virtual line can be circular. In an example, the area of a hole in an attachment member can be half of the area of a display screen. In an example, the area of a hole in an attachment member can be the same as the area of a display screen. In an example, the area of a hole in an attachment member can be between 50% and 100% of the area of a display screen.

In an example, an attachment member can be a strap, band, bracelet, bangle, ring, armlet, gauntlet, cuff, or sleeve. In an example, an attachment member can be wider as it spans the anterior (upper) surface of a person's arm. In an example, an attachment member can be attached to a person's arm by connecting two ends of the attachment member with a clasp, clip, buckle, hook, pin, plug, or hook-and-eye mechanism. In an example, the attachment member can be attached to a person's arm by stretching and sliding it over the person's hand onto the arm. In an example, the attachment member can be attached to a person's arm by applying force to pull two ends apart to slip the member over the arm, wherein the two ends retract back towards each other when the force is removed.

In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

Specific components in the example shown in FIG. 49 include: attachment member 4901 which has a hole on each side of a central longitudinal axis of the anterior (upper) surface of an arm; distal display screen 4902; proximal display screen 4904; and biometric sensors 4903 and 4905. In an example, this device can further comprise one or more components selected from the group consisting of: a data processor; a battery and/or energy harvesting unit; a data transmitter; and a data receiver. In an example, this device can function as a smart watch. Relevant embodiment variations discussed elsewhere in this or a priority-linked disclosure can also be applied to this example.

Figure 50:
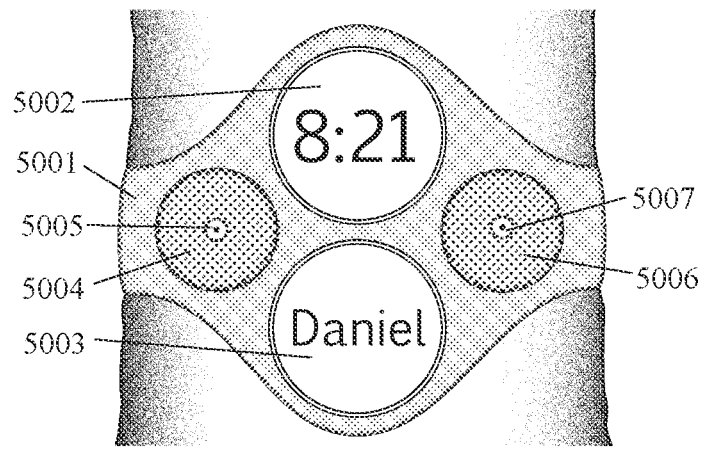
FIG. 50 shows a second arm-worn device with biometric sensors and a bulging band with two display screens.

FIG. 50 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner. Described generally, the example shown in FIG. 50 is an arm-worn biometric-sensing device with: proximal and distal arcuate display screens; and right and left side enclosures with biometric sensors.

Described more specifically, the example shown in FIG. 50 is a wearable device for the arm with one or more close-fitting biometric sensors comprising: (a) a proximal arcuate display screen, wherein this proximal arcuate display screen is a first distance from a person's shoulder; (b) a distal arcuate display screen, wherein this distal arcuate display screen is a second distance from a person's shoulder, and wherein the second distance is greater than the first distance; (c) a right-side enclosure, wherein the center of this right-side enclosure is to the right of a virtual line connecting the center of the proximal arcuate display screen and the center of the distal arcuate display screen, and wherein this right-side enclosure further comprises a biometric sensor that is configured to collect data concerning arm tissue; (d) a left-side enclosure, wherein the center of this left-side enclosure is to the left of a virtual line connecting the center of the proximal arcuate display screen and the center of the distal arcuate display screen, and wherein this left-side enclosure further comprises a biometric sensor that is configured to collect data concerning arm tissue; and (e) an attachment member which attaches the proximal arcuate display screen, the distal arcuate display screen, the right-side enclosure, and the left-side enclosure to the person's arm.

In an example, a display screen can be circular. In an example, a display screen can be activated by touch and/or gesture. In an example, a virtual line connecting the center of a proximal display screen and the center of a distal display screen can parallel to the longitudinal axis of the arm. In an example, an attachment member can be a strap, band, bracelet, bangle, ring, armlet, gauntlet, cuff, or sleeve. In an example, an attachment member can be wider as it spans the anterior (upper) surface of a person's arm. In an example, an attachment member can be attached to a person's arm by connecting two ends of the attachment member with a clasp, clip, buckle, hook, pin, plug, or hook-and-eye mechanism. In an example, the attachment member can be attached to a person's arm by stretching and sliding it over the person's hand onto the arm. In an example, the attachment member can be attached to a person's arm by applying force to pull two ends apart to slip the member over the arm, wherein the two ends retract back towards each other when the force is removed.

In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

Specific components in the example shown in FIG. 50 include: attachment member 5001; distal display screen 5002; proximal display screen 5003; right-side enclosure 5006 with biometric sensor 5007; and left-side enclosure 5004 with biometric sensor 5005. In an example, this device can further comprise one or more components selected from the group consisting of: a data processor; a battery and/or energy harvesting unit; a data transmitter; and a data receiver. In an example, this device can function as a smart watch. Relevant embodiment variations discussed elsewhere in this or a priority-linked disclosure can also be applied to this example.

Figure 51:
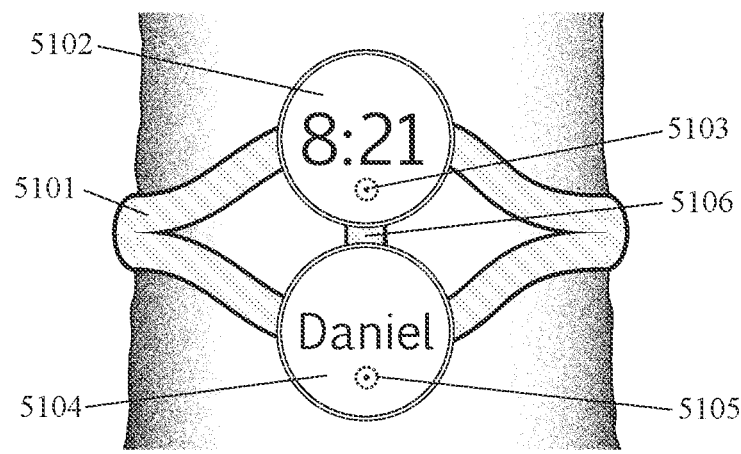
FIG. 51 shows an arm-worn device with biometric sensors and a bifurcating band with two display screens.

FIG. 51 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner. Described generally, the example shown in FIG. 51 is an arm-worn biometric-sensing device with proximal and distal arcuate display screens which are circumferentially attached to an arm by a bifurcating band (or strap) and also connected to each other by a band (or strap) along the central longitudinal axis of the anterior (upper) surface of the arm.

Described more specifically, the example shown in FIG. 51 is a wearable device for the arm with one or more close-fitting biometric sensors comprising: (a) a proximal arcuate display screen, wherein this proximal arcuate display screen is configured to be worn a first distance from a person's shoulder; (b) a distal arcuate display screen, wherein this distal arcuate display screen is configured to be worn a second distance from a person's shoulder, and wherein the second distance is greater than the first distance; (c) one or more biometric sensors that are configured to collect data concerning arm tissue; (d) a bifurcated attachment member, wherein this bifurcated attachment member bifurcates into a proximal and distal branches as it spans the anterior (upper) surface of the person's arm, wherein these proximal and distal branches reconverge as the bifurcated attachment member further spans the anterior (upper) surface of the person's arm, wherein the proximal branch is configured to attach the proximal arcuate display screen to the person's arm, and wherein the distal branch is configured to attach the distal arcuate display screen to the person's arm; and (e) an inter-display connecting band (or strip) which connects the proximal arcuate display screen to the distal arcuate display screen.

In an example, a display screen can be circular. In an example, a display screen can be activated by touch and/or gesture. In an example, a virtual line connecting the center of a proximal display screen and the center of a distal display screen can parallel to the longitudinal axis of the arm. In an example, an inter-display connecting band (or strip) connecting the center of a proximal display screen and the center of a distal display screen can parallel to the longitudinal axis of the arm.

In an example, an attachment member can be a strap, band, bracelet, bangle, ring, armlet, gauntlet, cuff, or sleeve. In an example, an attachment member can be wider as it spans the anterior (upper) surface of a person's arm. In an example, an attachment member can be attached to a person's arm by connecting two ends of the attachment member with a clasp, clip, buckle, hook, pin, plug, or hook-and-eye mechanism. In an example, the attachment member can be attached to a person's arm by stretching and sliding it over the person's hand onto the arm. In an example, the attachment member can be attached to a person's arm by applying force to pull two ends apart to slip the member over the arm, wherein the two ends retract back towards each other when the force is removed.

In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

Specific components in the example shown in FIG. 51 include: bifurcated attachment member 5101; distal display screen 5102; proximal display screen 5104; biometric sensors 5103 and 5105; and inter-display connecting band 5106. In an example, this device can further comprise one or more components selected from the group consisting of: a data processor; a battery and/or energy harvesting unit; a data transmitter; and a data receiver. In an example, this device can function as a smart watch. Relevant embodiment variations discussed elsewhere in this or a priority-linked disclosure can also be applied to this example.

Figure 52:
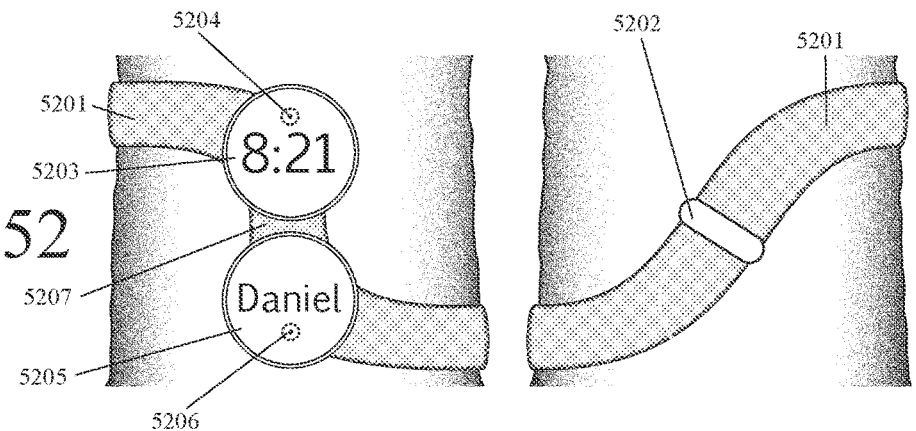
FIG. 52 shows an arm-worn device with biometric sensors and a serpentine band with two display screens.

FIG. 52 shows another example of a wearable device for the arm with one or more close-fitting biometric sensors. The left side of this figure shows the device from a top-down perspective, as it would appear spanning the anterior (upper) surface of a person's wrist (or other portion of the person's arm) in a circumferential manner. The right side of this figure shows the device from a bottom-up perspective, as it would appear spanning the posterior (lower) surface of a person's wrist (or other portion of the person's arm) in a circumferential manner. Described generally, the example shown in FIG. 52 is an arm-worn biometric-sensing device with proximal and distal arcuate display screens which are attached to a person's arm by a band with an "S"-shaped portion spanning the anterior (upper) portion of the arm.

Described more specifically, the example shown in FIG. 52 is a wearable device for the arm with one or more close-fitting biometric sensors comprising: (a) a proximal arcuate display screen, wherein this proximal arcuate display screen is configured to be worn a first distance from a person's shoulder; (b) a distal arcuate display screen, wherein this distal arcuate display screen is configured to be worn a second distance from a person's shoulder, and wherein the second distance is greater than the first distance; (c) one or more biometric sensors that are configured to collect data concerning arm tissue; (d) a attachment member which is attached to the right side of the proximal arcuate display screen and to the left side of the distal arcuate display screen; (e) an inter-display connecting band which connects the distal portion of the proximal display screen to the proximal portion of the distal arcuate display screen.

Alternatively, a wearable device for the arm with one or more close-fitting biometric sensors can comprise: (a) a proximal arcuate display screen, wherein this proximal arcuate display screen is configured to be worn a first distance from a person's shoulder; (b) a distal arcuate display screen, wherein this distal arcuate display screen is configured to be worn a second distance from a person's shoulder, and wherein the second distance is greater than the first distance; (c) one or more biometric sensors that are configured to collect data concerning arm tissue; (d) a attachment member which is attached to the left side of the proximal arcuate display screen and to the right side of the distal arcuate display screen; (e) an inter-display band which connects the distal portion of the proximal display screen to the proximal portion of the distal arcuate display screen.

In an example, an attachment member can be a strap, band, bracelet, bangle, ring, armlet, gauntlet, cuff, or sleeve. In an example, an attachment member can be attached to a person's arm by connecting two ends of the attachment member with a clasp, clip, buckle, hook, pin, plug, or hook-and-eye mechanism. In an example, the attachment member can be attached to a person's arm by stretching and sliding it over the person's hand onto the arm. In an example, the attachment member can be attached to a person's arm by applying force to pull two ends apart to slip the member over the arm, wherein the two ends retract back towards each other when the force is removed.

In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

Specific components in the example shown in FIG. 52 include: attachment member 5201; connector 5202; distal display screen 5203; proximal display screen 5205; biometric sensors 5204 and 5206; and inter-display band 5207. In an example, this device can further comprise one or more components selected from the group consisting of: a data processor; a battery and/or energy harvesting unit; a data transmitter; and a data receiver. In an example, this device can function as a smart watch. Relevant embodiment variations discussed elsewhere in this or a priority-linked disclosure can also be applied to this example.

Figure 53:
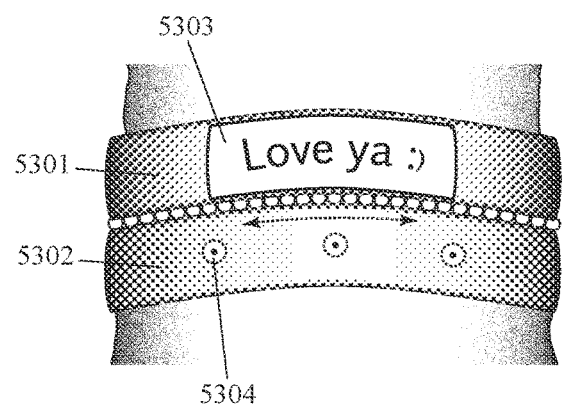
FIG. 53 shows an arm-worn device with biometric sensors and two separately-rotatable bands.

FIG. 53 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner. The example shown in FIG. 53 can be described as a wearable device with two bands which encircle an arm, wherein these two bands are movably-attached to each other in a manner which allows a second band (with biometric sensors) to be rotated relative to a first band. Such rotation enables adjustment of the locations of one or more biometric sensors relative to the arm in order to improve collection of biometric data from arm tissue.

More specifically, the example shown in FIG. 53 is a wearable device for the arm with one or more close-fitting biometric sensors comprising: (a) a first band which is configured to span at least 60% of the circumference of a person's arm; (b) a second band which is configured to span at least 60% of the circumference of the person's arm, wherein the first band and the second band are attached to each other by a mechanism that enables the second band to be circumferentially-rotated relative to the first band; and (c) one or more biometric sensors which are configured to collect data concerning arm tissue, wherein these biometric sensors are part of (or attached to) the second band.

More generally, the example shown in FIG. 53 is a wearable device for the arm with one or more close-fitting biometric sensors comprising: (a) a first attachment member which is configured to span at least 60% of the circumference of a person's arm; (b) a second attachment member which is configured to span at least 60% of the circumference of the person's arm, wherein the first attachment member and the second attachment member are attached to each other by a mechanism that enables the second attachment member to be circumferentially-rotated relative to the first attachment member; and (c) one or more biometric sensors which are configured to collect data concerning arm tissue, wherein these biometric sensors are part of (or attached to) the second attachment member.

In an example, an attachment member can be a band, ring, strap, bracelet, bangle, or armlet. In an example, a band or other attachment member can be attached to a person's arm by connecting two ends of the attachment member with a clasp, clip, buckle, hook, pin, plug, or hook-and-eye mechanism. In an example, a band or other attachment member can be attached to a person's arm by stretching and sliding it over the person's hand onto the arm. In an example, a band or other attachment member can be attached to a person's arm by applying force to pull two ends apart to slip the member over the arm, wherein the two ends retract back towards each other when the force is removed.

In an example, a first attachment member can be attached to a person's arm in a relatively-fixed manner, so that it does not substantively rotate and/or shift around the circumference of the arm. In an example, a second attachment member can be attached to a person's arm in a relatively-loose manner, so that it can rotate around the circumference of the arm. In an example, a second attachment member can be attached (or connected) to the first attachment member by a connection mechanism which enables the second attachment member to be rotated around the circumference of the person's arm (relative to the first attachment member).

When the second attachment member contains one or more biometric sensors, rotation of the second attachment member also rotates these sensors relative to the circumference of the arm. This enables a user to find the optimal locations around the circumference of the arm from which to collect biometric data for a selected application. In an example, this device can further include a locking mechanism which locks the location of the second attachment member relative to the first attachment member when the optimal location for sensors is found. In an example, a connection mechanism between the two attachment members can be a ball-bearing mechanism. In an example, a connection mechanism can be a sliding tongue-and-groove (or tongue-and-slot) mechanism.

In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

In an example, this device can further comprise one or more components selected from the group consisting of: a data processor; a battery and/or energy harvesting unit; a data transmitter; a data receiver; and a display screen. In an example, a first attachment member can include a display screen on its outward-facing surface. In an example, this device can function as a smart watch. Relevant embodiment variations discussed elsewhere in this or a priority-linked disclosure can also be applied to this example. Specific components in the example shown in FIG. 53 include: first band 5301; second band 5302; display screen 5303; and biometric sensors including 5304.

Figure 54:
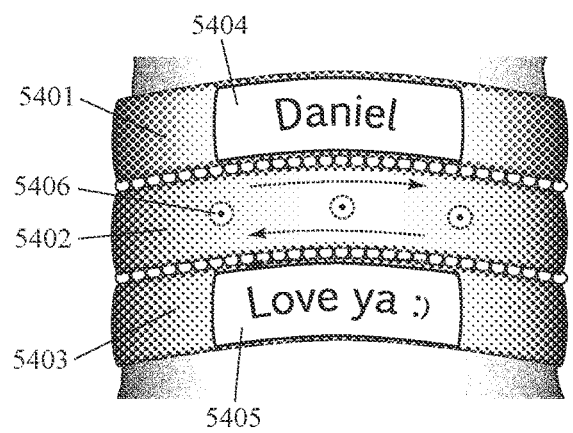
FIG. 54 shows an arm-worn device with biometric sensors and three bands.

FIG. 54 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner. The example shown in FIG. 54 is like the one shown in FIG. 53, except that in FIG. 54 there are three bands instead of two and biometric sensors are on a central band which rotates relative to distal and proximal bands. Such rotation enables adjustment of the locations of one or more biometric sensors relative to the arm in order to improve collection of biometric data from arm tissue.

The example shown in FIG. 54 is a wearable device for the arm with one or more close-fitting biometric sensors comprising: (a) a distal attachment member which is configured to span at least 60% of the circumference of a person's arm; (b) a proximal attachment member which is configured to span at least 60% of the circumference of a person's arm; (c) a central attachment member which is configured to span at least 60% of the circumference of the person's arm, wherein this central attachment member is between the distal and proximal attachment members, and wherein this central attachment member is circumferentially-rotated relative to the distal and proximal attachment members; and (d) one or more biometric sensors which are configured to collect data concerning arm tissue, wherein these biometric sensors are part of (or attached to) the central attachment member.

In an example, an attachment member can be a band, ring, strap, bracelet, bangle, or armlet. In an example, a band or other attachment member can be attached to a person's arm by connecting two ends of the attachment member with a clasp, clip, buckle, hook, pin, plug, or hook-and-eye mechanism. In an example, a band or other attachment member can be attached to a person's arm by stretching and sliding it over the person's hand onto the arm. In an example, a band or other attachment member can be attached to a person's arm by applying force to pull two ends apart to slip the member over the arm, wherein the two ends retract back towards each other when the force is removed.

In an example, distal and proximal attachment members can be attached to a person's arm in a relatively-fixed manner, so that they do not substantively rotate and/or shift around the circumference of the arm. In an example, a central attachment member can be attached to a person's arm in a relatively-loose manner, so that it can rotate around the circumference of the arm. In an example, a central attachment member can be attached (or connected) to the distal and proximal attachment members by a connection mechanism which enables the second attachment member to be rotated around the circumference of the person's arm.

When a central attachment member contains one or more biometric sensors, rotation of the central attachment member also rotates these sensors relative to the circumference of the arm. This enables a user to find the optimal locations around the circumference of the arm from which to collect biometric data for a selected application. In an example, this device can further include a locking mechanism which locks the location of the central attachment member relative to the distal and proximal attachment members when the optimal location for sensors is found. In an example, a connection mechanism between the two attachment members can be a ball-bearing mechanism. In an example, a connection mechanism can be a sliding tongue-and-groove (or tongue-and-slot) mechanism.

In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

In an example, this device can further comprise one or more components selected from the group consisting of: a data processor; a battery and/or energy harvesting unit; a data transmitter; a data receiver; and a display screen. In an example, a distal and/or proximal attachment member can include a display screen on an outward-facing surface. In an example, this device can function as a smart watch. Relevant embodiment variations discussed elsewhere in this or a priority-linked disclosure can also be applied to this example. Specific components in the example shown in FIG. 54 include: distal band 5401; central band 5402; proximal band 5403; display screens 5404 and 5405; and biometric sensors including 5406.

Figure 55:
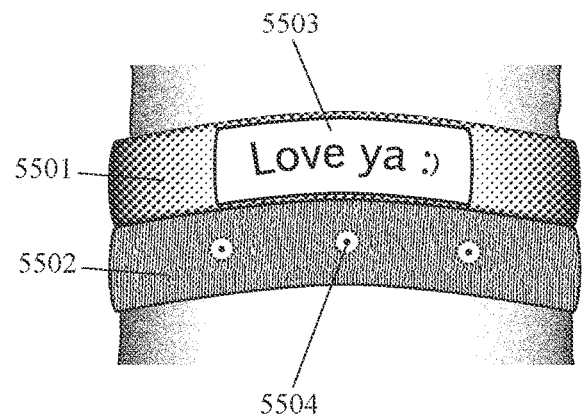
FIG. 55 shows an arm-worn device with biometric sensors, a rigid band, and an elastic band.

FIG. 55 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner. The example shown in FIG. 55 can be described as an arm-wearable device with a relatively-rigid band and a relatively-elastic band, wherein each of these bands spans at least 60% of the circumference of a person's arm, wherein these bands are connected to each other, and wherein there are biometric sensors on the relatively-elastic band.

More specifically, the example shown in FIG. 55 is a wearable device for the arm with one or more close-fitting biometric sensors comprising: (a) an inelastic attachment member which is configured to span at least 60% of the circumference of a person's arm, wherein this inelastic attachment member has a first elasticity level; (b) an elastic attachment member which is configured to span at least 60% of the circumference of a person's arm, wherein this elastic attachment member has a second elasticity level, wherein the second elasticity level is greater than the first elasticity level, and wherein the elastic attachment member is connected to the inelastic attachment member; and (c) one or more biometric sensors which are configured to collect data concerning arm tissue, wherein these biometric sensors are part of (or attached to) the elastic attachment member.

In an example, an attachment member can be a band, ring, strap, bracelet, bangle, armlet, sleeve, or cuff. In an example, a band or other attachment member can be attached to a person's arm by connecting two ends of the attachment member with a clasp, clip, buckle, hook, pin, plug, or hook-and-eye mechanism. In an example, a band or other attachment member can be attached to a person's arm by stretching and sliding it over the person's hand onto the arm. In an example, a band or other attachment member can be attached to a person's arm by applying force to pull two ends apart to slip the member over the arm, wherein the two ends retract back towards each other when the force is removed.

In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

In an example, this device can further comprise one or more components selected from the group consisting of: a data processor; a battery and/or energy harvesting unit; a data transmitter; a data receiver; and a display screen. In an example, this device can function as a smart watch. Relevant embodiment variations discussed elsewhere in this or a priority-linked disclosure can also be applied to this example. Specific components in the example shown in FIG. 55 include: inelastic band 5501; elastic band 5502; display screen 5503; and biometric sensors including 5504.

Figure 56:
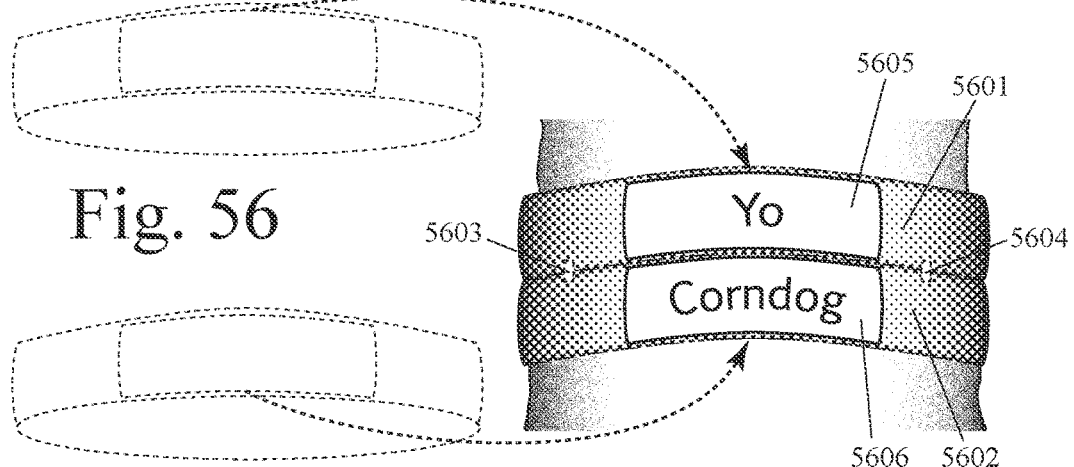
FIG. 56 shows an arm-worn device with biometric sensors and two connectable bands.

FIG. 56 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner. The example shown in FIG. 56 can be described as an arm-wearable device with two or more modular and connectable bands, wherein each band spans at least 60% of the circumference of a person's arm, and wherein one or more of these bands house biometric sensors.

More specifically, the example shown in FIG. 56 is a wearable device for the arm with one or more close-fitting biometric sensors comprising: (a) a first modular band which is configured to span at least 60% of the circumference of a person's arm; (b) a second modular band which is configured to span at least 60% of the circumference of a person's arm, wherein the first modular band and the second modular band have a first configuration in which they are not connected to each other and are not worn by a person, wherein the first band and the second band have a second configuration wherein they are connected to each other and worn on a person's arm, and wherein the first band and the second band can be changed from the first configuration to the second configuration by the person who wears them, and wherein the first band and the second band can be changed back from the second configuration to the first configuration by the person who wears them; and (c) one or more biometric sensors which are configured to collect data concerning arm tissue, wherein these biometric sensors are part of (or attached to) one or both of the modular bands.

In an example, an attachment member can be a band, ring, strap, bracelet, bangle, armlet, sleeve, or cuff. In an example, a band or other attachment member can be attached to a person's arm by connecting two ends of the attachment member with a clasp, clip, buckle, hook, pin, plug, or hook-and-eye mechanism. In an example, a band or other attachment member can be attached to a person's arm by stretching and sliding it over the person's hand onto the arm. In an example, a band or other attachment member can be attached to a person's arm by applying force to pull two ends apart to slip the member over the arm, wherein the two ends retract back towards each other when the force is removed.

In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

In an example, this device can further comprise one or more components selected from the group consisting of: a data processor; a battery and/or energy harvesting unit; a data transmitter; a data receiver; and a display screen. In an example, this device can function as a smart watch. Relevant embodiment variations discussed elsewhere in this or a priority-linked disclosure can also be applied to this example. Specific components in the example shown in FIG. 56 include: first modular band 5601; second modular band 5602; temporary connectors 5603 and 5604; and display screens 5605 and 5606.

Figure 57:
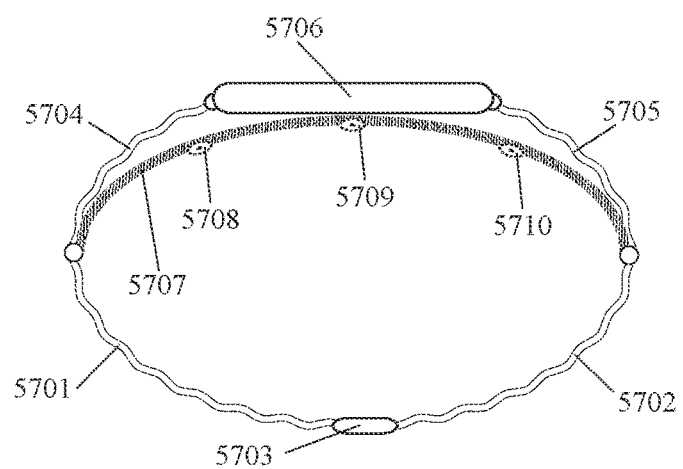
FIG. 57 shows an arm-worn device with biometric sensors, an outer rigid band, and an inner elastic half-band.

FIG. 57 shows another example of a wearable device for the arm with one or more close-fitting biometric sensors. This figure shows the device from a side perspective, as it would appear encircling a lateral cross-section of a person's arm.

The example in FIG. 57 can be described as an arm-wearable device with a partial-circumferential inner elastic band and biometric sensors. Such a device can have an outer inelastic band with a first elasticity level which spans a first percentage of the arm circumference and an inner elastic band with a second elasticity level which spans a second percentage of the arm circumference—wherein the second percentage is less than the first percentage and the second elasticity level is greater than the first elasticity level. In the example shown in FIG. 57, an outer inelastic band (and display screen) spans the entire arm circumference and a semi-circular inner elastic band (interior relative to the outer inelastic band) spans only half of the arm circumference. This design can provide an overall semi-rigid structure (for housing a display screen), but can also keep biometric sensors close against the surface of the arm for consistent collection of biometric data.

More specifically, the example shown in FIG. 57 is a wearable device for the arm with one or more close-fitting biometric sensors comprising: (a) an outer inelastic band which is configured to span a first percentage of a person's arm and which has a first elasticity level; (b) an inner elastic band which is configured to span a second percentage of a person's arm and which has a second elasticity level, wherein this inner elastic band is configured to be closer to the surface of the arm than the outer inelastic band, wherein the second percentage is less than the first percentage, and wherein the second elasticity level is greater than the first elasticity level; and (c) one or more biometric sensors which are configured to collect data concerning arm tissue, wherein these biometric sensors are part of (or attached to) the inner elastic band.

Alternatively, the example shown in FIG. 57 can be specified as a wearable device for the arm with one or more close-fitting biometric sensors comprising: (a) an outer inelastic band with a first arcuate length and a first elasticity level; (b) an inner elastic band with a second arcuate length and a second elasticity level, wherein this inner elastic band is located on the concave side of the outer elastic band, wherein the second percentage is less than the first percentage, and wherein the second elasticity level is greater than the first elasticity level; and (c) one or more biometric sensors which are configured to collect data concerning arm tissue, wherein these biometric sensors are part of (or attached to) the inner elastic band.

In an example, the word "ring", "strap", "bracelet", "bangle", "armlet", "sleeve", or "cuff" can be substituted for the word "band" in the above specifications. In an example, an outer inelastic band can span Y % of the circumference of a person's arm and an inner elastic band can span X % of the circumference of a person's arm, wherein Y % is at least 20 percentage points greater than X %. In an example, Y % can be 75% and X % can be 50%. In an example, the ends of the inner elastic band can be attached to the outer inelastic band. In an example, an inner elastic band can be configured to span the anterior (upper) surface of a person's arm. In an example, an inner elastic band can be configured to span the posterior (lower) surface of a person's arm.

In an example, an outer inelastic band can be attached to a person's arm by connecting two ends of an outer inelastic band with a clasp, clip, buckle, hook, pin, plug, or hook-and-eye mechanism. In an example, an outer inelastic band can be attached to a person's arm by stretching and sliding it over the person's hand onto the arm. In an example, an outer inelastic band can be attached to a person's arm by applying force to pull two ends apart to slip the member over the arm, wherein the two ends retract back towards each other when the force is removed.

In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

In an example, this device can further comprise one or more components selected from the group consisting of: a data processor; a battery and/or energy harvesting unit; a data transmitter; a data receiver; and a display screen. In an example, this device can function as a smart watch. Relevant embodiment variations discussed elsewhere in this or a priority-linked disclosure can also be applied to this example. Specific components in the example shown in FIG. 57 include: four segments (5701, 5702, 5704, and 5705) of an outer inelastic band; inner elastic band 5707; biometric sensors (5708, 5709, and 5710); outer elastic band clasp 5703; and display screen 5706.

Figure 58:
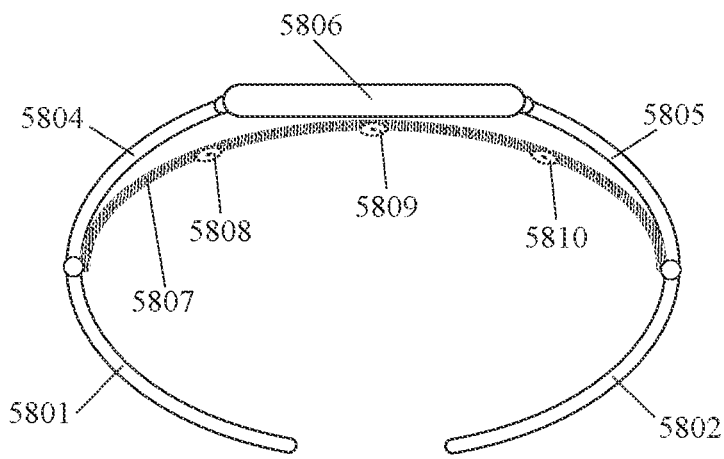
FIG. 58 shows an arm-worn device with biometric sensors, an outer rigid bracelet, and an inner elastic half-band.

FIG. 58 shows another example of a wearable device for the arm with one or more close-fitting biometric sensors. This figure shows the device from a side perspective, as it would appear encircling a lateral cross-section of a person's wrist (or other portion of their arm). The example in FIG. 58 is like the one shown in FIG. 57, except that in FIG. 58 the outer inelastic band is sufficiently resilient that its ends hold onto the person's arm without the need for a clasp. The outer inelastic band can be attached to a person's arm by applying force to pull two ends apart to slip the member over the arm, wherein the two ends retract back towards each other when the force is removed.

In an example, this device can further comprise one or more components selected from the group consisting of: a data processor; a battery and/or energy harvesting unit; a data transmitter; a data receiver; and a display screen. In an example, this device can function as a smart watch. Relevant embodiment variations discussed elsewhere in this or a priority-linked disclosure can also be applied to this example. Specific components in the example shown in FIG. 58 include: four segments (5801, 5802, 5804, and 5805) of an outer inelastic band; inner elastic band 5807; biometric sensors (5808, 5809, and 5810); and display screen 5806.

Figure 59:
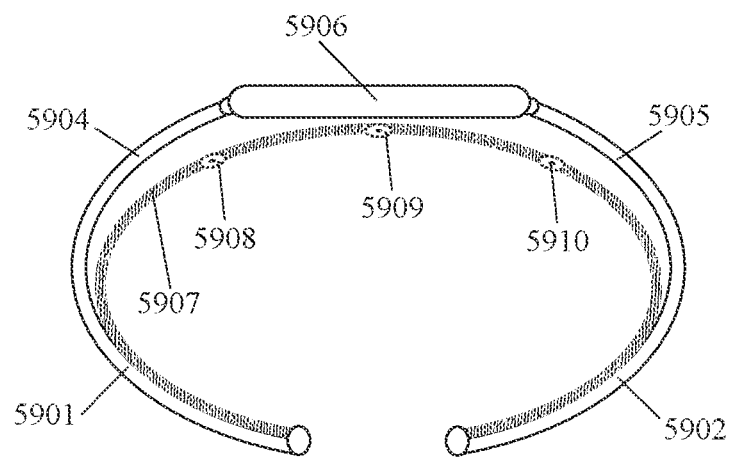
FIG. 59 shows an arm-worn device with biometric sensors, an outer rigid bracelet, and an inner elastic band.

FIG. 59 shows another example of a wearable device for the arm with one or more close-fitting biometric sensors. This figure shows the device from a side perspective, as it would appear encircling a lateral cross-section of a person's arm. The example in FIG. 59 can be described as an arm-wearable device with an outer arcuate inelastic band, an inner arcuate elastic band, and biometric sensors which are part of the inner band. This design can provide an overall semi-rigid structure (e.g. to hold a rigid display screen in place) and also keep biometric sensors close against the surface of the arm for consistent collection of biometric data.

The example shown in FIG. 59 can be specified as a wearable device for the arm with one or more close-fitting biometric sensors comprising: (a) an outer arcuate inelastic band which is configured to span at least 60% of the circumference of a person's arm and which has a first elasticity level; (b) an inner arcuate elastic band which is located on (and attached to) the concave side of the outer arcuate band and which has a second elasticity level, wherein the second elasticity level is greater than the first elasticity level; and (c) one or more biometric sensors which are configured to collect data concerning arm tissue, wherein these biometric sensors are part of (or attached to) the inner arcuate elastic band. In various examples, a ring, strap, bracelet, bangle, armlet, sleeve, or cuff can be substituted for a band.

Alternatively, the example shown in FIG. 59 can be specified as a wearable device for the arm with one or more close-fitting biometric sensors comprising: (a) an outer arcuate inelastic band, wherein this outer arcuate inelastic band is configured to span at least 60% of the circumference of a person's arm, wherein this outer arcuate inelastic band is configured to be a first average distance from the surface of the person's arm, and wherein this outer arcuate inelastic band has a first elasticity level; (b) an inner arcuate elastic band, wherein this inner arcuate elastic band is attached to the outer arcuate inelastic band, wherein this inner arcuate elastic band is configured to be an second average distance from the surface of the person's arm, wherein this inner arcuate elastic band has a second elasticity level, wherein the second average distance is less than the first average distance, and wherein the second elasticity level is greater than the first elasticity level; and (c) one or more biometric sensors which are configured to collect data concerning arm tissue, wherein these biometric sensors are part of (or attached to) the inner arcuate elastic band. In various examples, a ring, strap, bracelet, bangle, armlet, sleeve, or cuff can be substituted for a band.

In an example, an outer arcuate inelastic band can be attached to a person's arm by connecting two ends of the outer inelastic band with a clasp, clip, buckle, hook, pin, plug, or hook-and-eye mechanism. In an example, an outer arcuate inelastic band can be attached to a person's arm by stretching and sliding it over the person's hand onto the arm. In an example, an outer arcuate inelastic band can be attached to a person's arm by applying force to pull two ends apart to slip the member over the arm, wherein the two ends retract back towards each other when the force is removed. In an example, an inner arcuate elastic band can be made from a stretchable fabric. In an example, an inner arcuate elastic band can be attached to an outer arcuate inelastic band at the ends of the arcuate inelastic band. In an example, an inner arcuate elastic band can be attached to an outer arcuate inelastic band near mid-points of segments of the outer arcuate inelastic band.

In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

In an example, this device can further comprise one or more components selected from the group consisting of: a data processor; a battery and/or energy harvesting unit; a data transmitter; a data receiver; and a display screen. In an example, this device can function as a smart watch. Relevant embodiment variations discussed elsewhere in this or a priority-linked disclosure can also be applied to this example. Specific components in the example shown in FIG. 59 include: four segments (5901, 5902, 5904, and 5905) of an outer inelastic band; inner elastic band 5907; biometric sensors (5908, 5909, and 5910); and display screen 5906.

Figure 60:
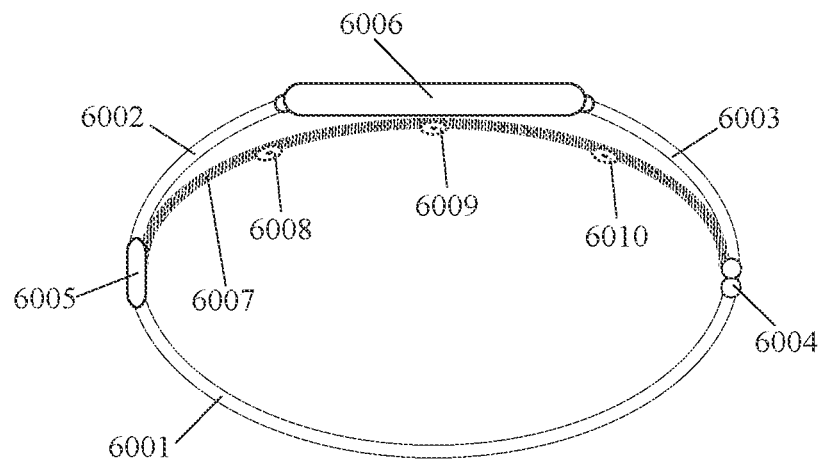
FIG. 60 shows an arm-worn device with biometric sensors, a clam-shell outer band, and an upper inner elastic half-band.

FIG. 60 shows another example of a wearable device for the arm with one or more close-fitting biometric sensors. This figure shows the device from a side perspective, as it would appear encircling a lateral cross-section of a person's wrist (or other portion of the person's arm). The example in FIG. 60 can be described as an arm-wearable device with an outer rigid "clam shell" structure to hold a display screen in place and an inner arcuate elastic band to keep biometric sensors close against the surface of the arm.

The example shown in FIG. 60 can be specified as a wearable device for the arm with one or more close-fitting biometric sensors comprising: (a) a clam shell structure which is configured to span the circumference of a person's arm, wherein this clam shell structure further comprises: an upper half-circumferential portion, a lower half-circumferential portion, a joint (and/or hinge) between these portions on a first side of these portions, and a connector which reversibly connects these portions on a second side of these portions; (b) an arcuate elastic band which is located within the concavity of the clam shell structure and is attached to the clam shell structure; and (c) one or more biometric sensors which are configured to collect data concerning arm tissue, wherein these biometric sensors are part of (or attached to) the arcuate elastic band.

In an example, an upper half-circumferential portion of a clam shell structure can span the anterior (upper) surface of a person's arm and a lower half-circumferential portion of a clam shell structure can span the posterior (lower) surface of the person's arm. In an example, there can be a display screen on the outer surface of one or both portions of a clam shell structure. In an example, a connector which reversibly connects the upper and lower portions of a clam shell structure can be selected from the group consisting of: clasp, clip, buckle, hook, pin, plug, and hook-and-eye mechanism. In an example, an inner arcuate elastic band can be made from a stretchable fabric. In an example, an inner arcuate elastic band can be attached to an upper half-circumferential portion of a clam shell structure.

In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

In an example, this device can further comprise one or more components selected from the group consisting of: a data processor; a battery and/or energy harvesting unit; a data transmitter; a data receiver; and a display screen. In an example, this device can function as a smart watch. Relevant embodiment variations discussed elsewhere in this or a priority-linked disclosure can also be applied to this example. Specific components in the example shown in FIG. 60 include: two segments 6002 and 6003 of an upper half-circumferential portion of a clam shell structure; a lower half-circumferential portion 6001 of the clam shell structure; a joint (or hinge) 6004 between the upper and lower portions of the clam shell structure; a reversible connector 6005 between the upper and lower portions of the clam shell structure; an inner elastic band 6007; biometric sensors 6008, 6009, and 6010; and display screen 6006.

Figure 61:
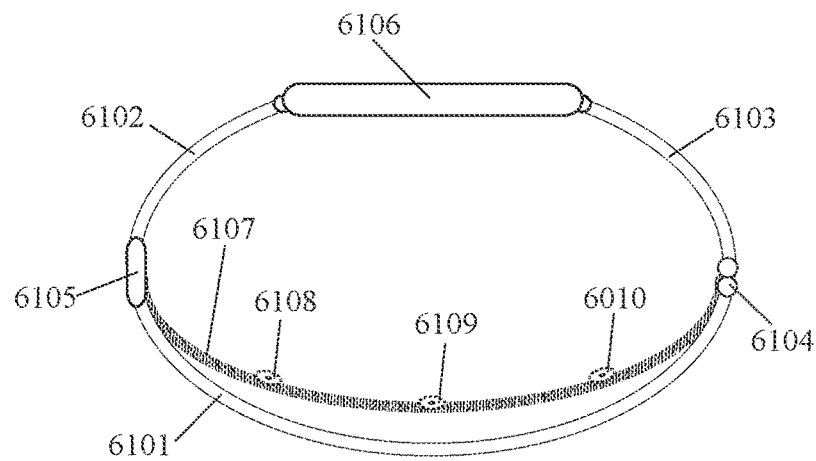
FIG. 61 shows an arm-worn device with biometric sensors, a clam-shell outer band, and a lower inner elastic half-band.

FIG. 61 shows another example of a wearable device for the arm with one or more close-fitting biometric sensors. This figure shows the device from a side perspective, as it would appear encircling a lateral cross-section of a person's wrist (or other portion of the person's arm). The example in FIG. 61 is like the one shown in FIG. 60, except that in FIG. 61 an inner arcuate elastic band spans the posterior (lower) surface of a person's arm. Specific components in the example shown in FIG. 61 include: two segments 6102 and 6103 of an upper half-circumferential portion of a clam shell structure; a lower half-circumferential portion 6101 of the clam shell structure; a joint (or hinge) 6104 between the upper and lower portions of the clam shell structure; a reversible connector 6105 between the upper and lower portions of the clam shell structure; an inner elastic band 6107; biometric sensors 6108, 6109, and 6110; and display screen 6106.

Figure 62:
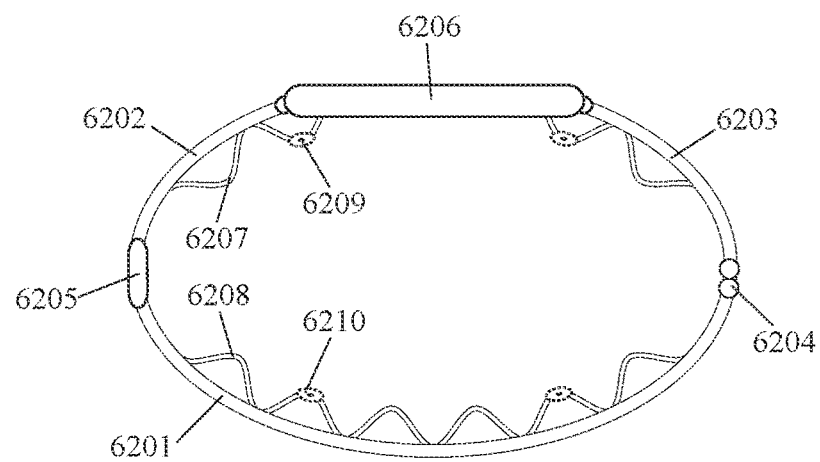
FIG. 62 shows an arm-worn device with biometric sensors, a clam-shell outer band, and an undulating inner flexible band.

FIG. 62 shows another example of a wearable device for the arm with one or more close-fitting biometric sensors. This figure shows the device from a side perspective, as it would appear encircling a lateral cross-section of a person's wrist (or other portion of the person's arm). The example in FIG. 62 can be described as an arm-wearable device with an outer rigid "clam shell" structure and inward-facing flexible undulations to keep biometric sensors close against the surface of the arm.

The example shown in FIG. 62 can be specified as a wearable device for the arm with one or more close-fitting biometric sensors comprising: (a) a clam shell structure which is configured to span the circumference of a person's arm, wherein this clam shell structure further comprises: an upper half-circumferential portion, a lower half-circumferential portion, a joint (and/or hinge) between these portions on a first side of these portions, and a connector which reversibly connects these portions on a second side of these portions; (b) an inward-facing undulating member which is part of (or attached to) the clam shell structure; and (c) one or more biometric sensors which are configured to collect data concerning arm tissue, wherein these biometric sensors are part of (or attached to) the undulating member.

In an example, an upper half-circumferential portion of a clam shell structure can span the anterior (upper) surface of a person's arm and a lower half-circumferential portion of a clam shell structure can span the posterior (lower) surface of the person's arm. In an example, there can be a display screen on the outer surface of one or both portions of a clam shell structure. In an example, a connector which reversibly connects the upper and lower portions of a clam shell structure can be selected from the group consisting of: clasp, clip, buckle, hook, pin, plug, and hook-and-eye mechanism. In an example, an inward-facing undulating member can have a sinusoidal shape. In an example, an inward-facing undulating member can be flexible and/or compressible. In an example, an inward-facing undulating member can be elastic and filled with a liquid, gel, or gas.

In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

In an example, this device can further comprise one or more components selected from the group consisting of: a data processor; a battery and/or energy harvesting unit; a data transmitter; a data receiver; and a display screen. In an example, this device can function as a smart watch. Relevant embodiment variations discussed elsewhere in this or a priority-linked disclosure can also be applied to this example. Specific components in the example shown in FIG. 62 include: two segments 6202 and 6203 of an upper half-circumferential portion of a clam shell structure; a lower half-circumferential portion 6201 of the clam shell structure; a joint (or hinge) 6204 between the upper and lower portions of the clam shell structure; a reversible connector 6205 between the upper and lower portions of the clam shell structure; inward-facing undulating members including 6207 and 6208; biometric sensors including 6209 and 6210; and display screen 6206.

Figure 63:
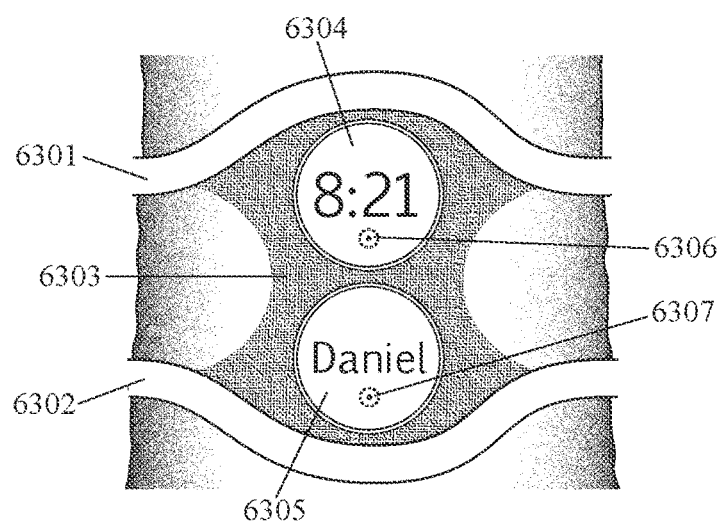
FIG. 63 shows an arm-worn device with biometric sensors and two bands connected by an hour-glass-shaped elastic member.

FIG. 63 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner. The example in FIG. 63 can be described as an arm-wearable device with two display screens suspended by an elastic material between two arcuate bands.

The example shown in FIG. 63 can be specified as a wearable device for the arm with one or more close-fitting biometric sensors comprising: (a) a distal arcuate band which is configured to span at least 60% of the circumference of a person's arm; (b) a proximal arcuate band which is configured to span at least 60% of the circumference of a person's arm, wherein distal is defined as further from a person's shoulder and proximal is defined as closer to the person's shoulder; (c) an elastic member that is between the distal arcuate band and the proximal arcuate band which connects the distal actuate band to the proximal arcuate band; and (d) two arcuate display screens between the distal arcuate band and the proximal arcuate band, wherein these display screens are attached to the elastic member; and (e) one or more biometric sensors which are configured to collect data concerning arm tissue. In various examples, a ring, strap, bracelet, or bangle can be substituted for a band.

In an example, an arcuate band can undulate laterally as it spans the circumference a person's arm. In an example, distal and proximal arcuate bands can curve away from each other as they span a central portion of the anterior (upper) surface of a person's arm and can curve back toward each other as they span a side surface of the person's arm. In an example, an arcuate band can be attached to a person's arm by connecting two ends of the arcuate band with a clasp, clip, buckle, hook, pin, plug, or hook-and-eye mechanism. In an example, an arcuate band can be attached to a person's arm by stretching and sliding it over the person's hand onto the arm. In an example, an arcuate band can be attached to a person's arm by applying force to pull two ends apart to slip the member over the arm, wherein the two ends retract back towards each other when the force is removed.

In an example, an elastic member can be made from elastic fabric. In an example, an elastic member can be an elastic mesh. In an example, an elastic member can have four arcuate sides: two convex sides and two concave sides. In an example, one concave side can connect to the distal arcuate band and the other concave side can connect to the proximal band. In an example, two convex sides can be between the two bands. In an example, an elastic member can completely surround the perimeters of two display screens. In an example, an elastic member can flexibly-suspend two display screens between two arcuate bands. In an example, a display screen can be circular. In an example, the centers of two display screens can be connected to form a virtual line which is parallel to the longitudinal axis of an arm. In an example, the centers of two display screens can be connected to form a virtual line which is parallel to a line which is perpendicular to the circumferences of distal and proximal arcuate bands.

In an example, biometric sensors can be part of (or attached to) display screens and/or enclosures which house display screens. In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

In an example, this device can further comprise one or more components selected from the group consisting of: a data processor; a battery and/or energy harvesting unit; a data transmitter; a data receiver; and a display screen. In an example, this device can function as a smart watch. Relevant embodiment variations discussed elsewhere in this or a priority-linked disclosure can also be applied to this example. Specific components in the example shown in FIG. 63 include: distal arcuate band 6301; proximal arcuate band 6302; elastic member 6303 between the two arcuate bands; display screens 6304 and 6305 suspended by the elastic member; and biometric sensors 6306 and 6307.

Figure 64:
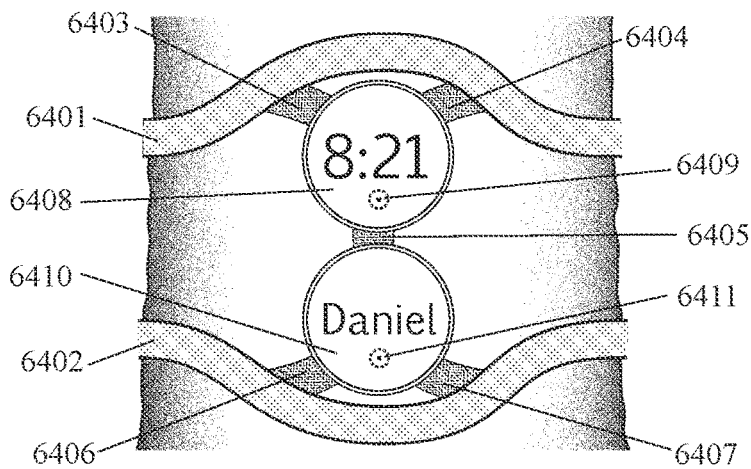
FIG. 64 shows an arm-worn device with biometric sensors and two bands connected by two elastic members.

FIG. 64 shows another example of a wearable device for the arm with one or more close-fitting biometric sensors.

This figure shows the device from a top-down perspective, as it would appear spanning the anterior (upper) surface of a person's wrist (or other portion of the person's arm) in a circumferential manner. The example in FIG. 64 can be described as an arm-wearable device with two display screens which are suspended by elastic straps between two arcuate bands.

The example shown in FIG. 64 can be specified as a wearable device for the arm with one or more close-fitting biometric sensors comprising: (a) a distal arcuate band which is configured to span at least 60% of the circumference of a person's arm; (b) a proximal arcuate band which is configured to span at least 60% of the circumference of a person's arm, wherein distal is further from a person's shoulder and proximal is closer to the person's shoulder; (c) a plurality of elastic straps between the distal arcuate band and the proximal arcuate band which connect the distal actuate band to the proximal arcuate band; and (d) two arcuate display screens between the distal arcuate band and the proximal arcuate band, wherein these display screens are attached to the plurality of elastic straps; and (e) one or more biometric sensors which are configured to collect data concerning arm tissue. In an example, a ring, bracelet, or bangle can be substituted for a band.

In an example, an arcuate band can undulate laterally as it spans the circumference a person's arm. In an example, distal and proximal arcuate bands can curve away from each other as they span a central portion of the anterior (upper) surface of a person's arm and can curve back toward each other as they span a side surface of the person's arm. In an example, an arcuate band can be attached to a person's arm by connecting two ends of the arcuate band with a clasp, clip, buckle, hook, pin, plug, or hook-and-eye mechanism. In an example, an arcuate band can be attached to a person's arm by stretching and sliding it over the person's hand onto the arm. In an example, an arcuate band can be attached to a person's arm by applying force to pull two ends apart to slip the member over the arm, wherein the two ends retract back towards each other when the force is removed.

In an example, an elastic strap can be made from elastic fabric. In an example, an elastic strap can be an elastic mesh. In an example, each display screen can be connected to three elastic straps. In an example, each display screen can be connected to three elastic straps with connection points which are substantially equidistant around the circumference of a display screen. In an example, each arcuate band can be connected to two elastic straps. In an example, two display screens can be connected by one elastic strap. In an example, there can be five elastic straps in total. In an example, a display screen can be circular. In an example, the centers of two display screens can be connected to form a virtual line which is parallel to the longitudinal axis of an arm. In an example, the centers of two display screens can be connected to form a virtual line which is parallel to a line which is perpendicular to the circumferences of distal and proximal arcuate bands.

In an example, biometric sensors can be part of (or attached to) display screens and/or enclosures which house display screens. In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

In an example, this device can further comprise one or more components selected from the group consisting of: a data processor; a battery and/or energy harvesting unit; a data transmitter; a data receiver; and a display screen. In an example, this device can function as a smart watch. Relevant embodiment variations discussed elsewhere in this or a priority-linked disclosure can also be applied to this example. Specific components in the example shown in FIG. 64 include: distal arcuate band 6401; proximal arcuate band 6402; a plurality of elastic straps including 6403, 6404, 6405, 6406, and 6407; display screens 6408 and 6410 suspended by the elastic straps; and biometric sensors 6409 and 6411.

Figure 65:
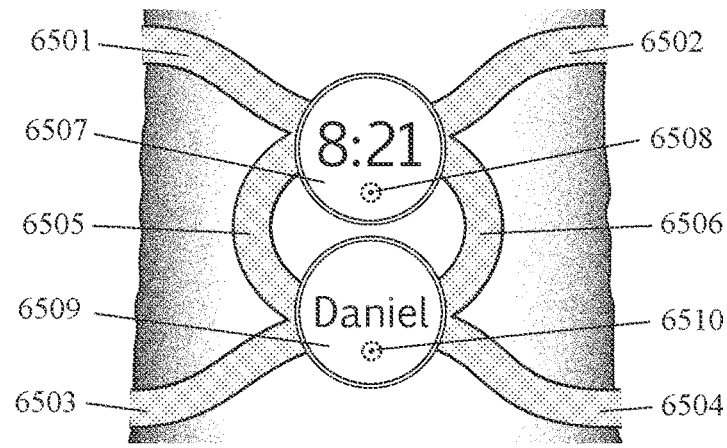
FIG. 65 shows an arm-worn device with biometric sensors and two undulating bands.

FIG. 65 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner. The example in FIG. 65 can be described as an arm-wearable device with two display screens whose centers are at 12 o'clock and 6 o'clock positions around a circular band on the anterior (upper) surface of an arm.

The example shown in FIG. 65 can be specified as a wearable device for the arm with one or more close-fitting biometric sensors comprising: (a) a distal arcuate band which is configured to span at least 60% of the circumference of a person's arm; (b) a proximal arcuate band which is configured to span at least 60% of the circumference of a person's arm, wherein distal is further from a person's shoulder and proximal is closer to the person's shoulder; (c) a distal display screen on the distal arcuate band; (d) a proximal display screen on the proximal arcuate band; (e) a right circle-segment band which connects the right side of the distal display screen to the right side of the proximal display screen; (f) a left circle-segment band which connects the left side of the distal display screen to the left side of the proximal display screen; and (g) one or more biometric sensors which are configured to collect data concerning arm tissue.

In an example, an arcuate band can be attached to a person's arm by connecting two ends of the arcuate band with a clasp, clip, buckle, hook, pin, plug, or hook-and-eye mechanism. In an example, an arcuate band can be attached to a person's arm by stretching and sliding it over the person's hand onto the arm. In an example, an arcuate band can be attached to a person's arm by applying force to pull two ends apart to slip the member over the arm, wherein the two ends retract back towards each other when the force is removed. In an example, a display screen can be circular. In an example, the centers of two display screens can be connected to form a virtual line which is parallel to the longitudinal axis of an arm. In an example, the centers of two display screens can be connected to form a virtual line which is parallel to a line which is perpendicular to the circumferences of distal and proximal arcuate bands.

In an example, biometric sensors can be part of (or attached to) display screens and/or enclosures which house display screens. In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

In an example, this device can further comprise one or more components selected from the group consisting of: a data processor; a battery and/or energy harvesting unit; a data transmitter; a data receiver; and a display screen. In an example, this device can function as a smart watch. Relevant embodiment variations discussed elsewhere in this or a priority-linked disclosure can also be applied to this example. Specific components in the example shown in FIG. 65 include: portions 6501 and 6502 of a distal arcuate band; portions 6503 and 6504 of a proximal arcuate band; display screens 6507 and 6509; right circle-segment band 6506; left circle-segment band 6505; and biometric sensors 6508 and 6510.

Figure 66:
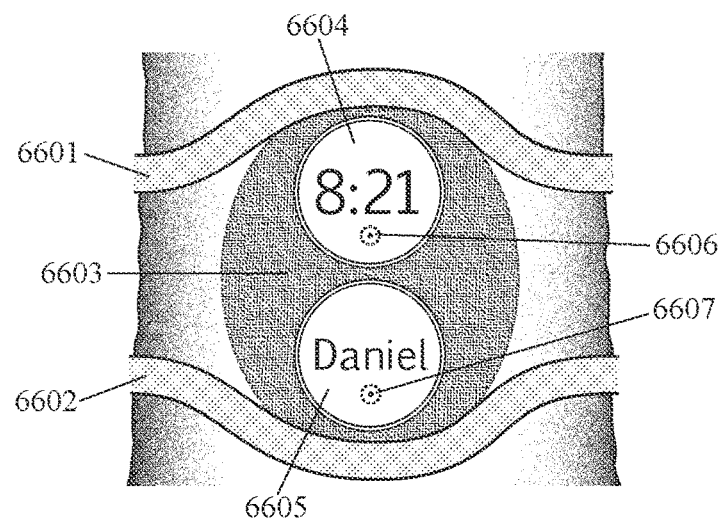
FIG. 66 shows an arm-worn device with biometric sensors and two bands connected by an oval-shaped elastic member.

FIG. 66 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner. The example in FIG. 66 can be described as an arm-wearable device with two display screens suspended by an oval (or elliptical or circular) elastic member between two arcuate bands.

The example shown in FIG. 66 can be specified as a wearable device for the arm with one or more close-fitting biometric sensors comprising: (a) a distal arcuate band which is configured to span at least 60% of the circumference of a person's arm; (s) a proximal arcuate band which is configured to span at least 60% of the circumference of a person's arm, wherein distal is defined as further from a person's shoulder and proximal is defined as closer to the person's shoulder; (t) an oval (or elliptical or circular) elastic member that is between the distal arcuate band and the proximal arcuate band which connects the distal actuate band to the proximal arcuate band; and (r) two arcuate display screens between the distal arcuate band and the proximal arcuate band, wherein these display screens are attached to the oval (or elliptical or circular) elastic member; and (o) one or more biometric sensors which are configured to collect data concerning arm tissue. In various examples, a ring, strap, bracelet, or bangle can be substituted for a band.

In an example, an arcuate band can undulate laterally as it spans the circumference a person's arm. In an example, distal and proximal arcuate bands can curve away from each other as they span a central portion of the anterior (upper) surface of a person's arm and can curve back toward each other as they span a side surface of the person's arm. In an example, an arcuate band can be attached to a person's arm by connecting two ends of the arcuate band with a clasp, clip, buckle, hook, pin, plug, or hook-and-eye mechanism. In an example, an arcuate band can be attached to a person's arm by stretching and sliding it over the person's hand onto the arm. In an example, an arcuate band can be attached to a person's arm by applying force to pull two ends apart to slip the member over the arm, wherein the two ends retract back towards each other when the force is removed.

In an example, an oval (or elliptical or circular) elastic member can be made from elastic fabric. In an example, an oval (or elliptical or circular) elastic member can be an elastic mesh. In an example, an oval (or elliptical or circular) elastic member can completely surround the perimeters of two display screens. In an example, an oval (or elliptical or circular) elastic member can flexibly-suspend two display screens between two arcuate bands. In an example, a display screen can be circular. In an example, the centers of two display screens can be connected to form a virtual line which is parallel to the longitudinal axis of an arm. In an example, the centers of two display screens can be connected to form a virtual line which is parallel to a line which is perpendicular to the circumferences of distal and proximal arcuate bands.

In an example, biometric sensors can be part of (or attached to) display screens and/or enclosures which house display screens. In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

In an example, this device can further comprise one or more components selected from the group consisting of: a data processor; a battery and/or energy harvesting unit; a data transmitter; a data receiver; and a display screen. In an example, this device can function as a smart watch. Relevant embodiment variations discussed elsewhere in this or a priority-linked disclosure can also be applied to this example. Specific components in the example shown in FIG. 66 include: distal arcuate band 6601; proximal arcuate band 6602; oval (or elliptical or circular) elastic member 6603 between the two arcuate bands; display screens 6604 and 6605 suspended by the oval (or elliptical or circular) elastic member; and biometric sensors 6606 and 6607.

In an example, a wearable device for the arm with a plurality of close-fitting spectroscopic sensors can comprise: an attachment member which is configured to span at least a portion of the circumference of a person's arm; an enclosure which is part of and/or attached to the attachment member; a first spectroscopic sensor in the enclosure which is configured to project a beam of light onto the arm surface at a first angle relative to the enclosure; and a second spectroscopic sensor in the enclosure which is configured to project a beam of light onto the arm surface at a second angle relative to the enclosure, wherein the first angle differs from the second angle by at least 10 degrees.

In an example, an attachment member can be selected from the group consisting of: strap, band, bracelet, ring, armlet, cuff, and sleeve. In an example, an attachment member can be configured to be attached to the person's arm by connecting two ends of the attachment member with a clasp, clip, buckle, hook, pin, plug, or hook-and-eye mechanism. In an example, an attachment member can be configured to be attached to the person's arm by stretching and sliding it over the person's hand onto the arm.

In an example, data from first and/or second spectroscopic sensors can be analyzed to measure a person's hydration levels. In an example, data from first and/or second spectroscopic sensors can be analyzed to measure a person's oxygen levels. In an example, data from first and/or second spectroscopic sensors can be analyzed to measure a person's glucose levels. In an example, data from first and/or second spectroscopic sensors can be analyzed to measure a person's heart rate.

In an example, a wearable device for the arm with one or more close-fitting biometric sensors can comprise: an attachment member which is configured to span at least a portion of the circumference of a person's arm; an enclosure which is part of and/or attached to the attachment member; an elastic member filled with a fluid, gel, or gas which is attached to and/or part of the enclosure; and one or more biometric sensors which are configured to record biometric data concerning the person's arm tissue, wherein these one or more biometric sensors are attached to a circumference-center-facing wall of the elastic member.

In an example, a biometric sensor can be a spectroscopic sensor which is configured to measure the spectrum of light energy reflected from and/or absorbed by tissue of the person's arm. In an example, a biometric sensor can be an electromagnetic energy sensor which is configured to measure parameters and/or patterns of electromagnetic energy passing through and/or emitted by tissue of the person's arm. In an example, measured parameters and/or patterns of electromagnetic energy can be selected from the group consisting of: impedance, resistance, conductivity, permittivity, and electromagnetic wave pattern.

In an example, data from a biometric sensor can be analyzed to measure a person's hydration levels. In an example, data from a biometric sensor can be analyzed to measure a person's oxygen levels. In an example, data from a biometric sensor can be analyzed to measure a person's glucose levels. In an example, data from a biometric sensor can be analyzed to measure a person's heart rate.

In an example, a wearable device for the arm with a close-fitting biometric sensor can comprise: a circumferentially-undulating attachment member which is configured to span at least a portion of the circumference of a person's arm; and a plurality of biometric sensors which collect data concerning arm tissue, wherein each biometric sensor is located at the proximal portion of an undulation, and wherein the proximal portion of an undulation is the portion of an undulating wave which is closest to the circumferential center of the device.

In an example, a biometric sensor can be a spectroscopic sensor which is configured to measure the spectrum of light energy reflected from and/or absorbed by tissue of the person's arm. In an example, a biometric sensor can be an electromagnetic energy sensor which is configured to measure parameters and/or patterns of electromagnetic energy passing through and/or emitted by tissue of the person's arm selected from the group consisting of: impedance, resistance, conductivity, permittivity, and electromagnetic wave pattern.

In an example, data from a plurality of biometric sensors can be analyzed to measure a person's hydration levels. In an example, data from a plurality of biometric sensors can be analyzed to measure a person's oxygen levels. In an example, data from the plurality of biometric sensors can be analyzed to measure a person's glucose levels. In an example, data from the plurality of biometric sensors can be analyzed to measure a person's heart rates.

I claim:

1. An arm wearable device with a close-fitting spectroscopic sensor comprising:
    an attachment member which is configured to span at least a portion of a circumference of a person's arm;
    an enclosure which is part of and/or attached to the attachment member; and
    a rotatable light-projecting spectroscopic sensor, wherein the sensor is rotated relative to the enclosure and wherein rotation of the sensor relative to the enclosure changes the angle at which the sensor projects light onto the surface of the person's arm and the sensor measures the light reflected from and/or absorbed by tissue of the person's arm.

2. The device in claim 1 wherein the attachment member is selected from the group consisting of: strap, band, bracelet, ring, armlet, cuff, and sleeve.

3. The device in claim 1 wherein the attachment member is configured to be attached to the person's arm by connecting two ends of the attachment member with a clasp, clip, buckle, hook, pin, plug, or hook-and-eye mechanism.

4. The device in claim 1 wherein the attachment member is configured to be attached to the person's arm by stretching and sliding it over the person's hand onto the arm.

5. The device in claim 1 further comprising a processor configured to analyze data from the rotatable light-projecting spectroscopic sensor to measure the person's hydration levels.

6. The device in claim 1 further comprising a processor configured to analyze data from the rotatable light-projecting spectroscopic sensor to measure the person's oxygen levels.

7. The device in claim 1 further comprising a processor configured to analyze data from the rotatable light-projecting spectroscopic sensor to measure the person's glucose levels.

8. An arm wearable device with a close-fitting spectroscopic sensor comprising:
    an attachment member which is configured to span at least a portion of a circumference of a person's arm;
    an enclosure which is part of and/or attached to the attachment member; and
    a rotatable light-projecting spectroscopic sensor; wherein the sensor is automatically rotated relative to the enclosure; wherein automatic rotation of the sensor relative to the enclosure changes the angle at which the sensor projects light onto the surface of the person's arm; and wherein the sensor is automatically rotated to record measurements at substantially the same angle of incidence even if the enclosure is tilted with respect to the surface of the person's wrist.

9. The device in claim 8 wherein the attachment member is selected from the group consisting of: strap, band, bracelet, ring, armlet, cuff, and sleeve.

10. The device in claim 8 wherein a spectroscopic sensor is configured to measure the spectrum of light energy reflected from and/or absorbed by tissue of the person's arm.

11. The device in claim 8 further comprising a processor configured to analyze data from the rotatable light-projecting spectroscopic sensor to measure the person's hydration levels.

12. The device in claim 8 further comprising a processor configured to analyze data from the rotatable light-projecting spectroscopic sensor to measure the person's oxygen levels.

13. The device in claim 8 further comprising a processor configured to analyze data from the rotatable light-projecting spectroscopic sensor to measure the person's glucose levels.

* * * * *